(12) United States Patent
Park et al.

(10) Patent No.: US 7,854,999 B2
(45) Date of Patent: Dec. 21, 2010

(54) ORGANOELECTROLUMINESCENT COMPOUND AND ORGANOELECTROLUMINESCENT DEVICE EMPLOYING THE SAME

(75) Inventors: Sang-Hoon Park, Yongin-si (KR); Yu-Jin Kim, Yongin-si (KR); Jhun-Mo Son, Yongin-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 609 days.

(21) Appl. No.: 11/826,790

(22) Filed: Jul. 18, 2007

(65) Prior Publication Data

US 2008/0100207 A1    May 1, 2008

(30) Foreign Application Priority Data

Oct. 31, 2006    (KR)    ................. 10-2006-0106726

(51) Int. Cl.
*H01J 1/62*    (2006.01)
*C07C 13/62*    (2006.01)

(52) U.S. Cl. ............... 428/690; 313/504; 540/479; 548/440

(58) Field of Classification Search ........... None
See application file for complete search history.

(56) References Cited

U.S. PATENT DOCUMENTS 4,356,429 A    10/1982    Tang
4,885,211 A    12/1989    Tang et al.
5,151,629 A    9/1992    VanSlyke
2005/0074630 A1*    4/2005    Kanno et al. ............... 428/690
2005/0106418 A1*    5/2005    Kim et al. ................. 428/690
2008/0079356 A1    4/2008    Park et al.
2008/0093987 A1    4/2008    Park et al.

FOREIGN PATENT DOCUMENTS

JP    11-003782    4/1999

OTHER PUBLICATIONS

Yoshiyuki Kuwabara et al., "Thermally Stable Multilayered Organic Electrolunimescent Devices Using Novel Starburst Molecules, 4,4',4''-Tri(N-carbazolyl)triphenylamine (TCTA) and 4,4',4''-Tris(3-methylphenylphenyl-amino)triphenylamine (m-MTDATA), as Hole-Transport Materials", Adv. Mater. 1994, 6, No. 9, pp. 677-679.

* cited by examiner

*Primary Examiner*—D. Lawrence Tarazano
*Assistant Examiner*—Gregory Clark
(74) *Attorney, Agent, or Firm*—Robert E. Bushnell, Esq.

(57) ABSTRACT

Provided are a cyclopentaphenanthrene-based compound and an organoelectroluminescent device employing the same. The cyclopentaphenanthrene-based compound is easy to prepare and excellent in solubility, color purity, color stability, and thermal stability. The cyclopentaphenanthrene-based compound is useful as a material for forming an organic layer, in particular, an emitting layer, in an organoelectroluminescent device, and as an organic dye or an electronic material such as a nonlinear optical material.

19 Claims, 2 Drawing Sheets

ORGANOELECTROLUMINESCENT COMPOUND AND ORGANOELECTROLUMINESCENT DEVICE EMPLOYING THE SAME

CROSS-REFERENCE TO RELATED PATENT APPLICATION AND CLAIM OF PRIORITY

This application claims priority from Korean Patent Application No. 10-2006-0106726, filed on Oct. 31, 2006, in the Korean Intellectual Property Office, the disclosure of which is incorporated herein in its entirety by reference.

BACKGROUND OF THE INVENTION

1. Field of the Invention

The present invention relates to a cyclopentaphenanthrene-based compound and an organoelectroluminescent device employing the same. More particularly, the present invention relates to a cyclopentaphenanthrene-based compound and an organoelectroluminescent device including an organic layer formed of the cyclopentaphenanthrene-based compound.

2. Description of the Related Art

Organoelectroluminescent devices are active emission display devices that emit light by recombination of electrons and holes in a thin layer (hereinafter, referred to as "organic layer") formed of a fluorescent or phosphorescent organic compound when a current is supplied to the organic layer. The organoelectroluminescent devices have advantages such as lightness, simple constitutional elements and thus easy fabrication process, superior image quality, and a wide viewing angle. In addition, the organoelectroluminescent devices can perfectly create dynamic images, achieve high color purity, and have electrical properties suitable for portable electronic equipment due to low power consumption and low driving voltage.

Eastman Kodak Co. has developed an organoelectroluminescent device with a multi-layered structure including an aluminum quinolinol complex layer and a triphenylamine derivative layer (U.S. Pat. No. 4,885,211), and an organoelectroluminescent device including an organic light-emitting layer formed of a low molecular weight material capable of emitting light in a broad wavelength range from UV to infra-red light (U.S. Pat. No. 5,151,629).

Light-emitting devices are self-emitting devices and have advantages such as a wide viewing angle, good contrast, and a rapid response time. Light-emitting devices can be classified into inorganic light-emitting devices using an emitting layer formed of an inorganic compound and Organic Light-Emitting Devices (OLEDs) using an emitting layer formed of an organic compound. OLEDs show better brightness, driving voltage, and response speed characteristics and can create polychromatic light, compared to inorganic light-emitting devices, and thus, extensive research into OLEDs has been conducted.

Generally, OLEDs have a stacked structure including an anode, an organic light-emitting layer, and a cathode. OLEDs may also have various structures such as anode/hole injection layer/hole transport layer/emitting layer/electron transport layer/electron injection layer/cathode or anode/hole injection layer/hole transport layer/emitting layer/hole blocking layer/electron transport layer/electron injection layer/cathode.

Materials used for OLEDs can be classified into vacuum-depositable materials and solution-coatable materials according to an organic layer formation process. Vacuum-depositable materials must have a vapor pressure of $10^{-6}$ torr or more at 500° C. or less, and may be low molecular weight materials having a molecular weight of 1,200 or less. Solution-coatable materials must be highly soluble in solvents to form solutions, and include mainly an aromatic or heterocyclic ring.

When manufacturing organoelectroluminescent devices using a vacuum deposition process, manufacturing costs may increase due to use of a vacuum system, and it may be difficult to manufacture high-resolution pixels for natural color displays using a shadow mask. On the other hand, when manufacturing organoelectroluminescent devices using a solution coating process, e.g., inkjet printing, screen printing, or spin coating, the manufacturing process is simple, manufacturing costs are low, and a relatively high resolution can be achieved compared to when using a shadow mask.

However, when using solution-coatable materials, the performance (e.g., thermal stability, color purity) of light-emitting molecules is lowered compared to when using vacuum-depositable materials. Even though the light-emitting molecules of the solution-coatable materials have good performance, there arise problems that the materials, when formed into an organic layer, are gradually crystallized to grow into a size corresponding to a visible light wavelength range, and thus, the grown crystals scatter visible light, thereby causing a turbidity phenomenon, and pinholes, etc. may be formed in the organic layer, thereby causing device degradation.

Japanese Patent Laid-Open Publication No. 1999-003782 discloses a two naphthyl-substituted anthracene compound that can be used in an emitting layer or a hole injection layer. However, the anthracene compound is poorly soluble in a solvent, and further, an organoelectroluminescent device using the anthracene compound has unsatisfactory characteristics.

Therefore, it still needs to develop organoelectroluminescent devices having a lower driving voltage and improved brightness, efficiency, and color purity characteristics by virtue of light-emitting compounds having good thermal stability and being capable of forming good organic layers.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention provides a cyclopentaphenanthrene-based compound which is adapted for both dry and wet processes, and has excellent thermal stability and good charge transport and emission characteristics, and an organoelectroluminescent device employing the same.

According to an aspect of the present invention, there is provided a cyclopentaphenanthrene-based compound represented by Formula 1 below:

<Formula 1> wherein each Q is independently one of groups represented in Formulas 2A to 2R below:

2A

2B

2C

2D

2E

2F

2G

2H

2I

2J

2K

2L

2M

2N

2O

-continued

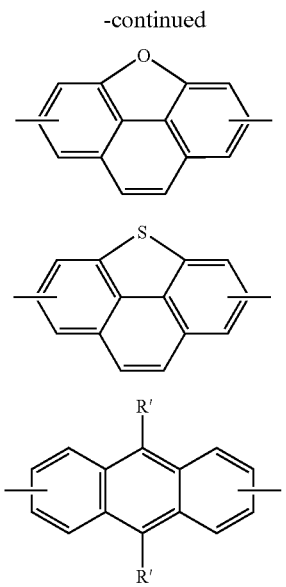

2P

2Q

2R wherein R' and R" are hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, $-N(Z_1)(Z_2)$ or $-Si(Z_3)(Z_4)(Z_5)$ where $Z_1, Z_2, Z_3, Z_4,$ and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

X is hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl, $-N(Z_1)(Z_2)$ or $-Si(Z_3)(Z_4)(Z_5)$ where $Z_1, Z_2, Z_3, Z_4,$ and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

m is an integer of 1 to 3, and when m is 2 or 3, Qs are the same or different from each other;

n is an integer of 0 to 3, and when n is 2 or 3, Ys are the same or different from each other;

$R_1$ and $R_2$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, a substituted or unsubstituted C2-C30 heteroaromatic ring;

$R_3$ through $R_8$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, $-N(Z_1)(Z_2)$ or $-Si(Z_3)(Z_4)(Z_5)$ where $Z_1, Z_2, Z_3, Z_4,$ and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and $R_{11}$ is hydrogen, halogen, a cyano group, a hydroxyl group, or a substituted or unsubstituted C1-C20 alkyl group.

In one embodiment, the

in Formula 1 may form one of rings represented by Formulae 3 through 6 below:

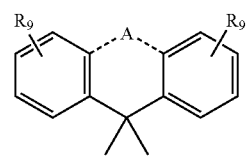

<Formula 3>

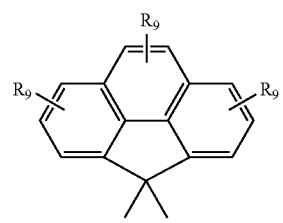

<Formula 4>

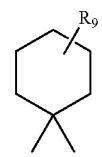

<Formula 5>

-continued

<Formula 6>
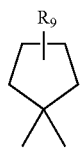

wherein each $R_9$ is independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N($Z_1$)($Z_2$) or —Si($Z_3$)($Z_4$)($Z_5$) where $Z_1, Z_2, Z_3, Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and A is a single bond, —O—, —S—, —Se—, or —$(CH_2)_p$— where p is an integer of 1 to 5.

According to an embodiment of the present invention, the compound of Formula 1 may be selected from compounds represented by Formulae 7 through 9 below:

<Formula 7>
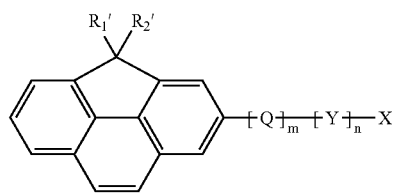

<Formula 8>
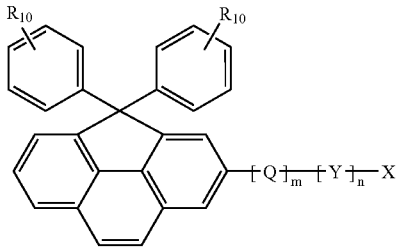

<Formula 9>
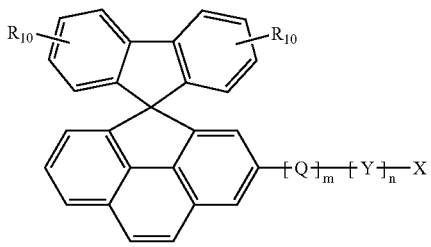

wherein each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

each Q is independently one of groups represented in Formulas 2A to 2R below:

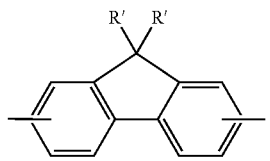
2A

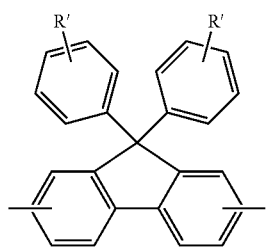
2B

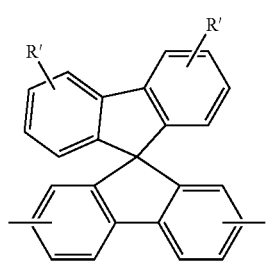
2C

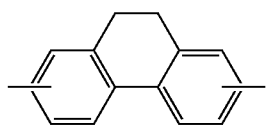
2D

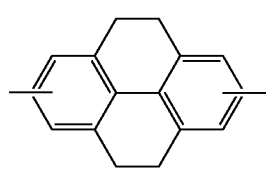
2E

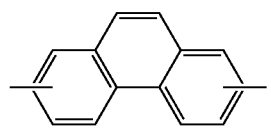
2F

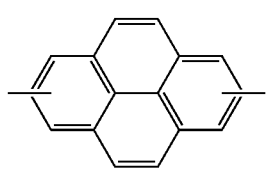
2G

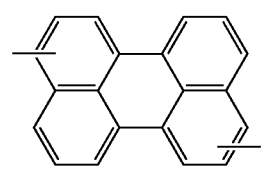
2H

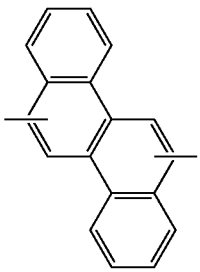
2I

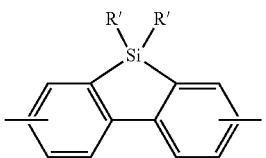
2J

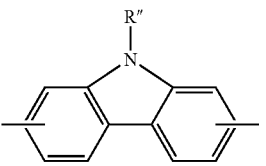
2K

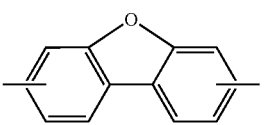
2L

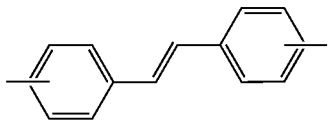
2M

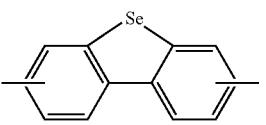
2N

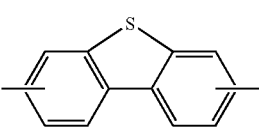
2O

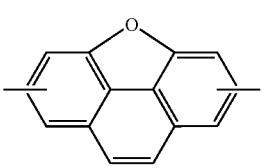
2P

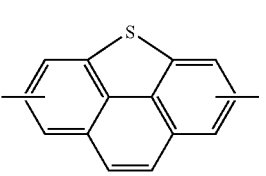
2Q

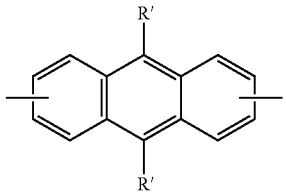
2R wherein R' and R" are hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, $-N(Z_1)(Z_2)$ or $-Si(Z_3)(Z_4)(Z_5)$ where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

m is an integer of 1 to 3, and when m is 2 or 3, "Q"s may be the same or different from each other;

n is an integer of 0 to 3, and when n is 2 or 3, "Y"s may be the same or different from each other;

X is hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, $-N(Z_1)(Z_2)$ or $-Si(Z_3)(Z_4)(Z_5)$ where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

$R_{10}$ is hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, $-N(Z_1)(Z_2)$ or $-Si(Z_3)(Z_4)(Z_5)$ where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and $R_1'$ and $R_2'$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group.

According to another aspect of the present invention, there is provided an organoelectroluminescent device including: a first electrode; a second electrode; and at least one organic layer interposed between the first electrode and the second electrode, the organic layer including the above-described organoelectroluminescent compound.

In the present invention, a low molecular weight compound obtained by reacting a cyclopentaphenanthrene compound, wherein the 2- or 6-position is functionalized, with another compound, is used as an organoelectroluminescent material. Various substituents can be incorporated into the 4-position of the cyclopentaphenanthrene of the low molecular weight compound, thereby enabling more stable film formation and improving solubility in a solvent.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
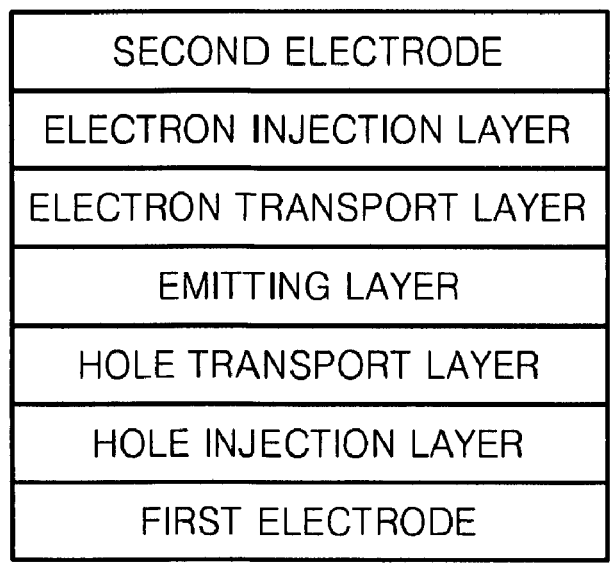
FIGS. 1A through 1C are schematic views illustrating organoelectroluminescent devices according to embodiments of the present invention.

Embodiments of the present invention will now be described more fully with reference to the accompanying drawings, in which exemplary embodiments of the invention are shown.

The present invention provides a cyclopentaphenanthrene-based compound represented by Formula 1 below:

<Formula 1>

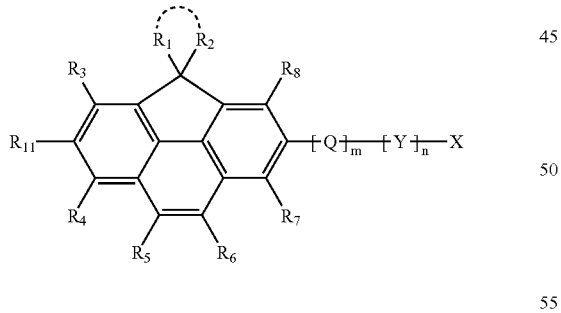

wherein each Q is independently one of groups represented in Formulas 2A to 2R below:

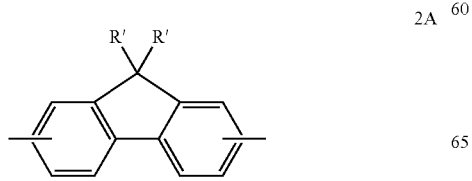  2A

-continued

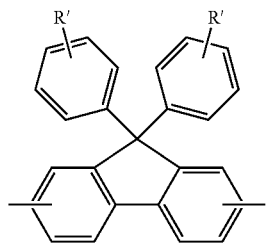  2B

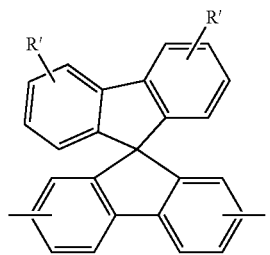  2C

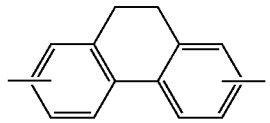  2D

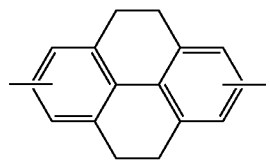  2E

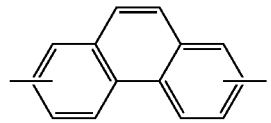  2F

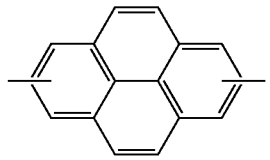  2G

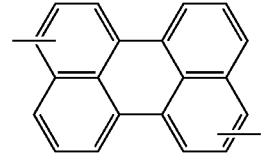  2H

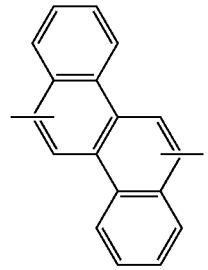  2I

-continued

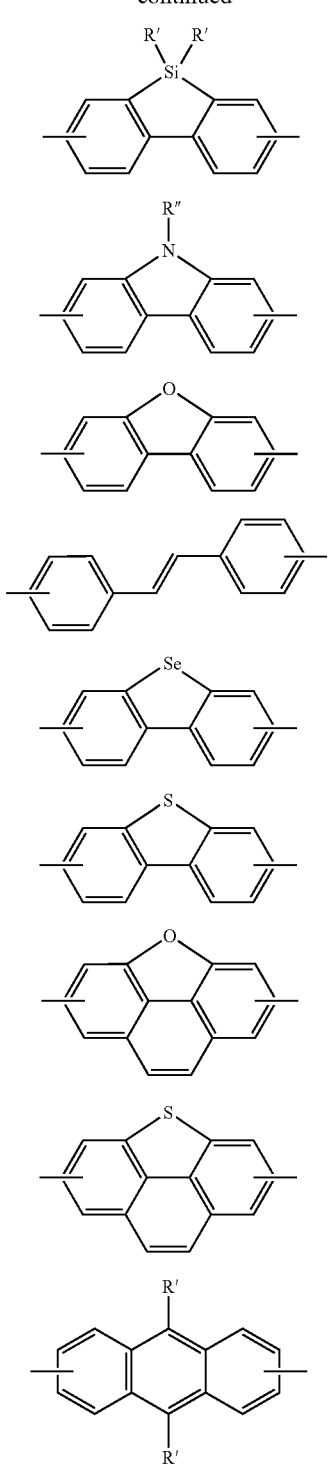

2J

2K

2L

2M

2N

2O

2P

2Q

2R wherein R' and R" are independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, $-N(Z_1)(Z_2)$ or $-Si(Z_3)(Z_4)(Z_5)$ where $Z_1, Z_2, Z_3, Z_4,$ and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

X is hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl, $-N(Z_1)(Z_2)$ or $-Si(Z_3)(Z_4)(Z_5)$ where $Z_1, Z_2, Z_3, Z_4,$ and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

m is an integer of 1 to 3, and when m is 2 or 3, Qs may be the same or different from each other;

n is an integer of 0 to 3, and when n is 2 or 3, Ys may be the same or different from each other; $R_1$ and $R_2$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, a substituted or unsubstituted C2-C30 heteroaromatic ring;

$R_3$ through $R_8$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, $-N(Z_1)(Z_2)$ or $-Si(Z_3)(Z_4)(Z_5)$ where $Z_1, Z_2, Z_3, Z_4,$ and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and $R_{11}$ is hydrogen, halogen, a cyano group, a hydroxyl group, or a substituted or unsubstituted C1-C20 alkyl group.

In the present application, when two or more are independently selected, it means that two or more may be the same or different from each other.

According to an embodiment, in Formula 1, m may be an integer of 1 or 2, and n may be an integer of 0 to 2.

According to an embodiment, the

in Formula 1 may form rings represented by Formulae 3 through 6 below:

<Formula 3>

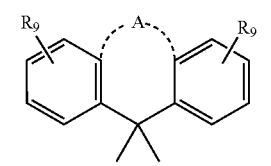

<Formula 4>

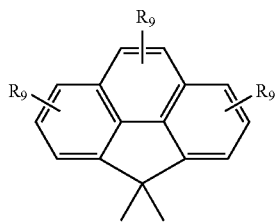

<Formula 5>

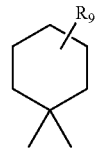

<Formula 6>

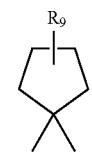

wherein $R_9$s are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and A is a single bond, —O—, —S—, —Se—, or —(CH$_2$)$_p$— where p is an integer of 1 to 5.

The compound of Formula 1 according to an embodiment of the present invention may be selected from compounds represented by Formulae 7 through 9:

<Formula 7>

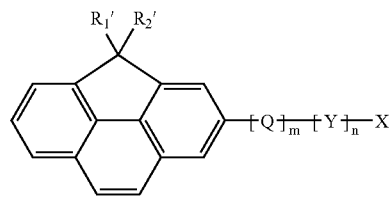

<Formula 8>

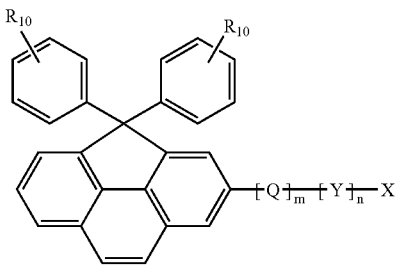

<Formula 9>

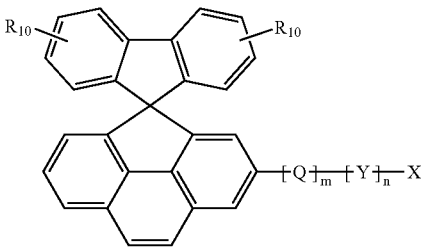

wherein each Q is independently one of groups represented in Formulas 2A to 2R below:

2A

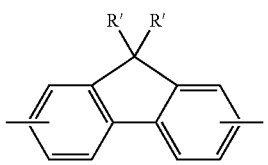

2B

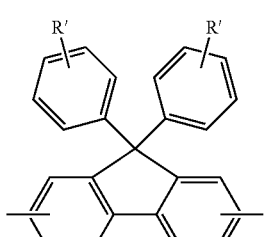

2C

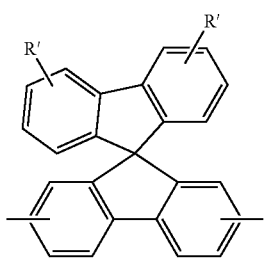

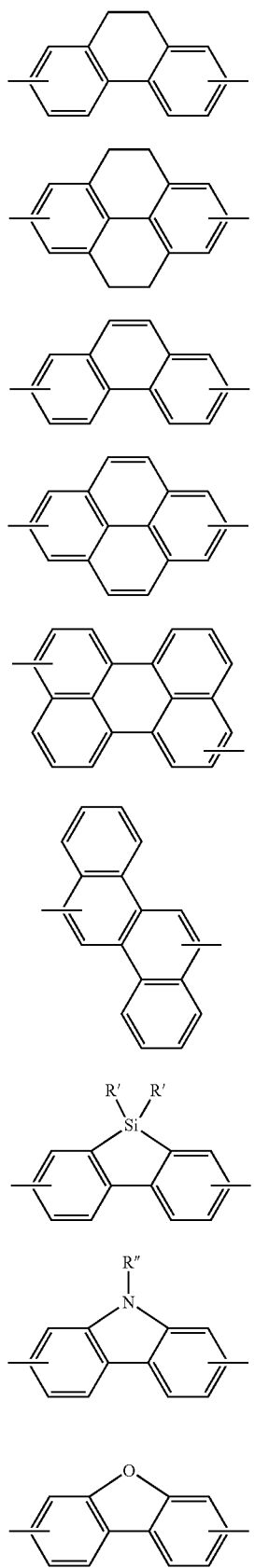

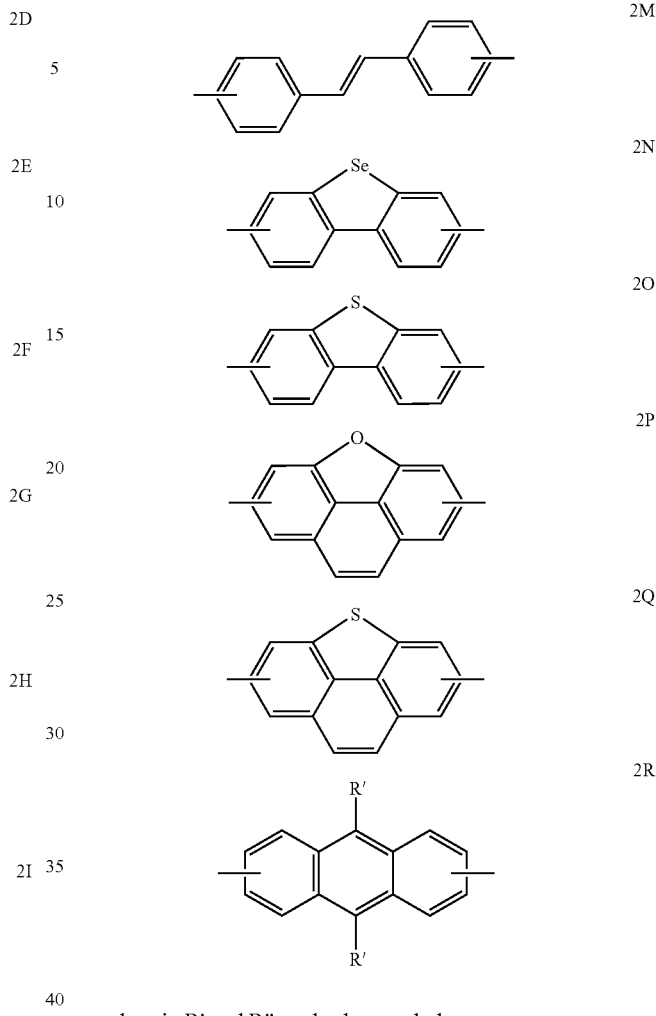

wherein R' and R" are hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

X is hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

m is an integer of 1 to 3, and when m is 2 or 3, Qs may be the same or different from each other;

n is an integer of 0 to 3, and when n is 2 or 3, Ys may be the same or different;

$R_{10}$s are the each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and $R_1'$ and $R_2'$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group.

According to an embodiment, in Formulae 7 through 9, m may be an integer of 1 or 2, and n may be an integer of 0 to 2.

According to an embodiment, in Formulae 7 through 9, —[Y]$_n$—X may be selected from groups represented in Formulae 10-1 through 10-116 below, but is not limited to:

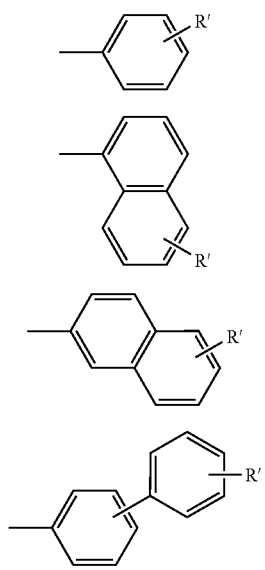

-continued

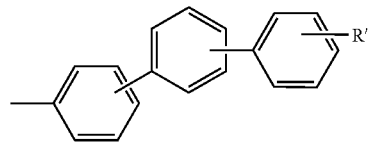
10-5

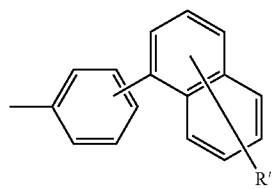
10-6

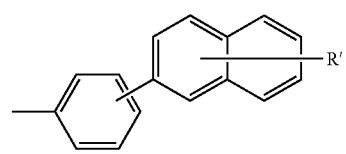
10-7

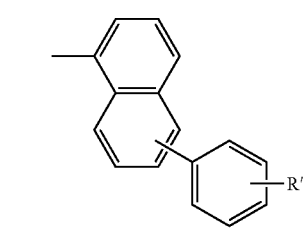
10-8

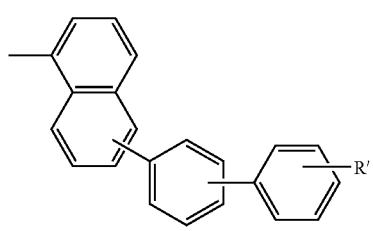
10-9

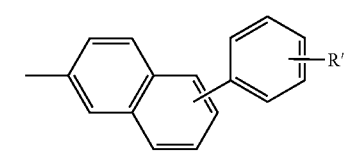
10-10

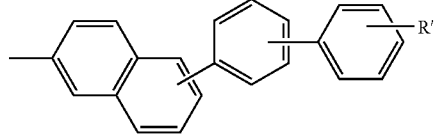
10-11

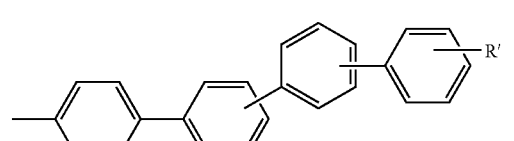
10-12

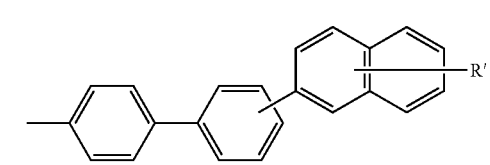
10-13

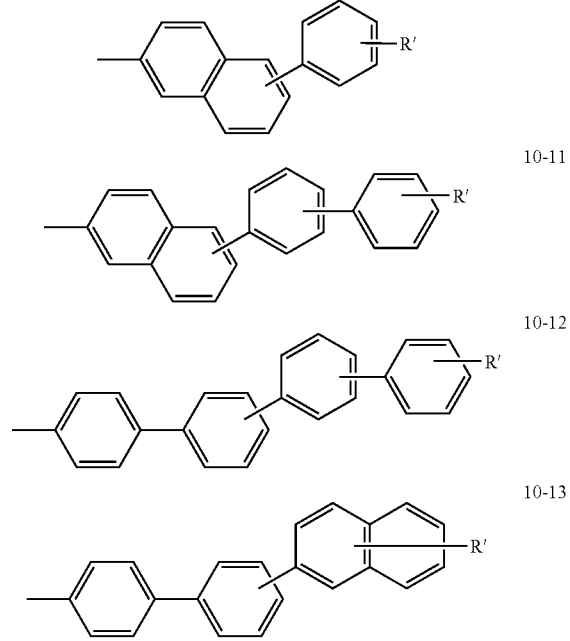

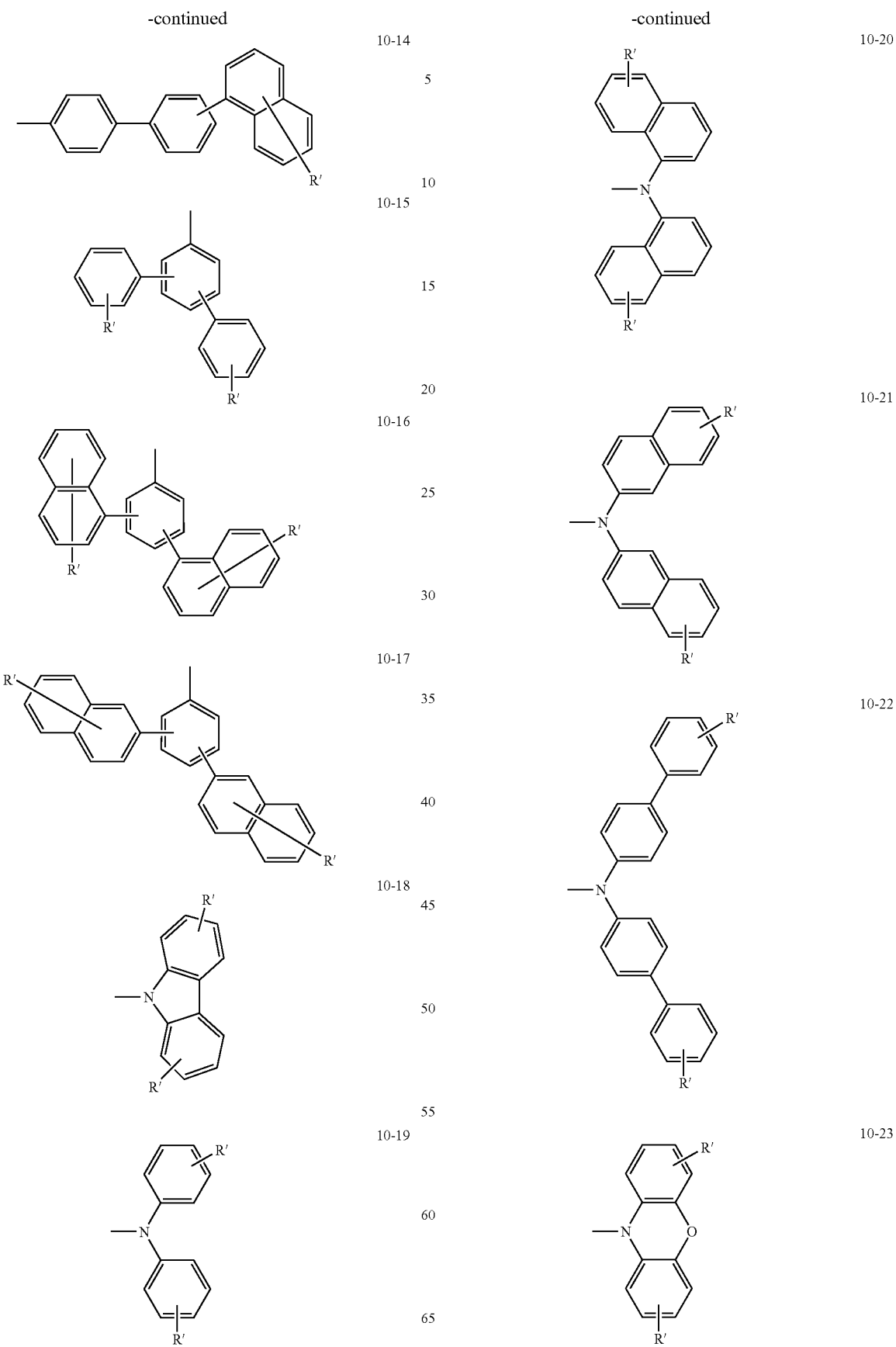

-continued
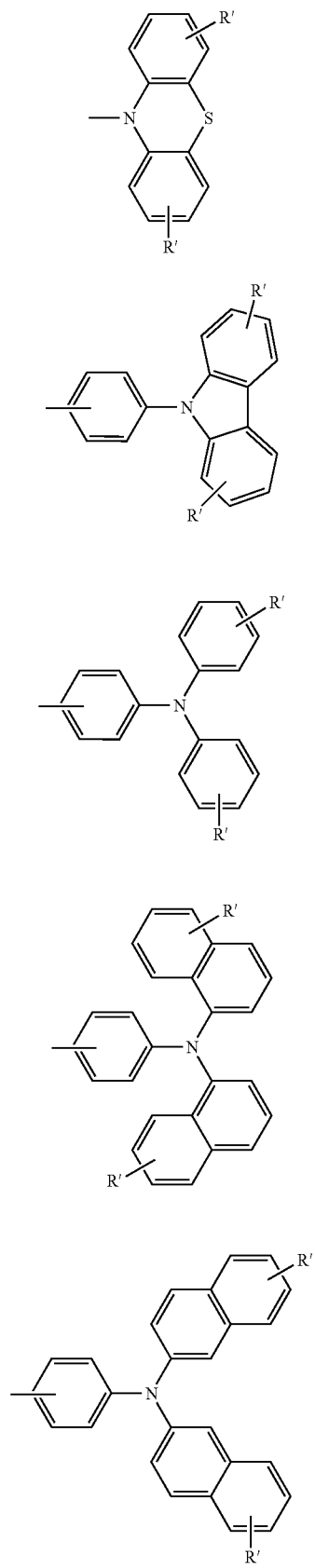
10-24
10-25
10-26
10-27
10-28
-continued
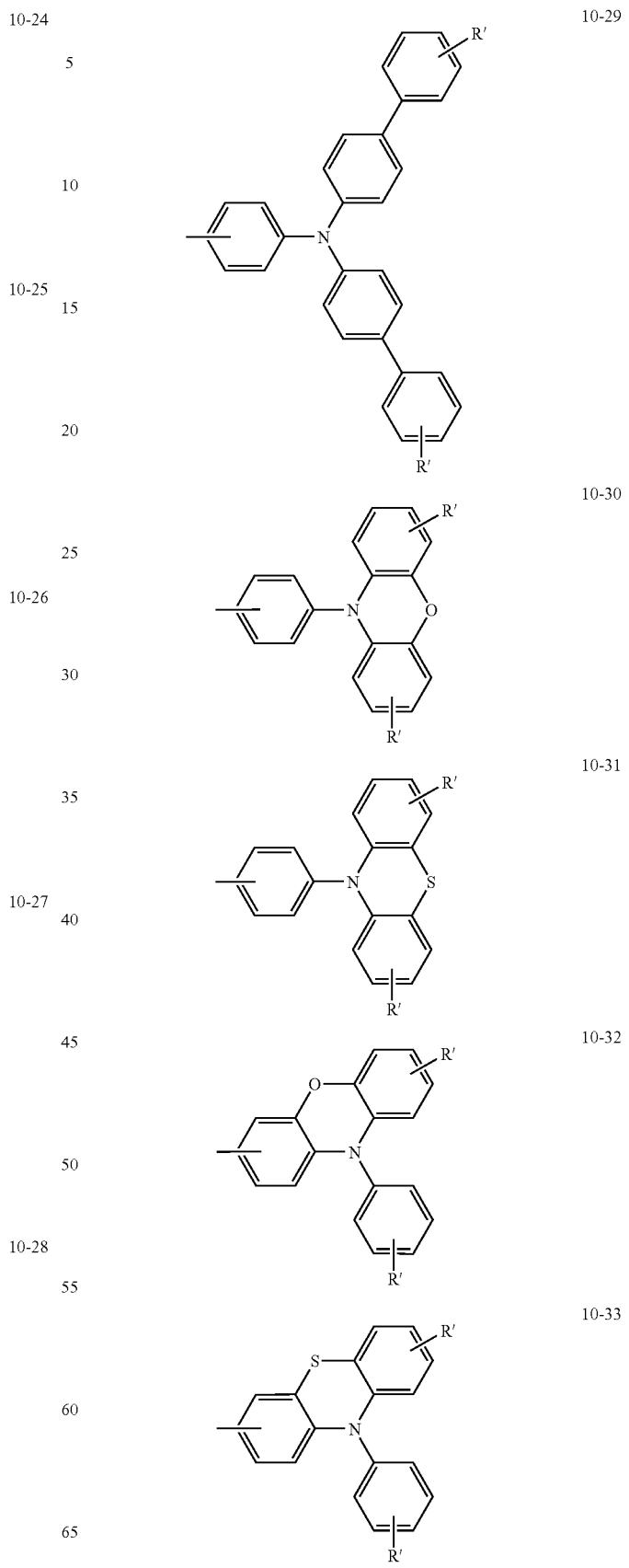
10-29
10-30
10-31
10-32
10-33

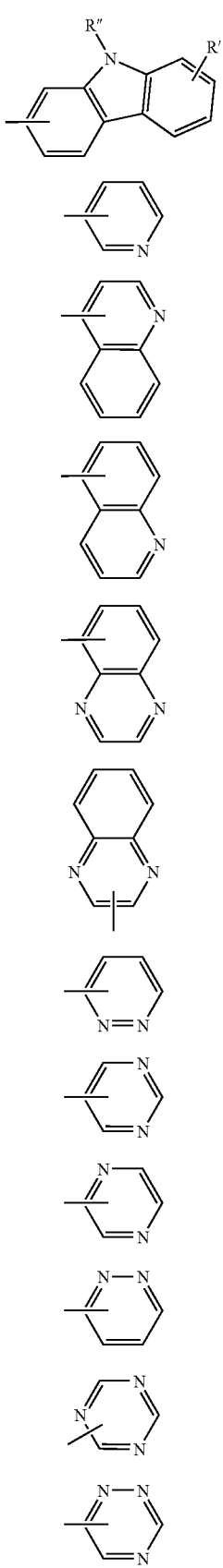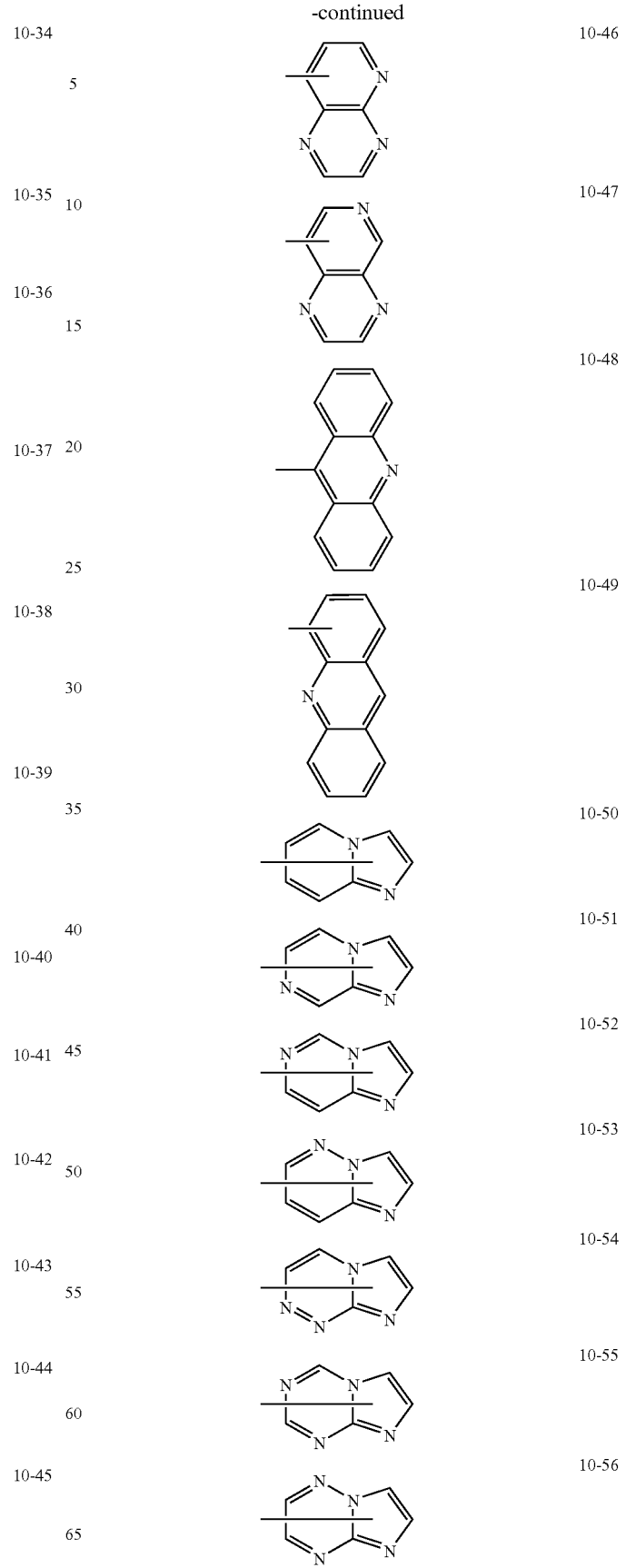

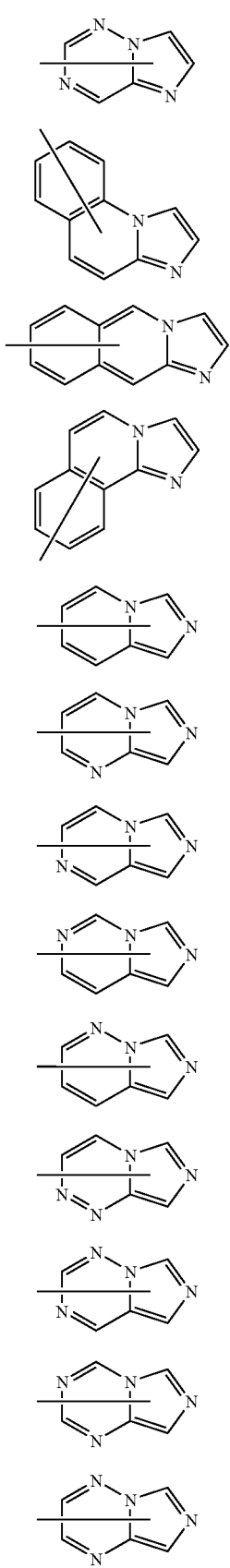
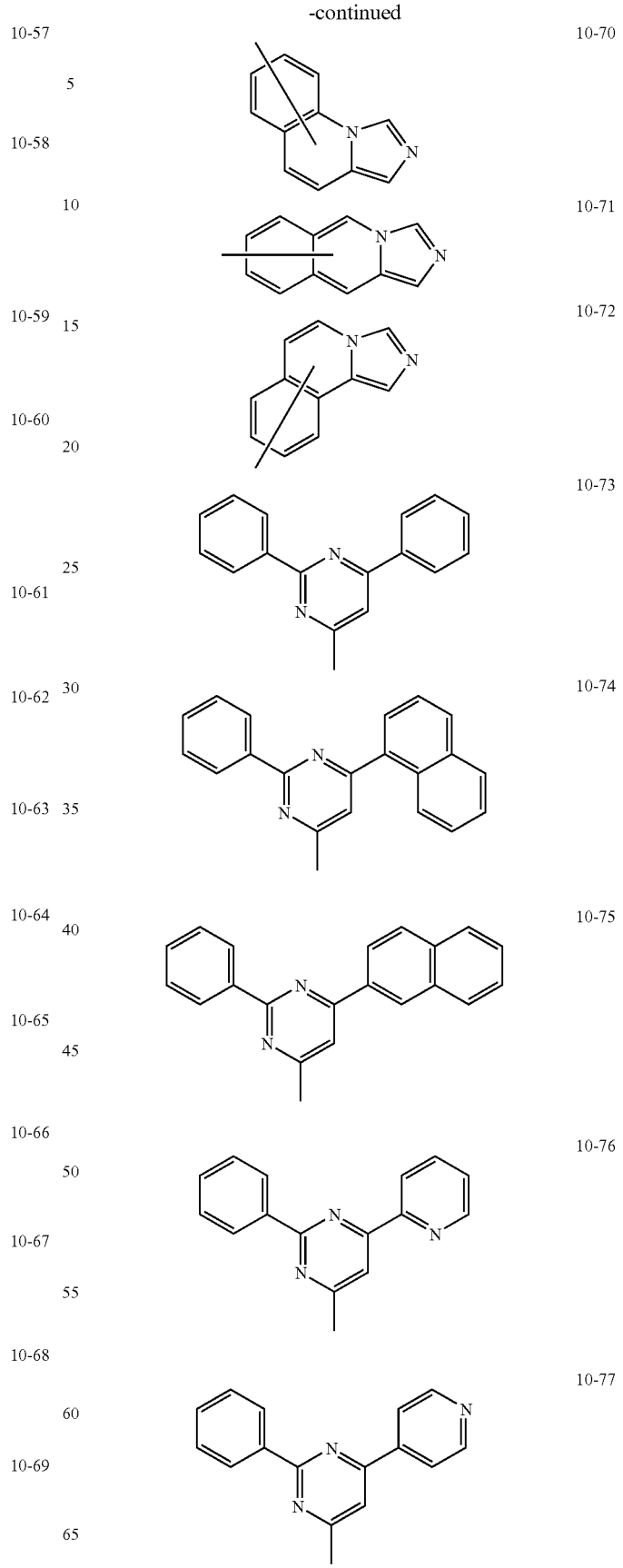

-continued 10-78
10-79
10-80
10-81
10-82
10-83
10-84
10-85

-continued 10-86
10-87
10-88
10-89
10-90
10-91
10-92
10-93
10-94
10-95
10-96

-continued

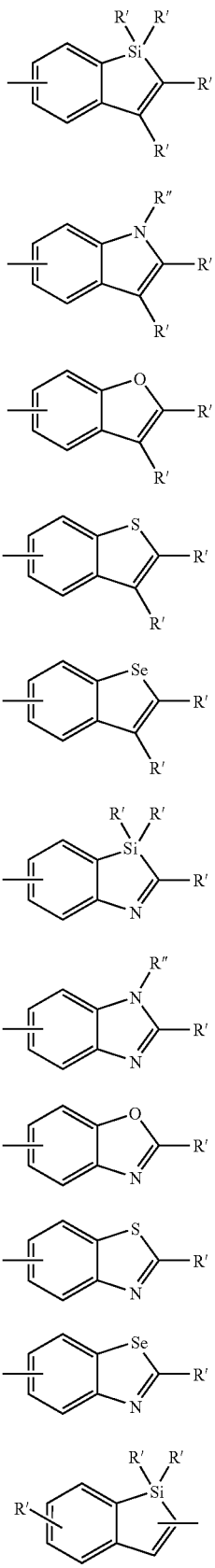

10-97
10-98
10-99
10-100
10-101
10-102
10-103
10-104
10-105
10-106
10-107

-continued

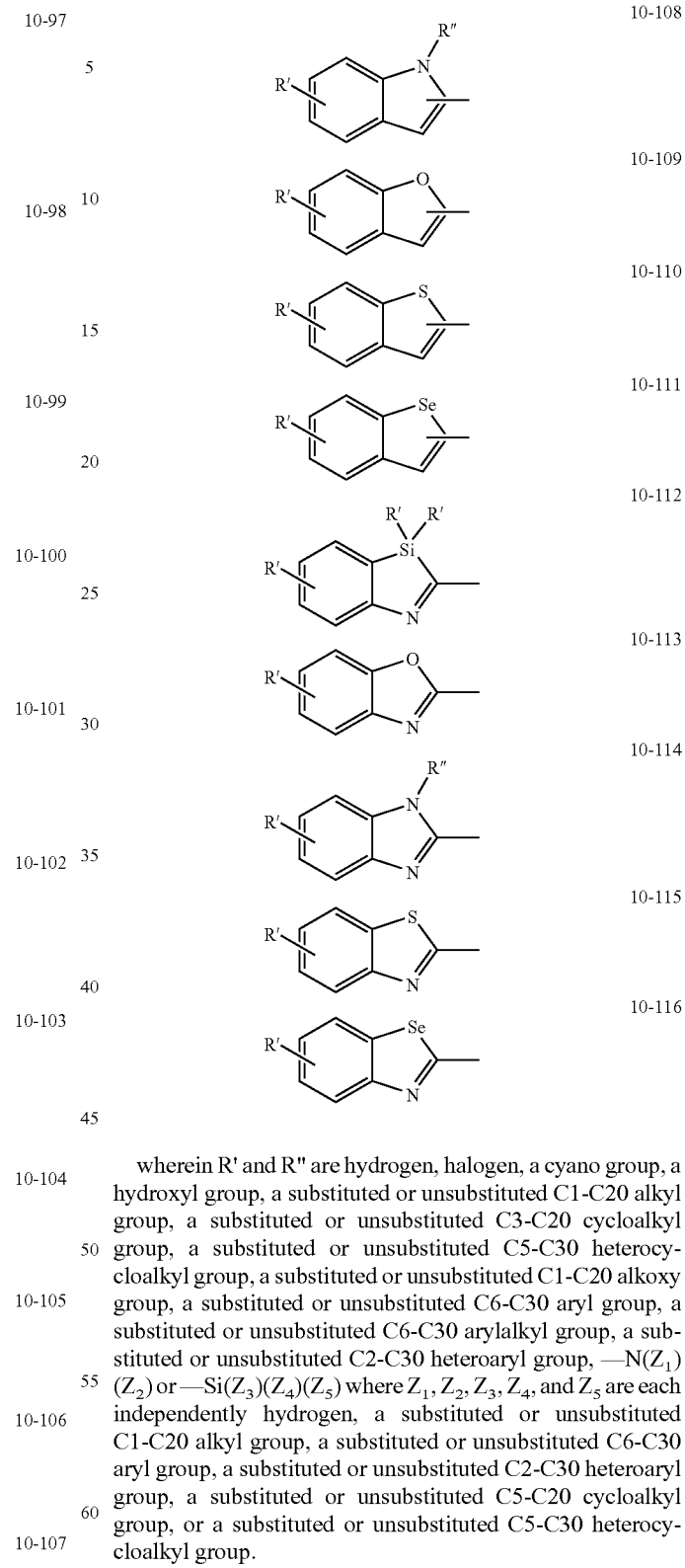

10-108
10-109
10-110
10-111
10-112
10-113
10-114
10-115
10-116 wherein R' and R" are hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group.

In the above formulae, the "aryl group" refers to a monovalent group having an aromatic ring system and may contain two or more ring systems as well as one ring system. The two or more ring systems may be attached or fused to each other. The "heteroaryl group" refers to an aryl group in which at least one carbon atom is substituted by at least one selected from the group consisting of N, O, S, and P.

The "cycloalkyl group" refers to an alkyl group having a ring system, and the "heterocycloalkyl group" refers to a cycloalkyl group in which at least one carbon atom is substituted by at least one selected from the group consisting of N, O, S, and P.

In the above formulae, the alkyl group, the alkoxy group, the aryl group, the heteroaryl group, the cycloalkyl group, and the heterocycloalkyl group may be substituted by at least one substituent selected from the group consisting of —F; —Cl; —Br; —CN; —NO$_2$; —OH; a C1-C20 alkyl group which is unsubstituted or substituted by —F, —Cl, —Br, —CN, —NO$_2$, or —OH; a C1-C20 alkoxy group which is unsubstituted or substituted by —F, —Cl, —Br, —CN, —NO$_2$, or —OH; a C6-C30 aryl group which is unsubstituted or substituted by a C1-C20 alkyl group, a C1-C20 alkoxy group, —F, —Cl, —Br, —CN, —NO$_2$, or —OH; a C2-C30 heteroaryl group which is unsubstituted or substituted by a C1-C20 alkyl group, a C1-C20 alkoxy group, —F, —Cl, —Br, —CN, —NO$_2$, or —OH; a C5-C20 cycloalkyl group which is unsubstituted or substituted by a C1-C20 alkyl group, a C1-C20 alkoxy group, —F, —Cl, —Br, —CN, —NO$_2$, or —OH; a C5-C30 heterocycloalkyl group which is unsubstituted or substituted by a C1-C20 alkyl group, a C1-C20 alkoxy group, —F, —Cl, —Br, —CN, —NO$_2$, or —OH; and a group represented by —N(G$_6$)(G$_7$) where G$_6$ and G$_7$ are each independently hydrogen; a C1-C10 alkyl group; or a C6-C30 aryl group which is substituted by a C1-C10 alkyl group.

In more detail, R$_1$ through R$_8$ are each independently selected from the group consisting of hydrogen, halogen, a cyano group, a hydroxyl group, a C1-C10 alkyl group, a C1-C10 alkoxy group, and a substituted or unsubstituted group as follows: a phenyl group, a biphenyl group, a pentalenyl group, an indenyl group, a naphthyl group, a biphenylenyl, an anthracenyl group, an azulenyl group, a heptalenyl group, an acenaphthylenyl group, a phenalenyl group, a fluorenyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, an oxiranyl group, a pyrrolidinyl group, a pyrazolidinyl group, an imidazolidinyl group, a piperidinyl group, a piperazinyl group, a morpholinyl group, a di(C6-C30 aryl)amino group, a tri(C6-C30 aryl)silyl group, and derivatives thereof.

As used herein, the term "derivative(s)" refers to the above-illustrated group(s) wherein at least one hydrogen is substituted by a substituent as described above.

A compound according to an embodiment of the present invention may be selected from the group consisting of compounds represented by Formulae 15 through 43, but is not limited to:

<Formula 15>

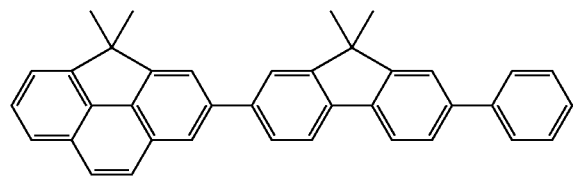

<Formula 16>

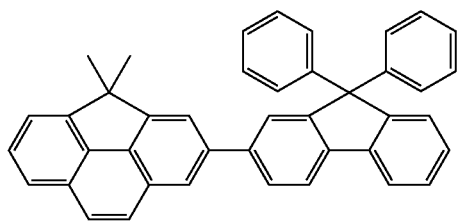

<Formula 17>

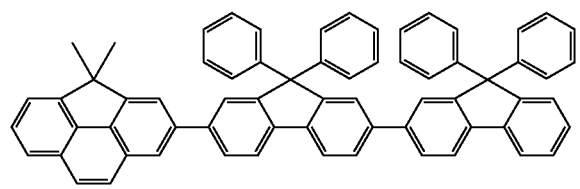

<Formula 18>

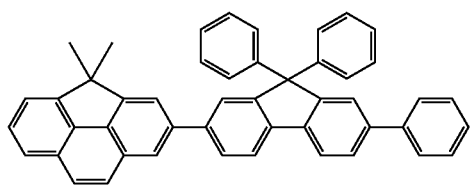

<Formula 19>

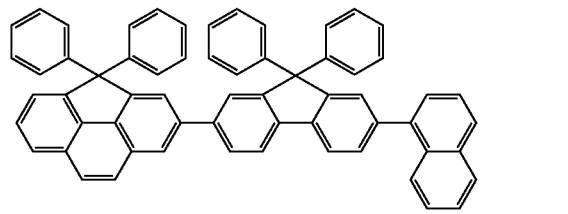

<Formula 20>

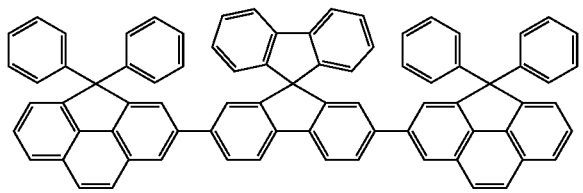

-continued
<Formula 21>
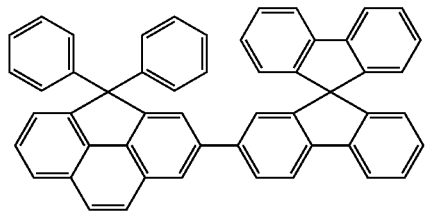
<Formula 22>
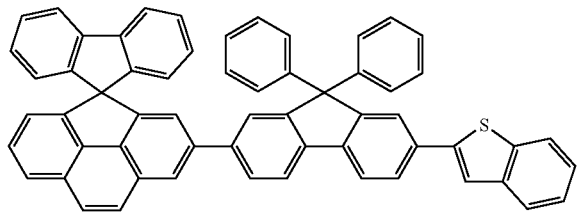
<Formula 23>
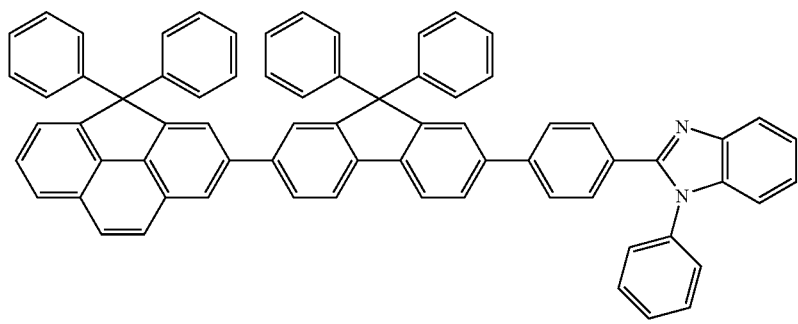
<Formula 24>
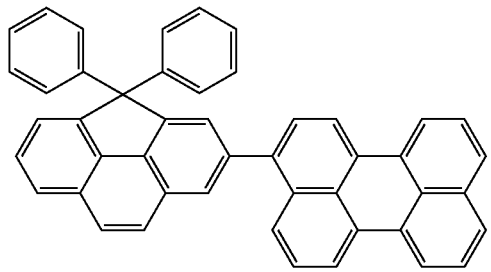
<Formula 25>
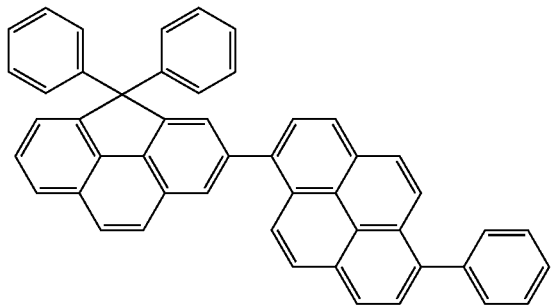
<Formula 26>
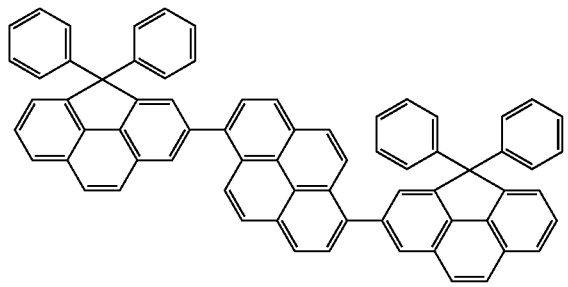
<Formula 27>
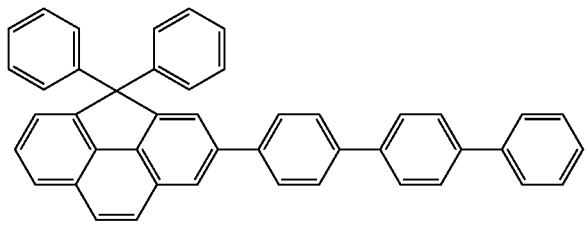
<Formula 28>
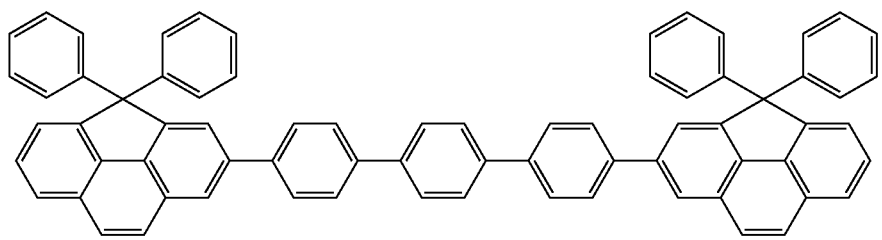

-continued
<Formula 29>
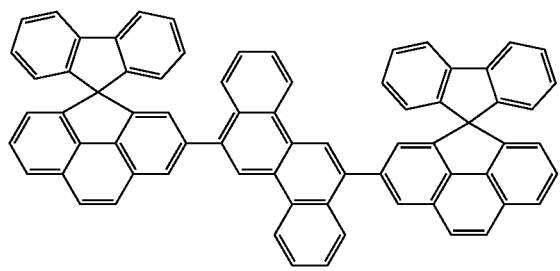
<Formula 30>
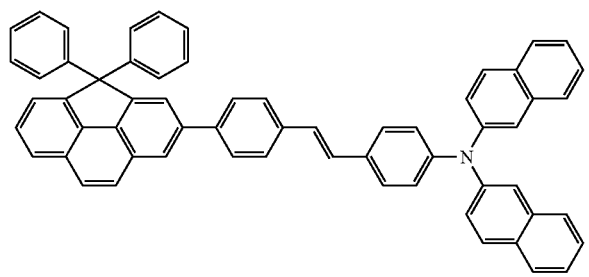
<Formula 31>
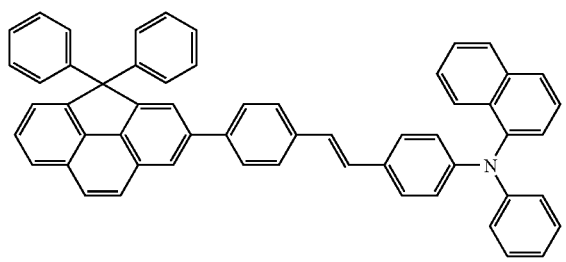
<Formula 32>
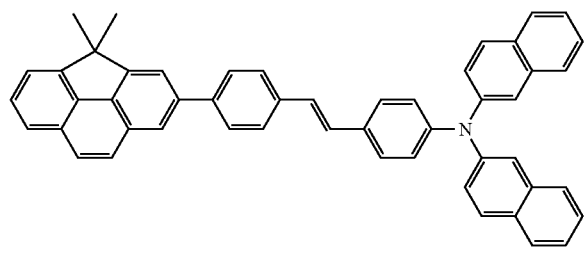
<Formula 33>
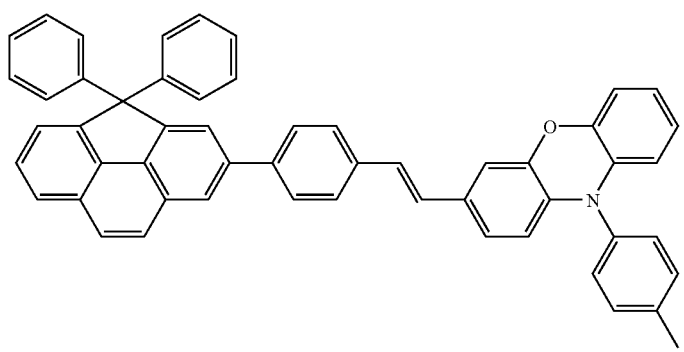
<Formula 34>
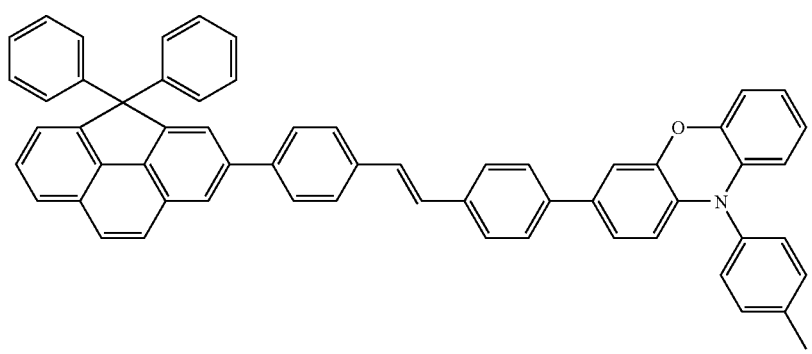
<Formula 35>
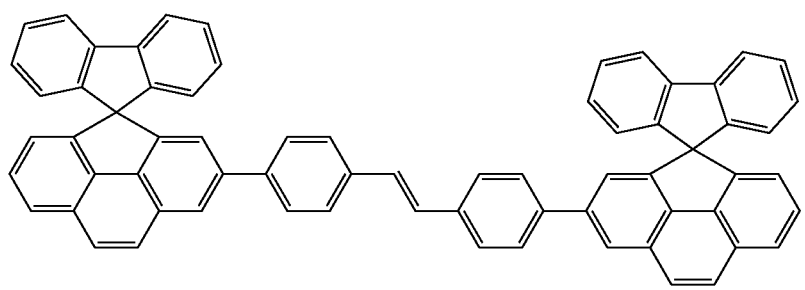

-continued
<Formula 36>
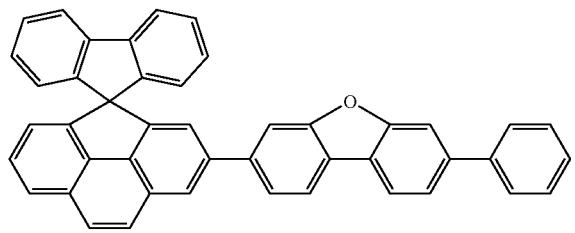
<Formula 37>
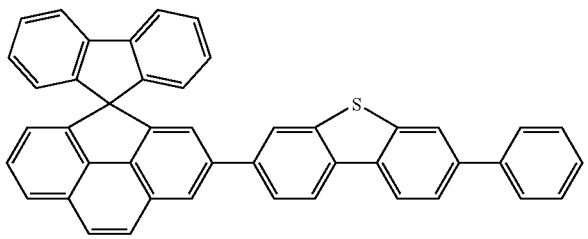
<Formula 38>
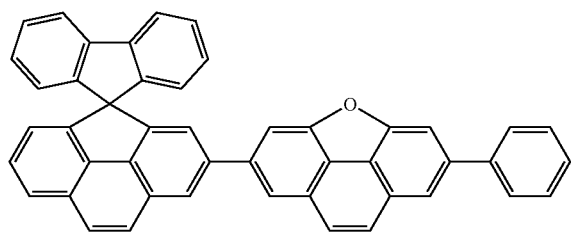
<Formula 39>
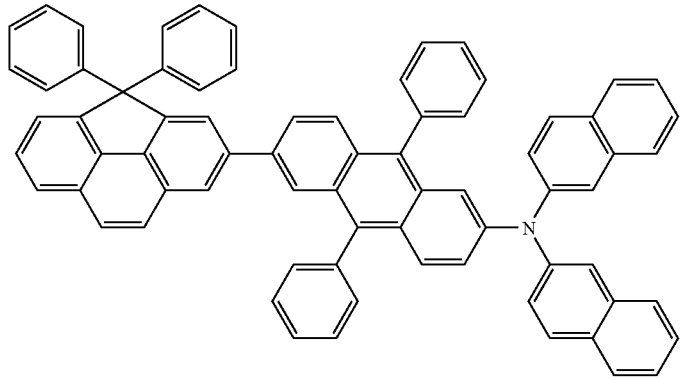
<Formula 40>
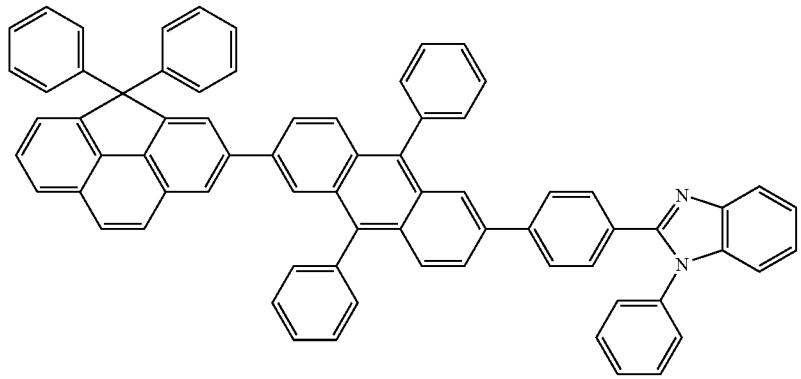
<Formula 41>
<Formula 42>
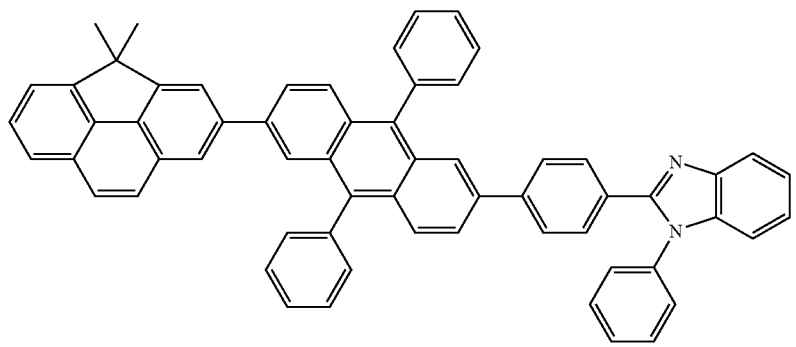

<Formula 43>

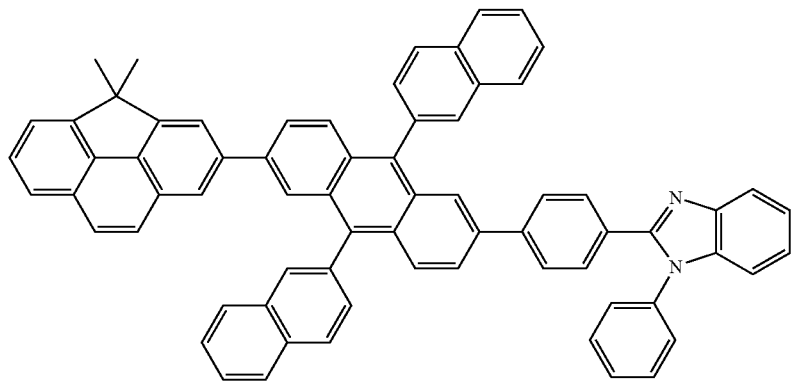

A compound as represented by Formula 1 according to an embodiment of the present invention can be synthesized using a common synthesis method. For a detailed synthesis procedure of the compound of the present invention, reference will be made to the reaction schemes in the following synthesis examples.

The present invention also provides an organoelectroluminescent device including a first electrode, a second electrode, and an organic layer interposed between the first electrode and the second electrode, the organic layer including at least one compound represented by Formula 1 above.

The compound of Formula 1 is suitable for an organic layer of an organoelectroluminescent device, in particular an emitting layer, a hole injection layer, or a hole transport layer.

The organoelectroluminescent device according to an embodiment of the present invention includes a compound which has good solubility and thermal stability and can form a stable organic layer, and thus, can show a good driving voltage and enhanced emission characteristics (e.g., color purity), unlike a conventional organoelectroluminescent device including a less stable organic layer when manufactured using a solution coating process.

The organoelectroluminescent device according to an embodiment of the present invention can be variously structured. That is, the organoelectroluminescent device may further include at least one layer selected from the group consisting of a hole injection layer, a hole transport layer, a hole blocking layer, an electron blocking layer, an electron transport layer, and an electron injection layer, between the first electrode and the second electrode.

Figure 1B:
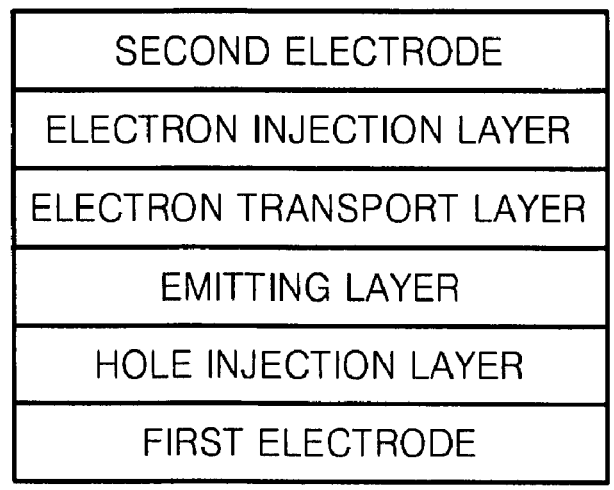
Figure 1C:
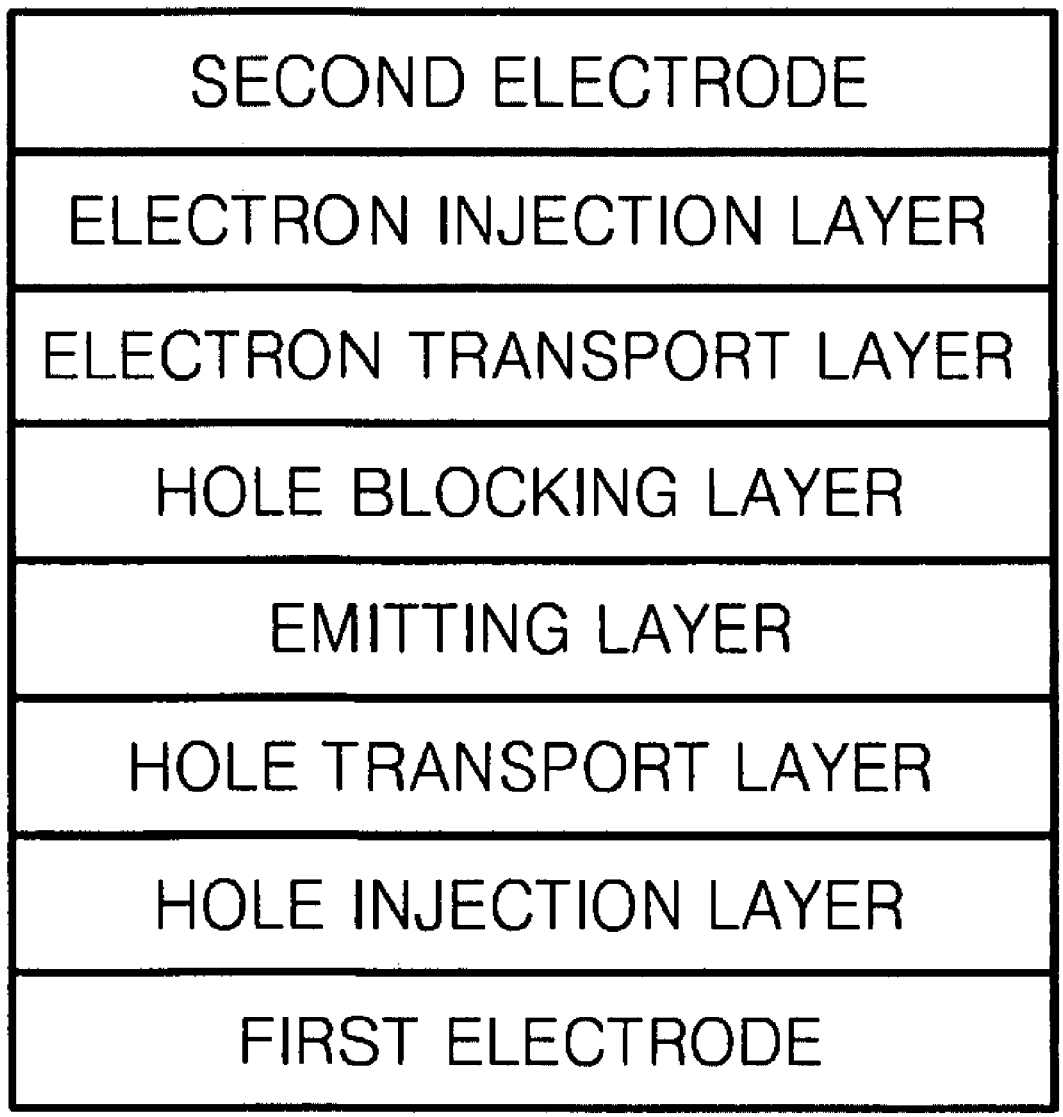

In more detail, organoelectroluminescent devices according to embodiments of the present invention are illustrated in FIGS. 1A, 1B, and 1C. Referring to FIG. 1A, an organoelectroluminescent device has a stacked structure of first electrode/hole injection layer/hole transport layer/emitting layer/electron transport layer/electron injection layer/second electrode. Referring to FIG. 1B, an organoelectroluminescent device has a stacked structure of first electrode/hole injection layer/emitting layer/electron transport layer/electron injection layer/second electrode. Referring to FIG. 1C, an organoelectroluminescent device has a stacked structure of first electrode/hole injection layer/hole transport layer/emitting layer/hole blocking layer/electron transport layer/electron injection layer/second electrode. Here, at least one of the emitting layer, the hole injection layer, and the hole transport layer may include a compound according to an embodiment of the present invention.

An emitting layer of the organoelectroluminescent device according to an embodiment of the present invention may include a red, green, blue, or white phosphorescent or fluorescent dopant. The phosphorescent dopant may be an organometallic compound including at least one element selected from the group consisting of Ir, Pt, Os, Ti, Zr, Hf, Eu, Tb, and Tm.

Hereinafter, a method of manufacturing an organoelectroluminescent device according to an embodiment of the present invention will be described with reference to FIG. 1C.

First, a first electrode is formed on a substrate by a deposition or sputtering process using a first electrode material with a high work function. The first electrode may be an anode. Here, the substrate may be a substrate commonly used in organoelectroluminescent devices. Preferably, the substrate may be a glass or transparent plastic substrate which is excellent in mechanical strength, thermal stability, transparency, surface smoothness, handling property, and water repellency. The first electrode material may be a material with transparency and good conductivity, e.g., indium tin oxide (ITO), indium zinc oxide (IZO), tin oxide ($SnO_2$), or zinc oxide (ZnO).

Next, a hole injection layer (HIL) may be formed on the first electrode using various methods such as vacuum deposition, spin-coating, casting, or Langmuir-Blodgett (LB) method.

In the case of forming the hole injection layer using a vacuum deposition process, the deposition conditions vary according to the type of a hole injection layer material, the structure and thermal characteristics of the hole injection layer, etc. However, it is preferred that the hole injection layer should be deposited to a thickness of 10 Å to 5 μm at a deposition rate of 0.01 to 100 Å/sec, at a temperature of 100 to 500° C., in a vacuum level of $10^{-8}$ to $10^{-3}$ torr.

In the case of forming the hole injection layer using a spin-coating process, the coating conditions vary according to the type of a hole injection layer material, the structure and thermal characteristics of the hole injection layer, etc. However, it is preferred that the spin-coating should be performed at a coating speed of about 2,000 to 5,000 rpm, and, after the spin-coating, a thermal treatment should be performed at a temperature of about 80 to 200° C. for the purpose of solvent removal.

The hole injection layer material may be a compound of Formula 1 as described above. In addition, the hole injection layer material may be a known hole injection material, e.g., a phthalocyanine compound (e.g., copper phthalocyanine) disclosed in U.S. Pat. No. 4,356,429 which is incorporated herein by reference, a Starburst-type amine derivative (e.g., TCTA, m-MTDATA, or m-MTDAPB) disclosed in *Advanced Material*, 6, p. 677 (1994) which is incorporated herein by reference, or a soluble conductive polymer, e.g., polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), or polyaniline/poly(4-styrenesulfonate) (PANI/PSS).

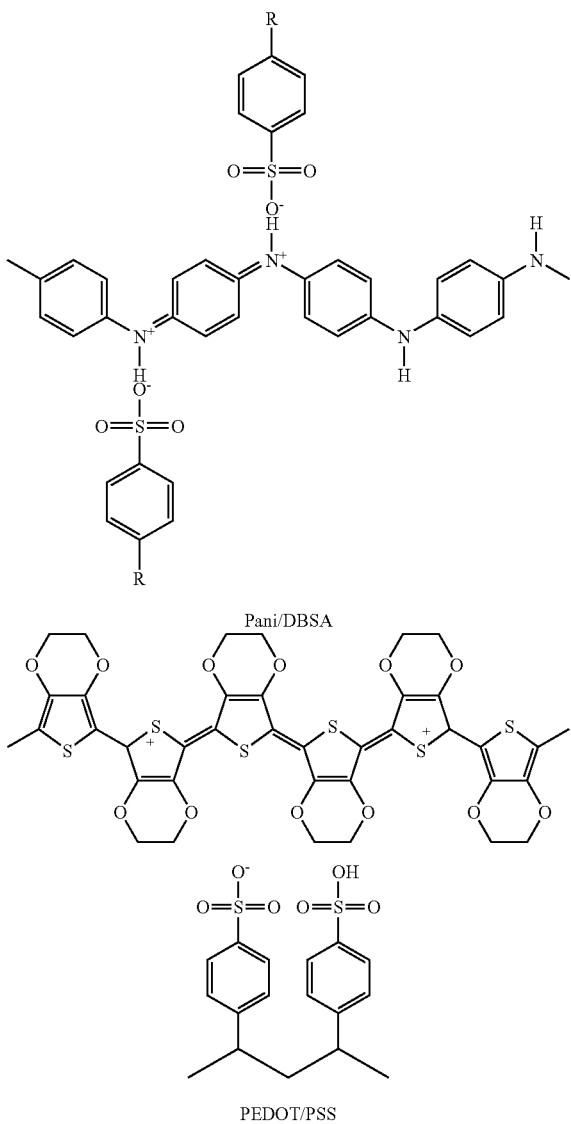

Pani/DBSA

PEDOT/PSS

The hole injection layer may be formed to a thickness of about 100 to 10,000 Å, preferably 100 to 1,000 Å. If the thickness of the hole injection layer is less than 100 Å, hole injection characteristics may be lowered. On the other hand, if the thickness of the hole injection layer exceeds 10,000 Å, a driving voltage may be increased.

Next, a hole transport layer (HTL) may be formed on the hole injection layer using various methods such as vacuum deposition, spin-coating, casting, or LB method. In the case of forming the hole transport layer using vacuum deposition or spin-coating, the deposition or coating conditions vary according to the type of a used compound, but are generally almost the same as those for the formation of the hole injection layer.

A hole transport layer material may be a compound of Formula 1 as described above. In addition, the hole transport layer material can be a known hole transport material, e.g., a carbazole derivative such as N-phenylcarbazole or polyvinylcarbazole; an amine derivative having an aromatic fused ring such as N,N'-bis(3-methylphenyl)-N,N'-diphenyl-[1,1-biphenyl]-4,4'-diamine (TPD) or N,N'-di(naphthalene-1-yl)-N,N'-diphenylbenzidine (α-NPD), etc.

The hole transport layer may be formed to a thickness of about 50 to 1,000 Å, preferably 100 to 600 Å. If the thickness of the hole transport layer is less than 100 Å, hole transport characteristics may be lowered. On the other hand, if the thickness of the hole transport layer exceeds 1,000 Å, a driving voltage may be increased.

Next, an emitting layer (EML) may be formed on the hole transport layer using vacuum deposition, spin-coating, casting, or LB method. In the case of forming the emitting layer using vacuum deposition or spin-coating, the deposition or coating conditions vary according to the type of a used compound, but are generally almost the same as those for the formation of the hole injection layer.

The emitting layer may include a compound of Formula 1 as described above. Here, a known fluorescent host material suitable for the compound of Formula 1 or a known dopant material may also be used. The compound of Formula 1 may be used as a phosphorescent host alone or in combination with 4,4'-N,N'-dicarbazole-biphenyl (CBP), poly(n-vinylcarbazole) (PVK), etc. As a phosphorescent dopant, there may be used a red phosphorescent dopant (e.g., PtOEP, RD 61 (UDC)), a green phosphorescent dopant (e.g., Ir(PPy)$_3$ (PPy=2-phenylpyridine)), or a blue phosphorescent dopant (e.g., F$_2$Irpic).

When the compound of Formula 1 is used as a dopant, the doping concentration of the dopant is not particularly limited. Generally, the content of the dopant is 0.01 to 15 parts by weight based on 100 parts by weight of a host. When the compound of Formula 1 is used as a single host, the doping concentration of a dopant is not particularly limited. Generally, the content of a dopant is 0.01 to 15 parts by weight based on 100 parts by weight of the host. When the compound of Formula 1 is used as a host in combination with another host, the content of the compound of Formula 1 is 30-99 parts by weight based on the total weight (100 parts by weight) of the hosts.

The emitting layer may be formed to a thickness of about 100 to 1,000 Å, preferably 200 to 600 Å. If the thickness of the emitting layer is less than 100 Å, emission characteristics may be lowered. On the other hand, if the thickness of the emitting layer exceeds 1,000 Å, a driving voltage may be increased.

In a case where the emitting layer includes a phosphorescent dopant, a hole blocking layer (HBL) may be formed on the emitting layer using vacuum deposition, spin-coating, casting, or LB method, in order to prevent the diffusion of triplet excitons or holes into an electron transport layer. In the case of forming the hole blocking layer using vacuum deposition or spin coating, the deposition or coating conditions vary according to the type of a used compound, but are generally almost the same as those for the formation of the hole injection layer. An available hole blocking material may be an oxadiazole derivative, a triazole derivative, a phenanthroline derivative, BCP, an aluminum complex, etc.

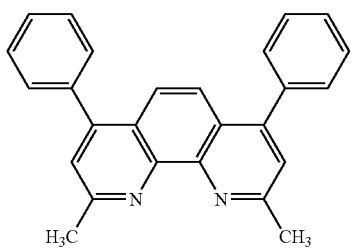

Phenanthroline-Containing Organic Compound

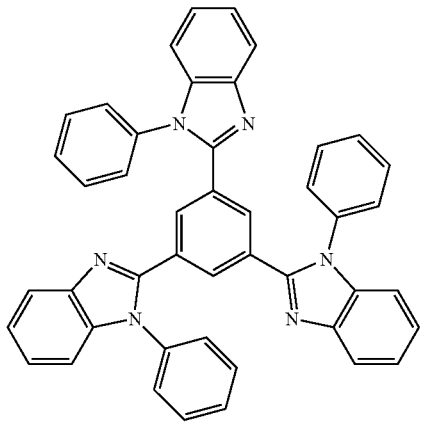

Imidazole-Containing Organic Compound

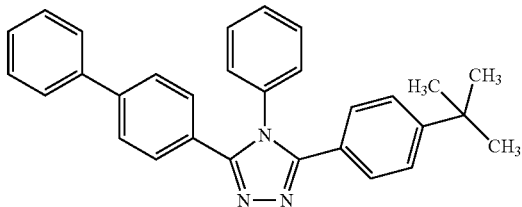

Triazole-Containing Organic Compound

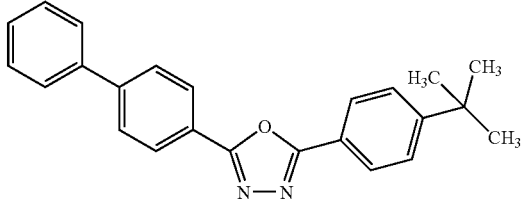

Oxadiazole-Containing Compound

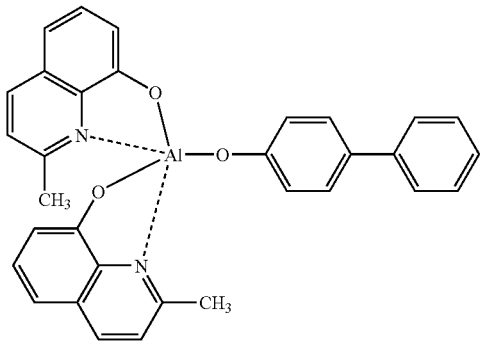

BAlq

The hole blocking layer may be formed to a thickness of about 50 to 1,000 Å, preferably 100 to 300 Å. If the thickness of the hole blocking layer is less than 50 Å, hole blocking characteristics may be lowered. On the other hand, if the thickness of the hole blocking layer exceeds 1,000 Å, a driving voltage may be increased.

Next, an electron transport layer (ETL) may be formed using various methods such as vacuum deposition, spin-coating, or casting. In the case of forming the electron transport layer using vacuum deposition or spin-coating, the deposition or coating conditions vary according to the type of a used compound, but are generally almost the same as those for the formation of the hole injection layer. An electron transport layer material serves to stably transport electrons from an electron donor electrode (a cathode) and may be a known material such as an oxazole-based compound, an isoxazole-based compound, a triazole-based compound, an isothiazole-based compound, an oxadiazole-based compound, a thiadiazole-based compound, a perylene-based compound, an aluminum complex (e.g.: Alq3 (tris(8-quinolinolato)-aluminum), BAlq, SAlq, or Almq3), a gallium complex (e.g.: Gaq'2OPiv, Gaq'2OAc, 2(Gaq'2)), etc.

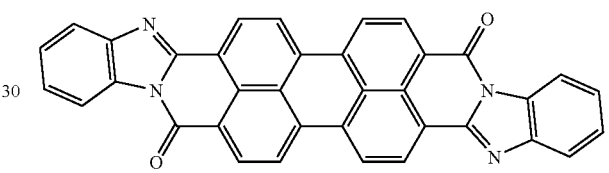

Perylene-Based Compound

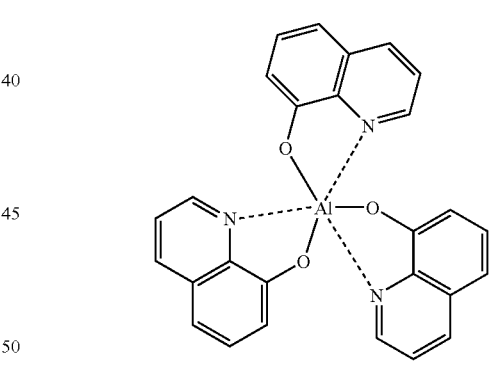

Alq3

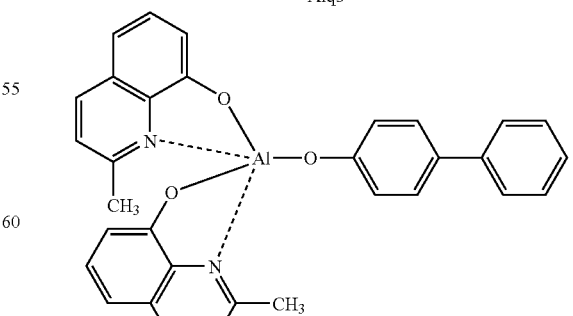

Balq

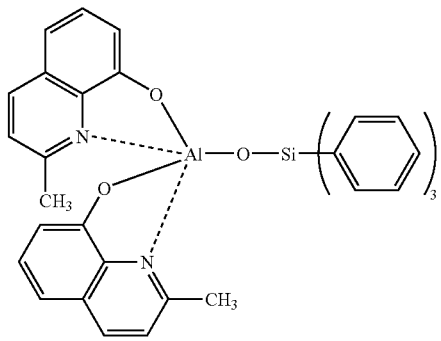

SAlq

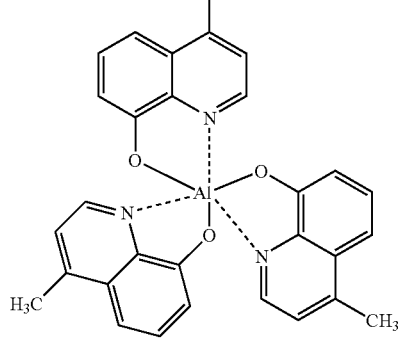

Almq3

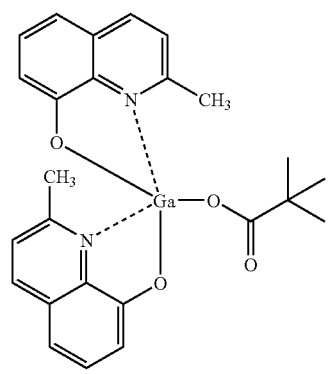

Gaq'2OPiv

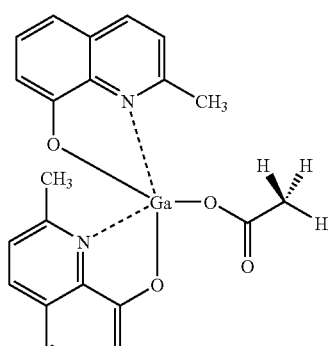

Gaq'2Oac

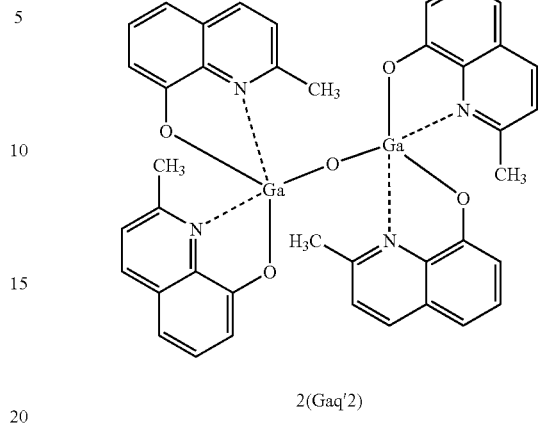

2(Gaq'2)

The electron transport layer may be formed to a thickness of about 100 to 1,000 Å, preferably 200 to 500 Å. If the thickness of the electron transport layer is less than 100 Å, electron transport characteristics may be lowered. On the other hand, if the thickness of the electron transport layer exceeds 1,000 Å, a driving voltage may be increased.

An electron injection layer (EIL) may be formed on the electron transport layer in order to facilitate the injection of electrons from a cathode. An electron injection layer material is not particularly limited.

The electron injection layer material may be selected from known materials such as LiF, NaCl, CsF, $Li_2O$, or BaO. The deposition conditions of the electron injection layer vary according to the type of a used compound, but are generally almost the same as those for the formation of the hole injection layer.

The electron injection layer may be formed to a thickness of about 1 to 100 Å, preferably 5 to 50 Å. If the thickness of the electron injection layer is less than 1 Å, electron injection characteristics may be lowered. On the other hand, if the thickness of the electron injection layer exceeds 10 Å, a driving voltage may be increased.

Finally, a second electrode may be formed on the electron injection layer using vacuum deposition or sputtering. The second electrode may be used as a cathode. A material for forming the second electrode may be metal or alloy with a low work function, an electroconductive compound, or a mixture thereof. For example, the second electrode material may be lithium (Li), magnesium (Mg), aluminum (Al), aluminum-lithium (Al—Li), calcium (Ca), magnesium-indium (Mg—In), magnesium-silver (Mg—Ag), etc. The second electrode may also be a transmissive cathode formed of ITO or IZO to provide a front-emission type device.

Hereinafter, the present invention will be described more specifically with reference to the following working examples. However, the following working examples are only for illustrative purposes and are not intended to limit the scope of the invention.

EXAMPLES
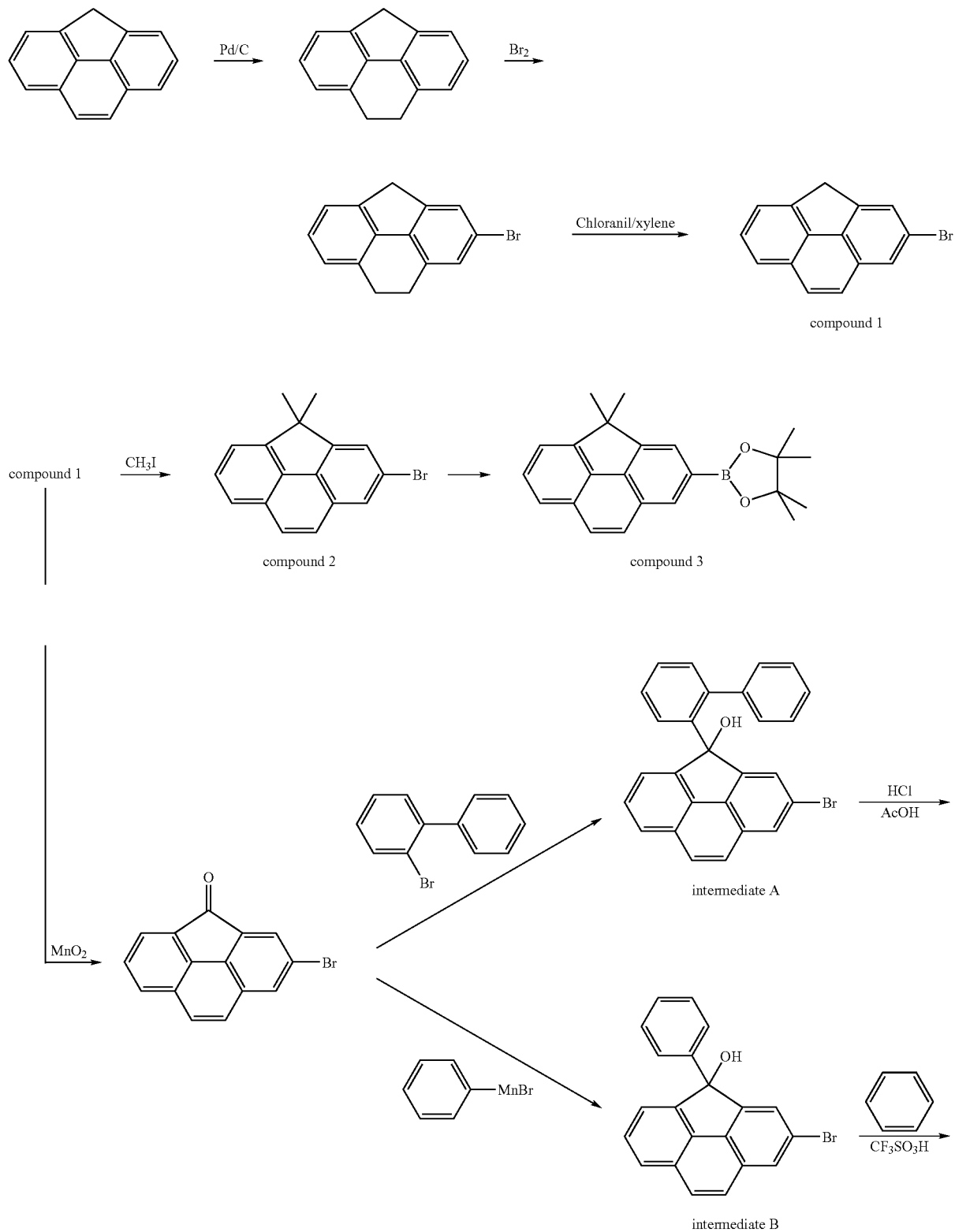

-continued

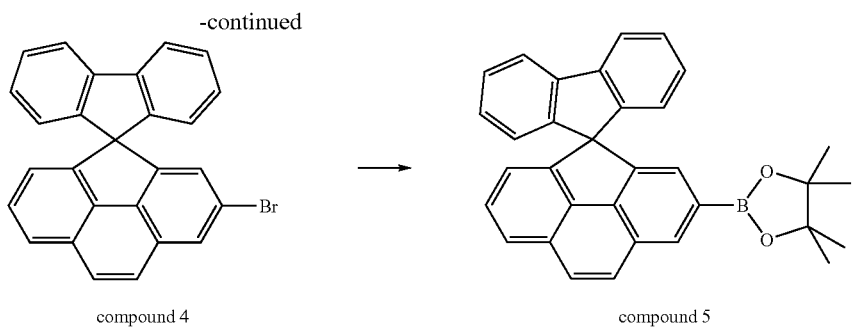

compound 4    compound 5

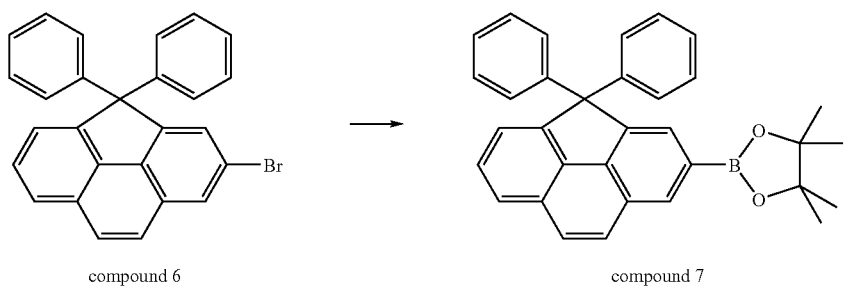

compound 6    compound 7

Synthesis Example 1

1) Synthesis of 8,9-dihydro-4H-cyclopenta[def]phenanthrene 4H-cyclopenta[def]phenanthrene (4.75 g, 25 mmol) was put into a Par reactor, and EtOH (200 ml) was added thereto. 5% Pd/C (3.99 g) was added to the reaction solution, and the resultant solution was incubated under a hydrogen pressure of 40 psi for 24 hours. After the reaction was terminated, the reaction solution was filtered, and the filtrate was concentrated under a reduced pressure to give a white product (4.32 g, 90%).

2) Synthesis of 2-bromo-8,9-dihydro-4H-cyclopenta[def]phenanthrene 8,9-dihydro-4H-cyclopenta[def]phenanthrene (4.42 g, 23 mmol) was put into a 250 ml round bottom flask, and $CCl_4$ (100 ml) was added thereto. The reaction mixture was cooled to 0° C., and $Br_2$ (7.72 g, 48 mmol) was dropwise added thereto. The reaction solution was incubated for four hours and a 10% $NaSO_3$ solution was added thereto. The organic phase was separated, concentrated under a reduced pressure, and recrystallized from n-hexane to obtain 8,9-dihydro-4H-cyclopenta[def]phenanthrene (4.45 g, 55%).

3) Synthesis of Compound 1

2-bromo-8,9-dihydro-4H-cyclopenta[def]phenanthrene (4.45 g, 12.7 mmol) in a 250 ml round bottom flask was dissolved with xylene, and o-chloranil (4.15 g) was added thereto at room temperature. The reaction mixture was heated and refluxed in an oil bath for 72 hours. After the reaction was terminated, the reaction solution was cooled and concentrated under a reduced pressure. The residue was purified by silica gel column chromatography (developing solvent: n-hexane) to give a compound 1 (3.6 g, 81%). $^1$H NMR (300 MHz, $CDCl_3$, δ): 7.98 (2H, s), 7.79 (2H, s), 7.73 (2H, s), 6.94 (dd, 1H), 4.28 (2H, s).

4) Synthesis of Compound 2

2-bromo-4H-cyclopenta[def]phenanthrene (2.6 g, 7.7 mmol), t-BuOH (20.8 g, 61.6 mmol), DMSO (20 ml), and HMPA (20 ml) were put into a 50 ml round bottom flask using a syringe. The reaction mixture was stirred at room temperature for 50 minutes and cooled to 0° C. Then, $CH_3I$ (3.75 ml, 61.6 mmol) was dropwise added to the flask using a syringe at 0° C. and the reaction mixture was stirred at 0° C. for 30 minutes. Then, water (50 ml) and methylene chloride (50 ml) were added to the flask to separate an organic phase. The organic phase was purified by silica gel column chromatography to give a compound 2 (3.6 g, 80%). $^1$H NMR (300 MHz, $CDCl_3$, δ): 7.98 (2H, s), 7.79 (2H, s), 7.73 (2H, s), 6.94 (dd, 1H), 1.93 (m, 6H).

5) Synthesis of Compound 3

3.6 g (1 eq, 12.12 mmol) of the compound 2 was dissolved in 100 ml of THF in a 250 ml round bottom flask under an argon atmosphere, and 5.5 ml (1.2 eq, 14.54 mmol) of n-BuLi (2.5M in hexane) was added thereto at −78° C. The reaction mixture was stirred at −78° C. for one hour, 3.3 ml (1.3 eq, 15.75 mmol) of 2-isopropoxy-4,4,5,5-tetramethyl-1,3,2-dioxaborolane was added thereto, and the reaction mixture was stirred at room temperature for two hours. Then, water (50 ml) was added so that the reaction was terminated, and the resultant solution was extracted with brine and methylene chloride. The extracted organic phase was dried over anhydrous magnesium sulfate and filtrated to remove a solvent. The residue was dissolved in a trace amount of toluene and purified on a silica gel column to remove impurities. Finally, 2.5 g (60%) of a white solid was obtained using a developing solvent with higher polarity.

Synthesis Example 2

1) Synthesis of 2-bromo-cyclopenta[def]phenanthren-4-one

Benzene (200 ml) was put into a 250 ml round bottom flask, and the compound 1 (3.6 g, 10.4 mmol) was added thereto. $MnO_2$ (150 g) was added to the reaction mixture, and the resultant mixture was heated and refluxed in an oil bath for 18 hours. After the reaction was terminated, the reaction solution was filtered to remove $MnO_2$, and sufficiently washed with $CHCl_3$, THF, and MeOH in sequence. The filtrate was concentrated under a reduced pressure and the residue was recrystallized from acetone to give the titled compound (1.45 g, 39%).

2) Synthesis of Intermediate A 2-bromo biphenyl (0.68 g, 2.95 mmol) was dissolved in anhydrous THF (10 ml), and the resultant solution was cooled to −78° C. Then, t-BuLi (3.5 ml) was gradually dropwise added thereto, and the reaction mixture was stirred for one hour. Then, a solution of 2-bromo-cyclopenta[def]phenanthren-4-one (1 g, 2.95 mmol) in anhydrous THF (5 ml) was dropwise added to the reaction solution for 30 minutes. After the reaction was terminated, the resultant solution was concentrated under a reduced pressure and extracted with ethyl acetate and brine to separate an organic phase. The organic phase was concentrated, and the residue was purified on a silica gel column to give an intermediate A (3.6 g).

3) Synthesis of Compound 4

The intermediate A was dissolved in acetic acid (30 ml), and the resultant solution was cooled to 0° C. Then, concentrated hydrochloric acid (1 ml) was dropwise added thereto, and the reaction mixture was incubated for two hours. After the reaction was terminated, the reaction solution was filtered, and the filtered product was washed with acetic acid and methanol to give 2 g (80%) of a white solid. $^1H$ NMR (300 MHz, $CDCl_3$, δ): 7.22-7.26 (m, 8H), 7.70 (s, 2H), 7.80 (s, 3H), 8.00 (s, 2H).

4) Synthesis of Compound 5

A compound 5 was synthesized in the same manner as in synthesis of the compound 3 of Synthesis Example 1 except that the compound 4 was used instead of the compound 2.

Synthesis Example 3

1) Synthesis of Intermediate B 1.0 g (2.76 mmol) of 2-bromo-cyclopenta[def]phenanthren-4-one) was dissolved in dry ether (30 ml) and THF (10 ml), and phenylmagnesium bromide (3.0M in ether) was gradually added thereto under a nitrogen gas atmosphere. The reaction mixture was refluxed for three hours, and water was added thereto so that the reaction was terminated. The resultant solution was adjusted to pH of 3-4 with a 1N-HCl solution and extracted with ethylacetate. The organic phase was dried over anhydrous sodium sulfate, filtered, and concentrated under a reduced pressure. The resultant solid was purified by silica gel column chromatography to give 0.79 g (65%) of an intermediate B as a solid phase.

2) Synthesis of Compound 6

0.79 g (1.79 mmol) of the intermediate B was dissolved in dry benzene (20 ml) and 0.48 ml (5.38 mmol, 3 eq.) of trifluoromethane sulfonic acid was dropwise added thereto. The reaction mixture was incubated at 80° C. for two hours. The resultant solution was diluted with water and extracted with ethyl acetate. The organic phase was dried over anhydrous sodium sulfate, filtered, and concentrated under a reduced pressure. The resultant solid was purified by silica gel column chromatography and recrystallized from a EtOAc-Hex mixed solvent to give 0.65 g (63%) of a compound 6 as a solid phase. $^1H$ NMR (300 MHz, $CDCl_3$, δ): 7.22-7.26 (m, 10H), 7.70 (s, 2H), 7.80 (s, 3H), 8.00 (s, 2H)

3) Synthesis of Compound 7

A compound 7 was synthesized in the same manner as in synthesis of compound 3 of Synthesis Example 1 except that the compound 6 was used instead of the compound 2.

Synthesis of Emitting Materials

1) Synthesis of Material 1 (Formula 18)

1.0 g (1 eq, 2.9 mmol) of the compound 3, 1.37 g (1 eq, 2.9 mmol) of 2-bromo-7-phenyl-9,9'-diphenylfluorene, 0.26 g (0.1 eq, 0.29 mmol) of tetrakis(triphenylphosphine)palladium(0), 1 ml (1 eq, 2.9 mmol) of 2M $K_2CO_3$, and 0.68 g (1 eq, 2.9 mmol) of tetrabutylammoniumbromide were put into a 100 ml round bottom flask under an argon gas atmosphere, and THF (50 ml) and toluene (20 ml) were added thereto. The reaction mixture was refluxed at 100° C. for 16 hours. When the reaction solution turned dark brown, water was added, and the resultant solution was extracted with ethylacetate. The extracted organic phase was dried over anhydrous magnesium sulfate and filtered to remove a solvent. The residue was dissolved in a trace amount of toluene and purified on a silica gel column. The resultant solid was recrystallized from toluene and methanol to give 1.15 g (65%) of a material 1 represented by Formula 18. $^1H$ NMR (300 MHz, $CDCl_3$, δ): 8.11 (s, 2H), 7.98 (s, 3H), 7.81 (s, 2H), 7.75-7.10 (m, 23H), 1.93 (m, 6H).

2) Synthesis of Material 2 (Formula 29)

A material 2 represented by Formula 29 was synthesized in the same manner as in the synthesis of the material 1 except that the compound 5 was used instead of the compound 3, and 6,12-dibromo-chrysene was used instead of 2-bromo-7-phenyl-9,9'-diphenylfluorene. $^1H$ NMR (300 MHz, $CDCl_3$, δ): 8.61-7.45 (m, 40H).

3) Synthesis of Material 3 (Formula 30)

A material 3 represented by Formula 30 was synthesized in the same manner as in the synthesis of the material 1 except the compound 7 was used instead of the compound 3, and {4-[2-(4-bromo-phenyl)-vinyl]-phenyl}-dinaphthalen-2-yl-amine was used instead of 2-bromo-7-phenyl-9,9'-diphenylfluorene. $^1H$ NMR (300 MHz, $CDCl_3$, δ): 8.23-7.12 (m, 39H), 6.95 (s, 2H)

As shown above, in the embodiments of the present invention, a low molecular weight compound obtained by reacting a cyclopentaphenanthrene compound wherein the 2- or 6-position is functionalized with halogen, borate, aldehyde, hydroxyl, or the like, with another compound, is used as an organoelectroluminescent material. Various substituents can be incorporated into the 4-position of the cyclopentaphenanthrene of the low molecular weight compound, thereby enabling more stable film formation and improving solubility in a solvent.

Example 1

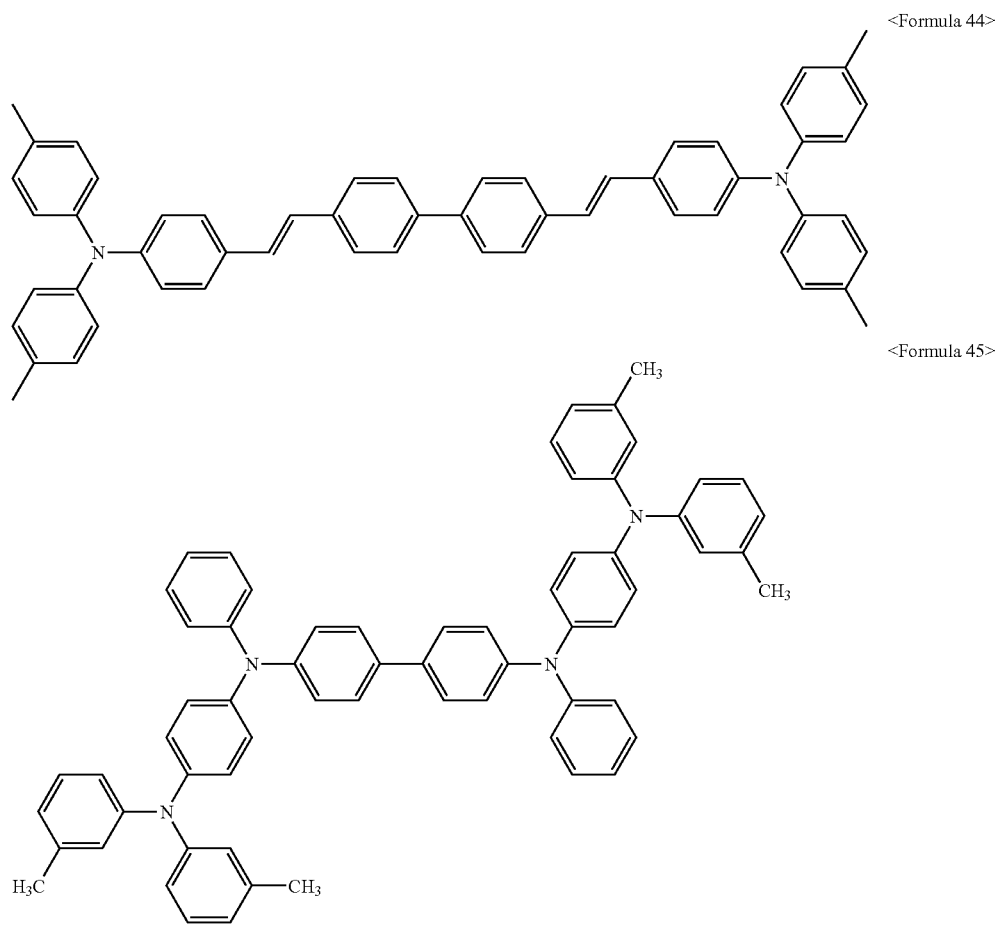

Organoelectroluminescent devices having the following structure were manufactured using the material 1 as a host of an emitting layer and a compound of Formula 44 above as a dopant of the emitting layer: ITO/Formula 45 (200 Å)/α-NPD (300 Å)/material 1: Formula 44 (300 Å)/Alq3 (40 Å)/LiF (10 Å)/Al (2000 Å).

A 15 Ω/cm² (1,000 Å) ITO glass substrate was cut into pieces of 50 mm×50 mm×0.7 mm in size, followed by ultrasonic cleaning in acetone, isopropyl alcohol, and pure water (15 minutes for each) and then UV/ozone cleaning (30 minutes) to form anodes. The compound of Formula 45 for hole injection layers and α-NPD for hole transport layers were sequentially vacuum-deposited on the anodes, and a mixture of the material 1 and the compound of Formula 44 (weight ratio=100:10) was then vacuum-deposited to form emitting layers. Then, an Alq3 compound was vacuum-deposited to a thickness of 40 Å on the emitting layers to form electron transport layers. LiF (10 Å, electron injection layers) and Al (2000 Å, cathodes) were sequentially vacuum-deposited on the electron transport layers to thereby complete organoelectroluminescent devices as illustrated in FIG. 1A. The organoelectroluminescent devices exhibited blue emission of 10,000 cd/m² at a voltage of 7.3 V and efficiency of 5.6 cd/A.

Example 2

Organoelectroluminescent devices having the following structure were manufactured in the same manner as in Example 1 except that the material 2 was used as a host of an emitting layer: ITO/Formula 45 (200 Å)/α-NPD (300 Å)/material 2 Formula 44 (300 Å)/Alq3 (40 Å)/LiF (10 Å)/Al (2000 Å). The organoelectroluminescent devices exhibited blue emission of 9,200 cd/m² at a voltage of 7.0 V and efficiency of 4.4 cd/A.

Example 3

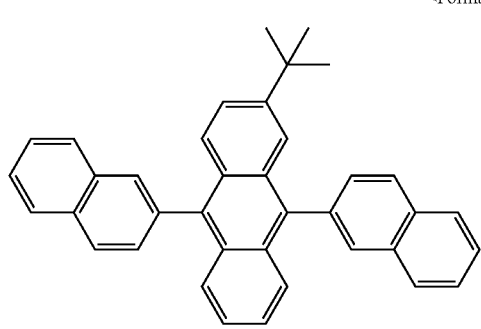

<Formula 46>

Organoelectroluminescent devices having the following structure were manufactured in the same manner as in Example 1 except that a compound of Formula 46 was used instead of the material 1 as a host of an emitting layer, and the material 3 was used instead of the compound of Formula 44 as a dopant of the emitting layer: ITO/Formula 45 (200 Å)/α-NPD (300 Å)/Formula 46: material 3 (300 Å)/Alq3 (40 Å)/LiF (10 Å)/Al (2000 Å). The organoelectroluminescent devices exhibited blue emission of 14,000 cd/m² at a voltage of 6.5 V and efficiency of 7.8 cd/A.

The above Examples show that materials according to the embodiments of the present invention have good EL characteristics as phosphorescent and fluorescent materials.

A compound of Formula 1 according an embodiment of to the present invention is adapted for both dry and wet processes, and has good emission characteristics and thermal stability. Therefore, the use of the compound of the present invention enables to produce an organoelectroluminescent device having a low driving voltage and good color purity.

Other embodiments of the invention, including modifications and adaptions of the disclosed embodiments, will be apparent to those skilled in the art from consideration of the specification and practice of the invention disclosed herein. The foregoing descriptions of implementations of the invention have been presented for purposes of illustration and description. The descriptions are not exhaustive and do not limit the invention to the precise form disclosed. Modifications and variations are possible in light of the above teachings or may be acquired from practicing the invention.

What is claimed is:

1. A cyclopentaphenanthrene compound represented by Formula 1:

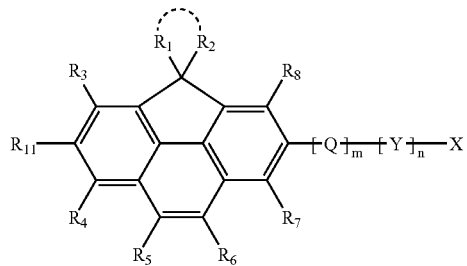

(1)

wherein each Q is independently one of groups represented in Formulas 2A to 2R:

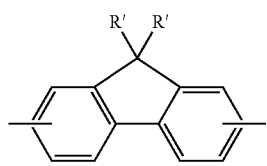

2A

-continued

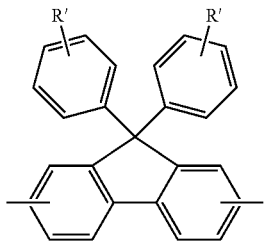

2B

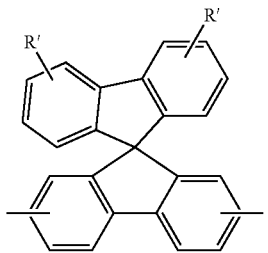

2C

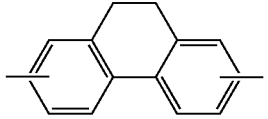

2D

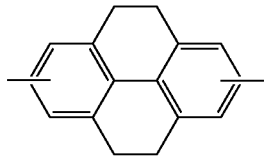

2E

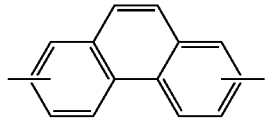

2F

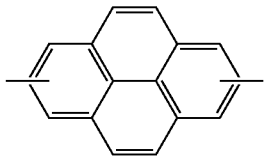

2G

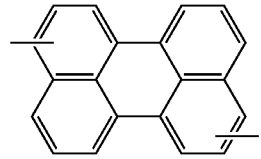

2H

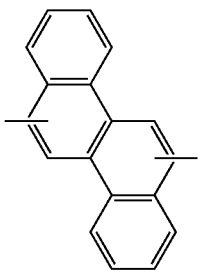

2I

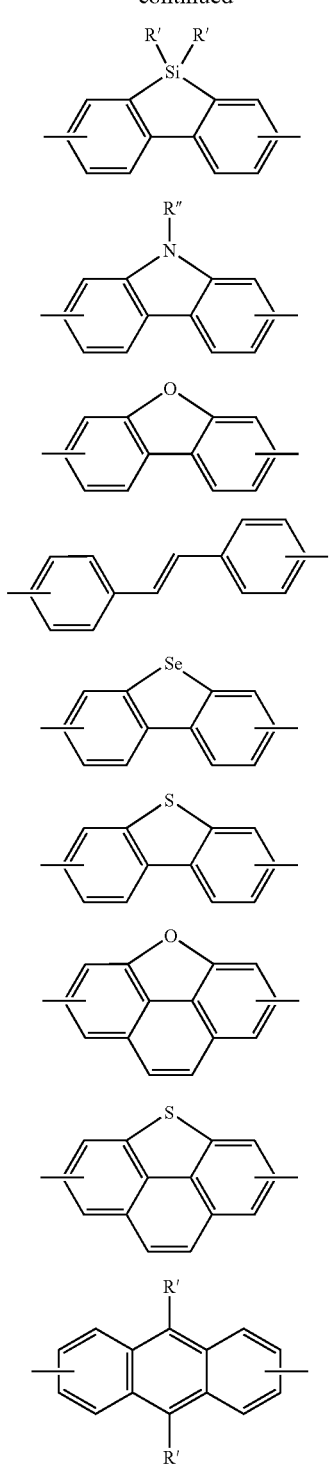

wherein R' and R" are hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group, with the proviso that, when X is H, m is 1, n is 0, and Q is Formula 2A, R' and R" are —Si($Z_3$)($Z_4$)($Z_5$) where $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

X is hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

m is an integer of 1 to 3, and when m is 2 or 3, Qs may be the same or different;

n is an integer of 0 to 3, and when n is 2 or 3, Ys may be the same or different from each other;

$R_1$ and $R_2$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, a substituted or unsubstituted C2-C30 heteroaromatic ring;

$R_3$ through $R_8$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and $R_{11}$ is hydrogen, halogen, a cyano group, a hydroxyl group, or a substituted or unsubstituted C1-C20 alkyl group.

2. The cyclopentaphenanthrene compound of claim 1, wherein the

in Formula 1 is represented by one of Formulae 3 through 6:

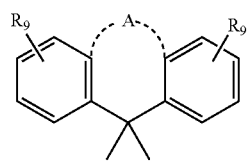
(3)

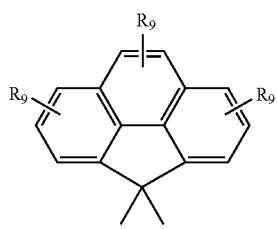
(4)

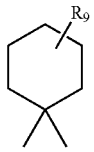
(5)

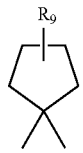
(6)

wherein each $R_9$ is independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and A is a single bond, —O—, —S—, —Se—, or —(CH$_2$)$_p$— where p is an integer of 1 to 5.

3. The cyclopentaphenanthrene compound of claim 1, which is a compound selected from the group consisting of compounds represented by Formulae 7 through 9:

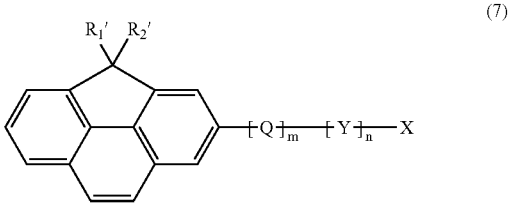
(7)

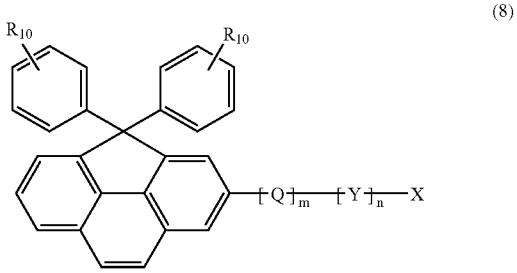
(8)

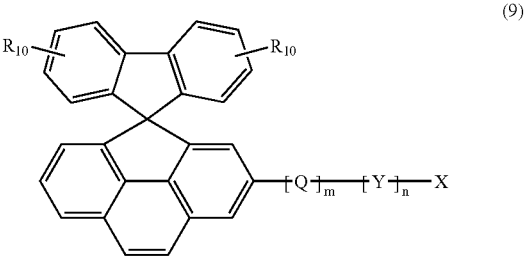
(9)

wherein, each Q is independently one of groups represented in Formulas 2A to 2R:

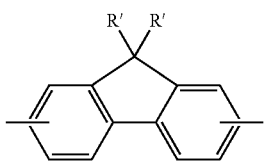
2A

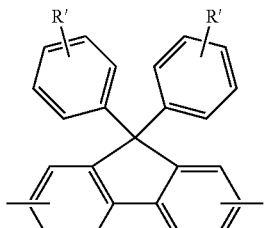
2B

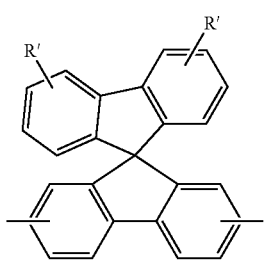
2C

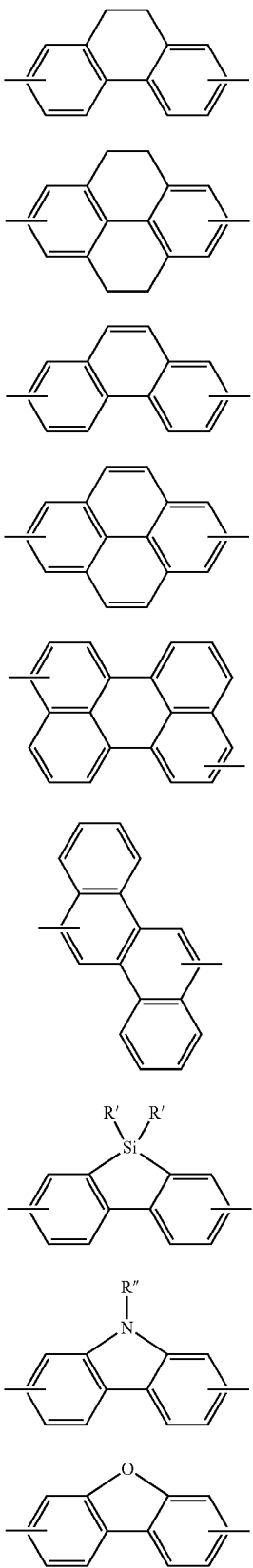

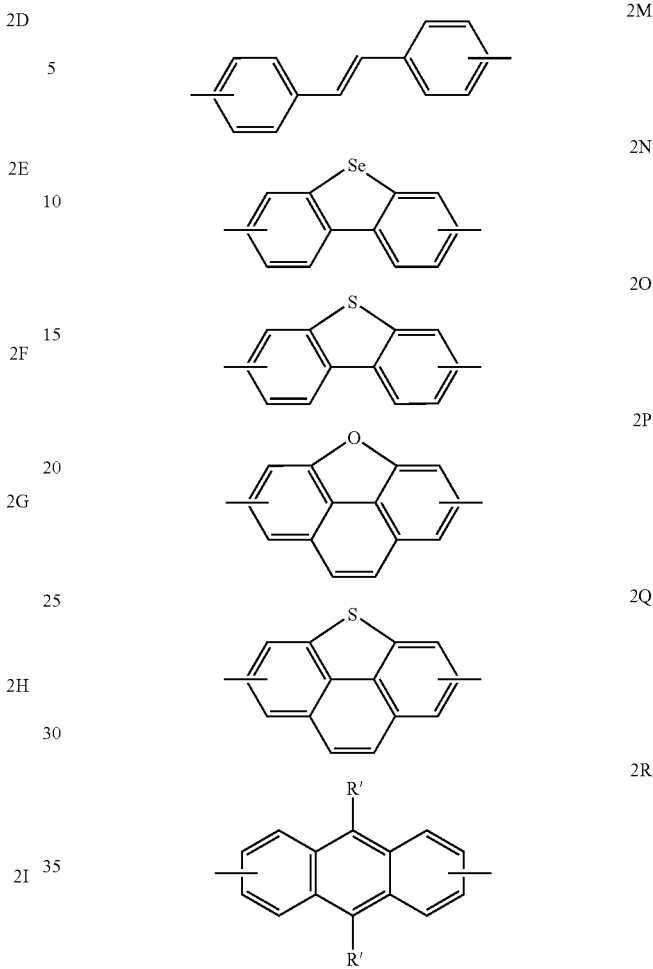

wherein R' and R" are hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group, with the proviso that, when X is H, m is 1, n is 0, and Q is Formula 2A, R' and R" are —Si($Z_1$)($Z_4$)($Z_5$) where $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

X is hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

m is an integer of 1 to 3, and when m is 2 or 3, Qs may be the same or different from each other;

n is an integer of 0 to 3, and when n is 2 or 3, Ys may be the same or different from each other;

each $R_{10}$ is independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and $R_1'$ and $R_2'$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group.

4. The cyclopentaphenanthrene compound of claim 3, wherein in Formulae 7 through 9, —[Y]$_n$—X is selected from the group consisting of groups represented in Formulae 10-1 to 10-116:

<Formula 10>

10-1
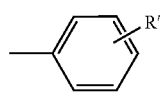

10-2
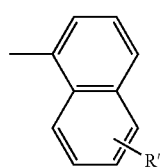

-continued 10-3
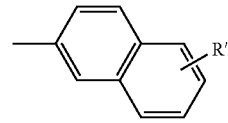

10-4
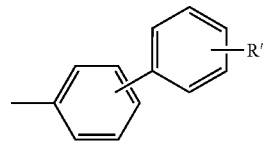

10-5
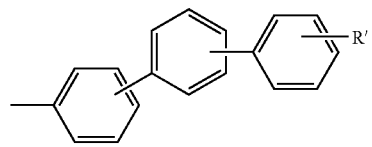

10-6
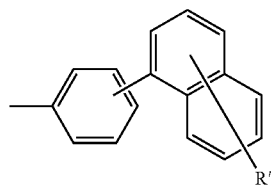

10-7
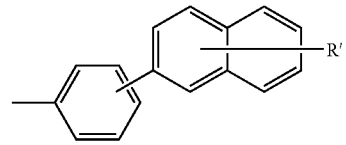

10-8
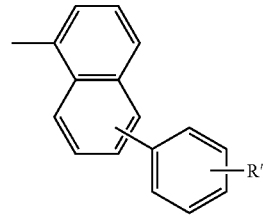

10-9
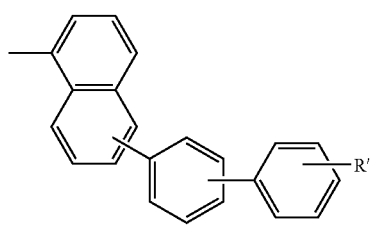

10-10
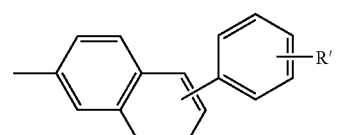

10-11
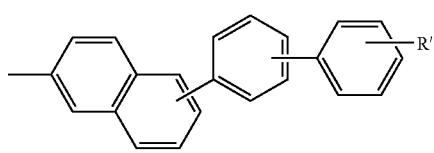

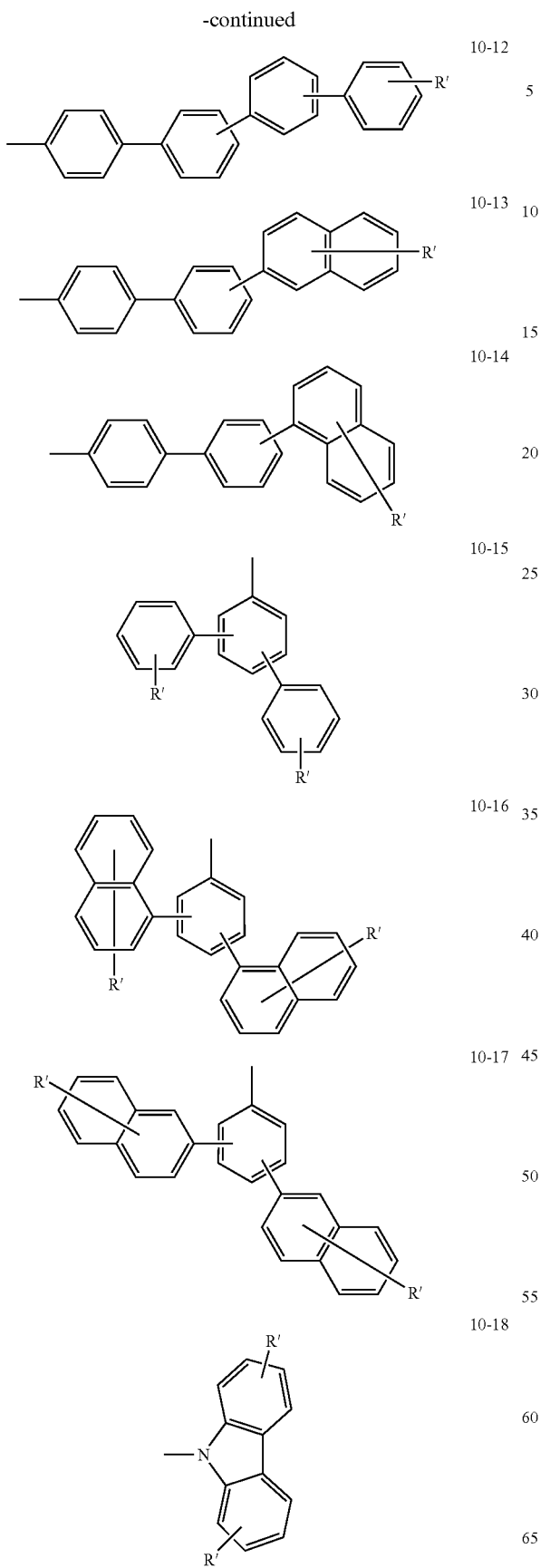
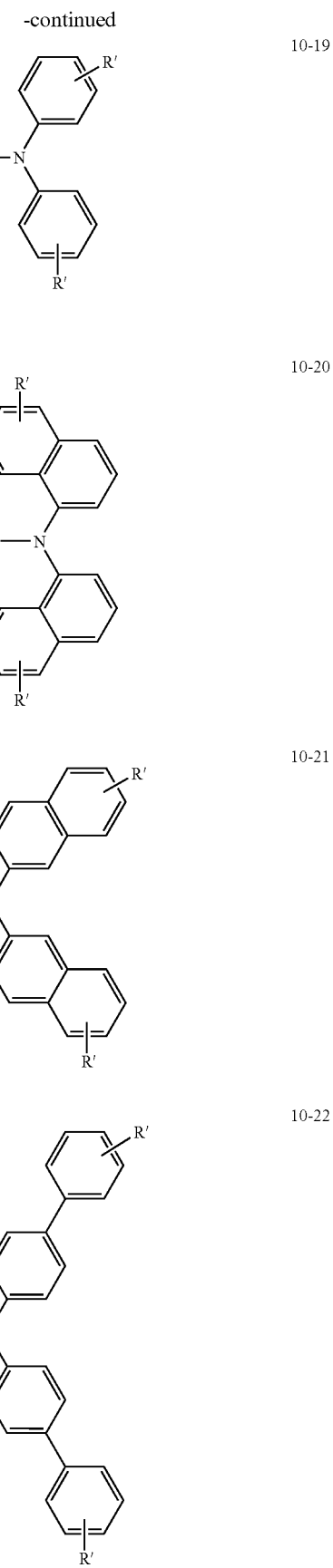

-continued
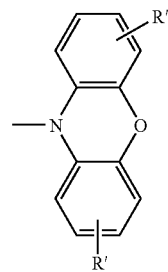 10-23
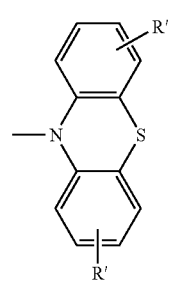 10-24
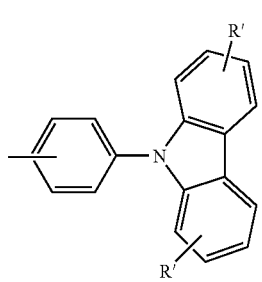 10-25
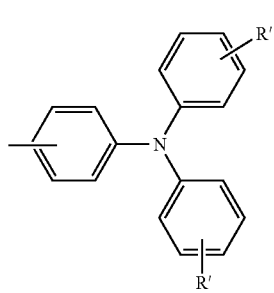 10-26
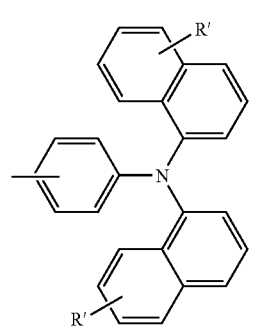 10-27
-continued
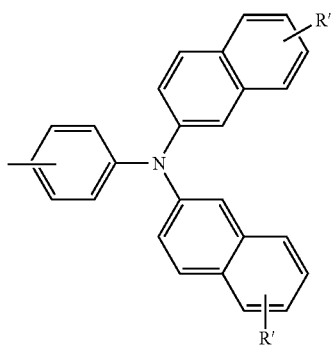 10-28
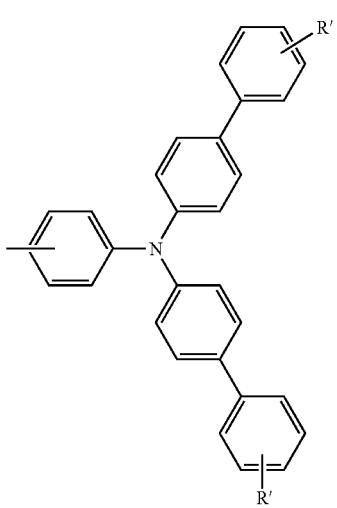 10-29
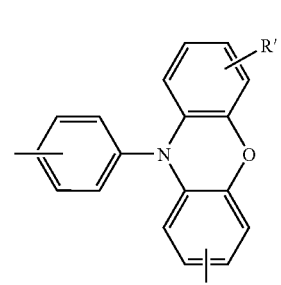 10-30
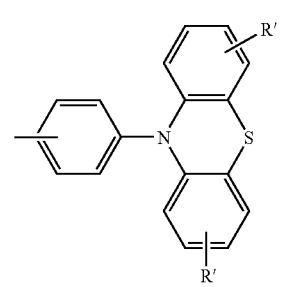 10-31

-continued
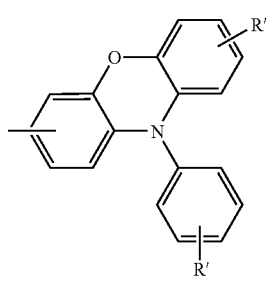
10-32
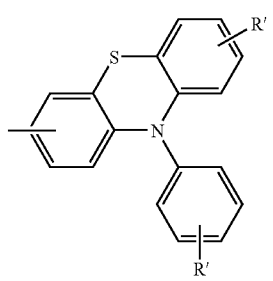
10-33
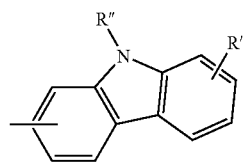
10-34
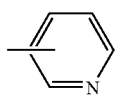
10-35
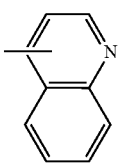
10-36
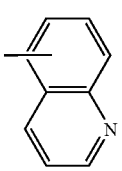
10-37
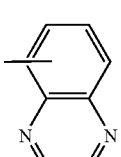
10-38
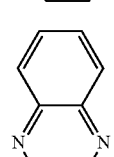
10-39
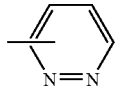
10-40
-continued
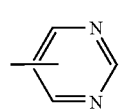
10-41
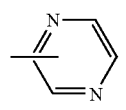
10-42
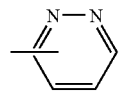
10-43
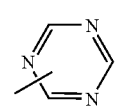
10-44
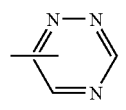
10-45
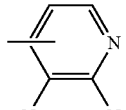
10-46
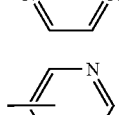
10-47
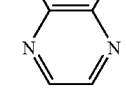
10-48
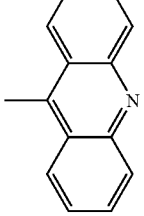
10-49
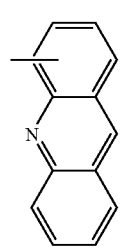
10-50
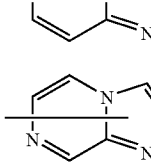
10-51

-continued
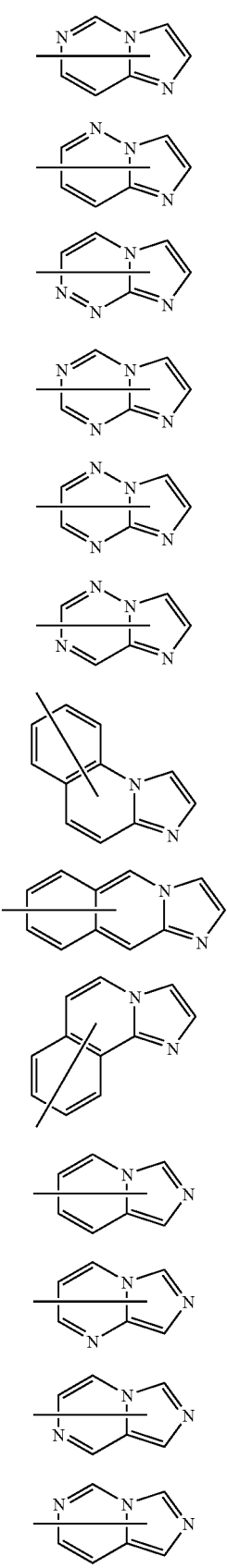
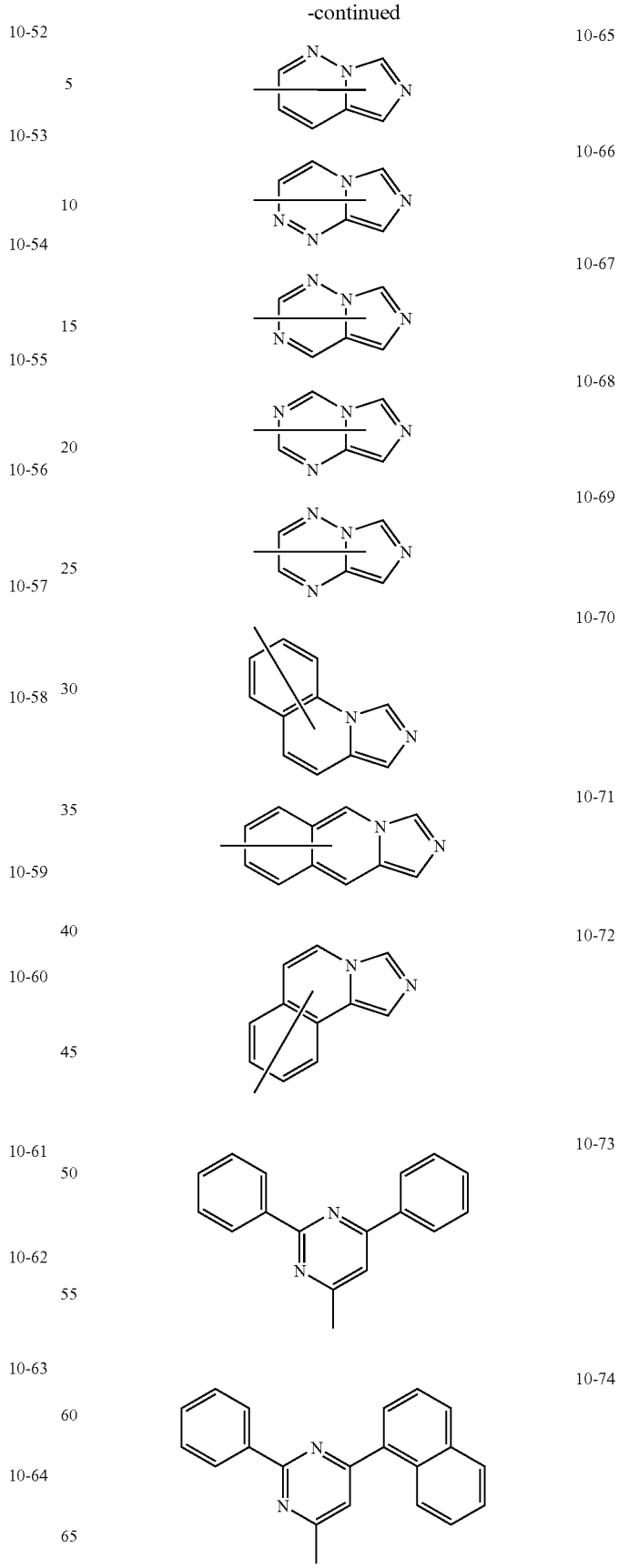

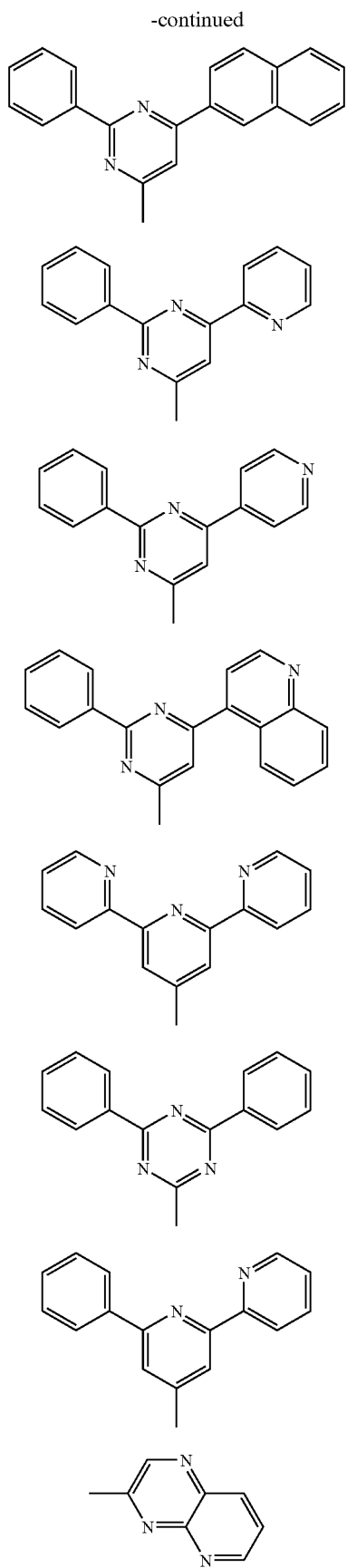
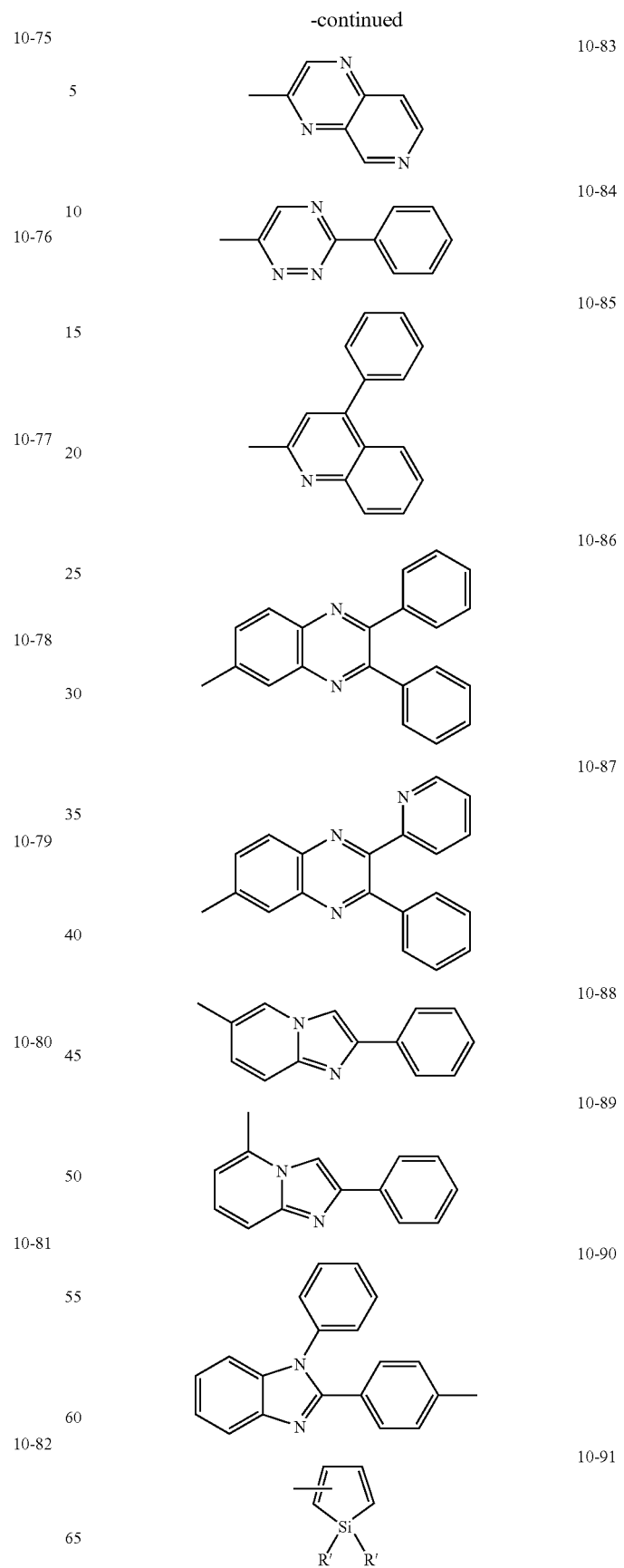

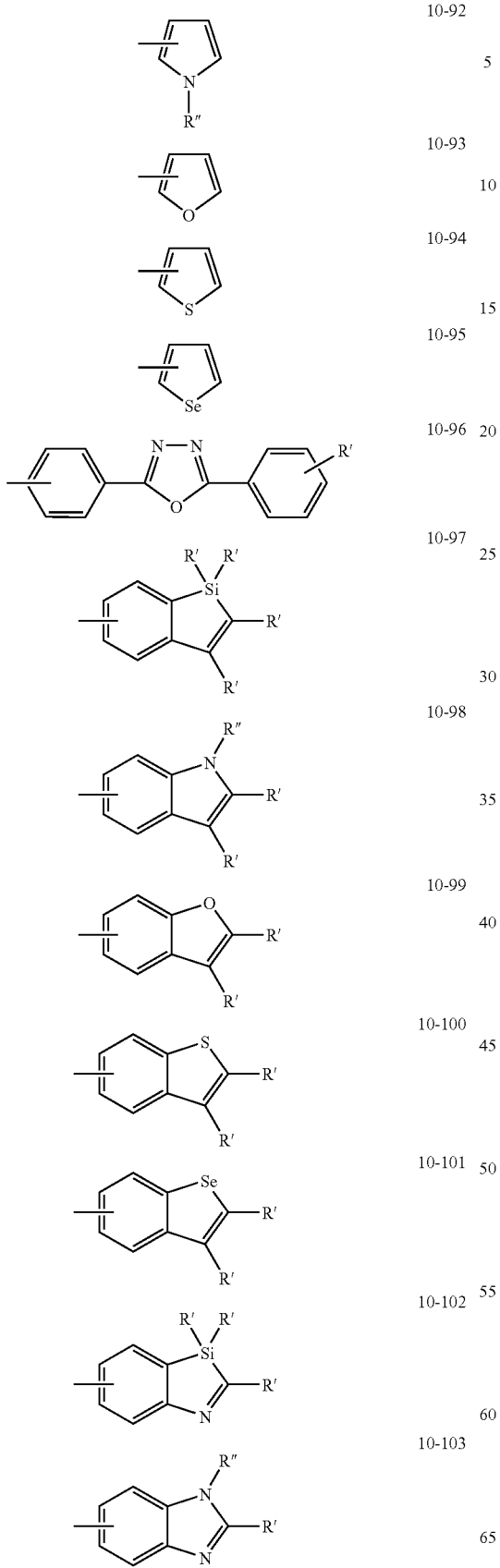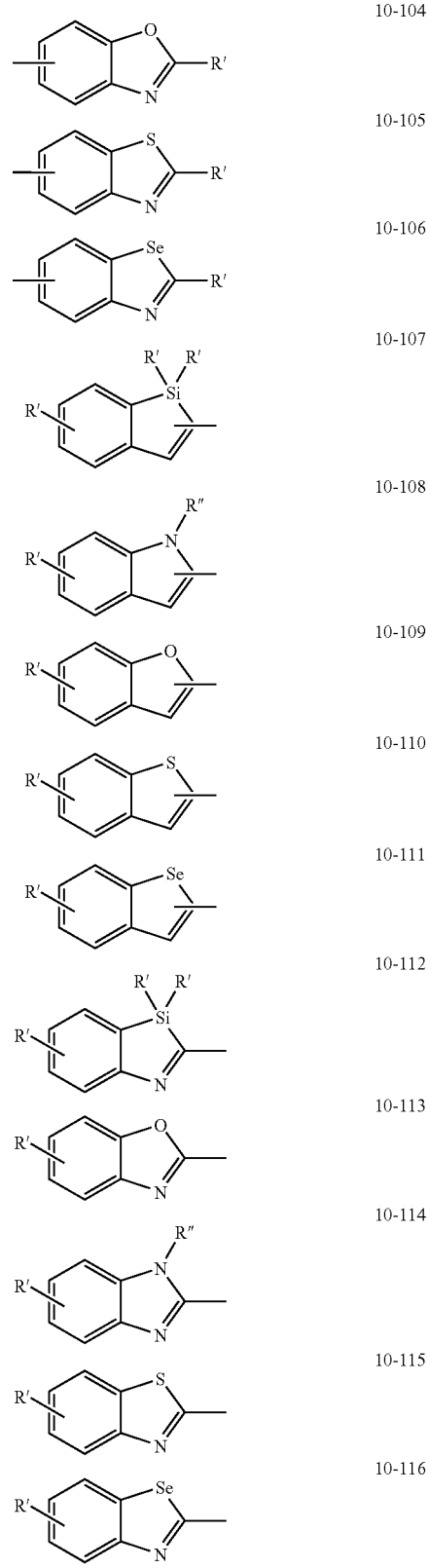
wherein R' and R" are hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group.

5. A cyclopentaphenanthrene compound selected from the group consisting of compounds represented by Formulae 15 through 43:

(15)
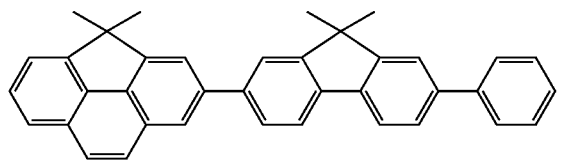

(16)
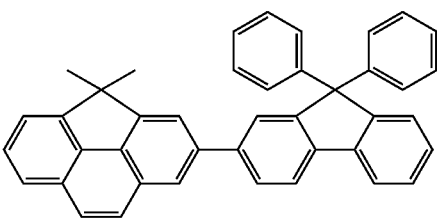

(17)
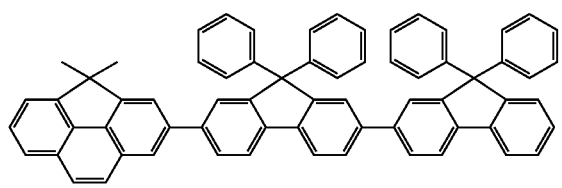

(18)
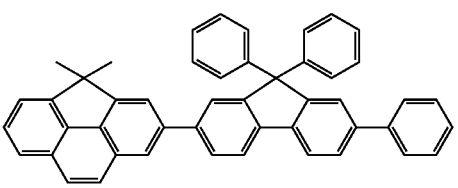

(19)
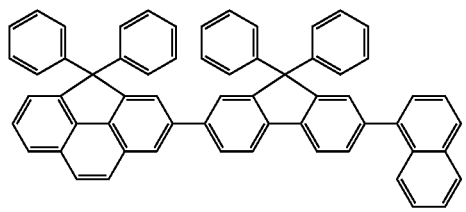

(20)
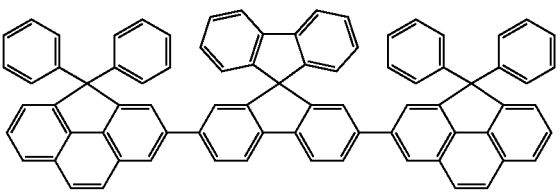

(21)
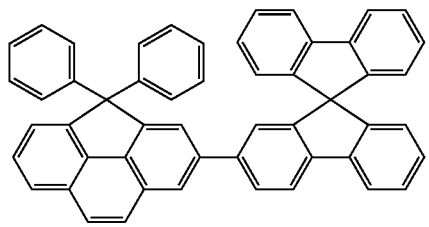

(22)
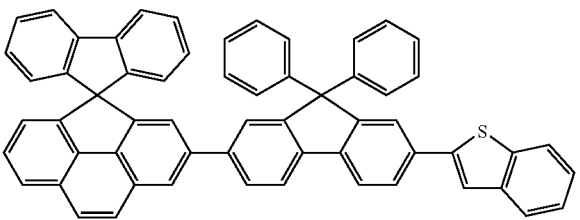

(23)
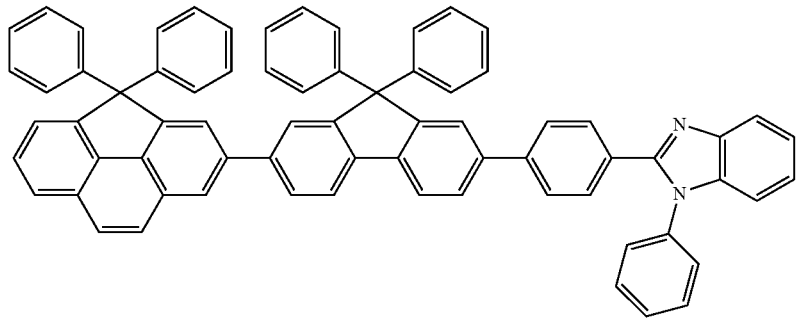

-continued
(24)
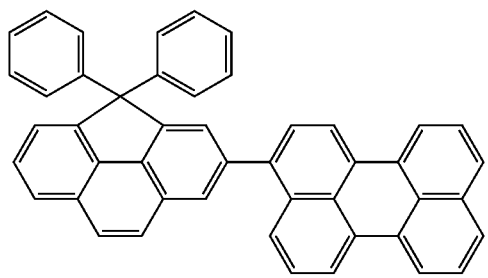
(25)
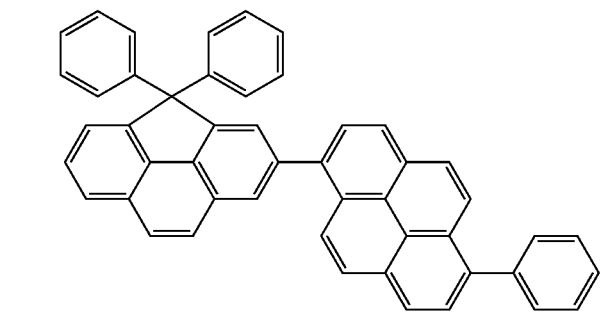
(26)
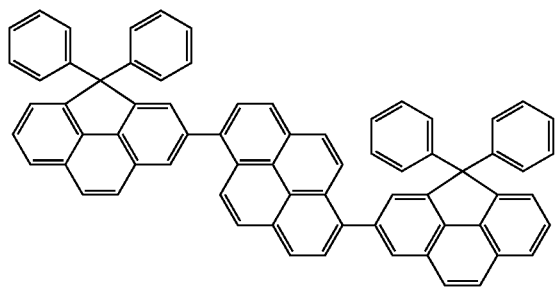
(27)
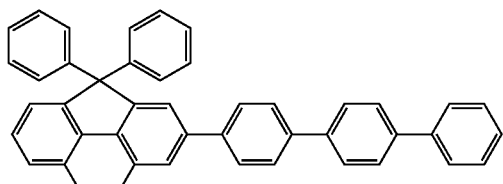
(28)
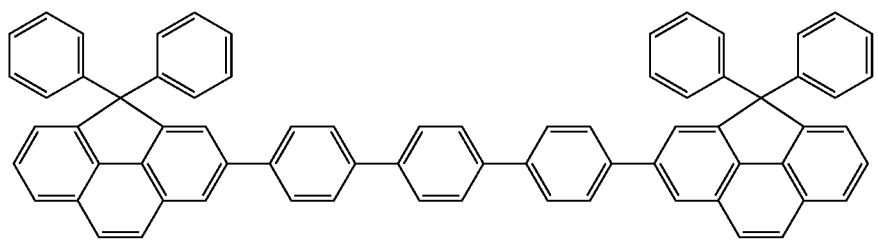
(29)
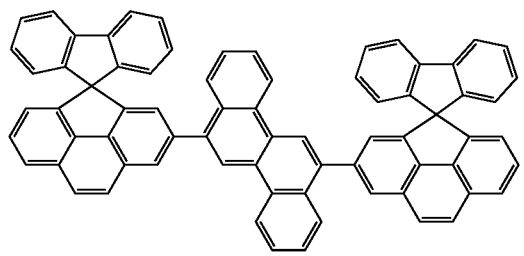
(30)
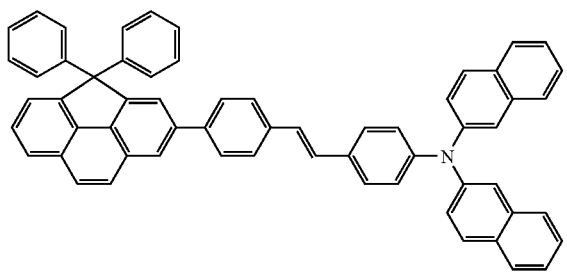
(31)
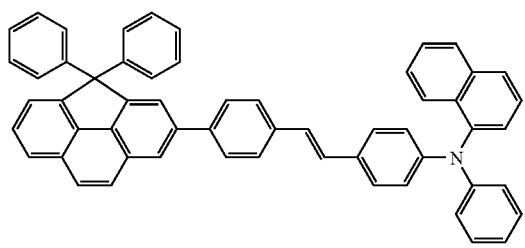
(32)
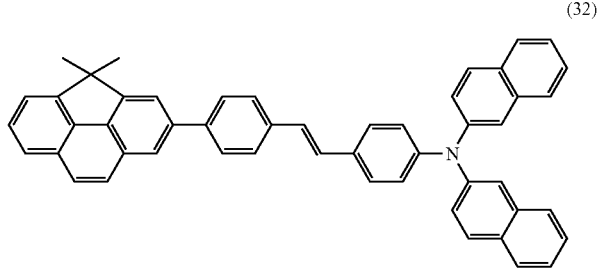

-continued
(33)
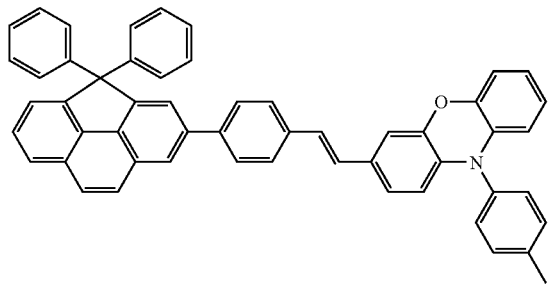
(34)
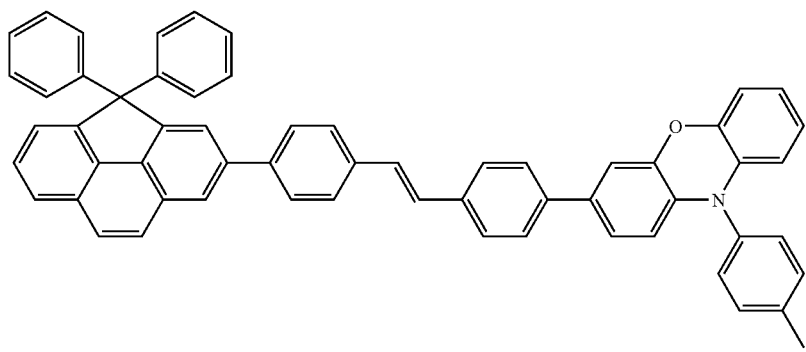
(35)
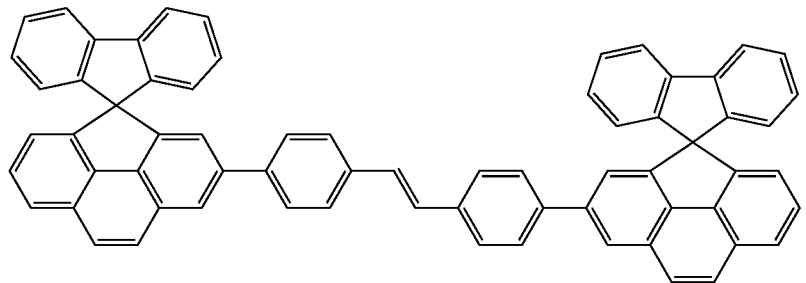
(36)
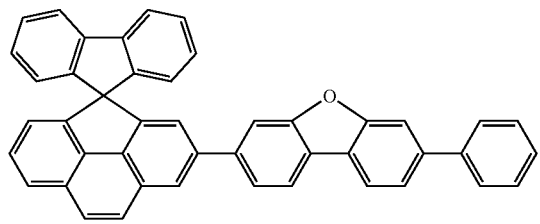
(37)
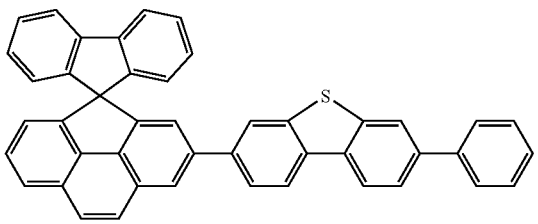
(38)
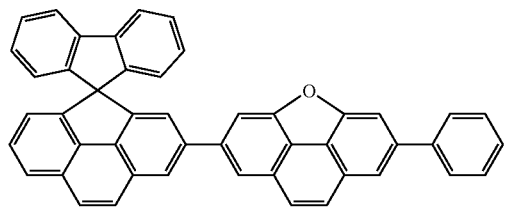
(39)
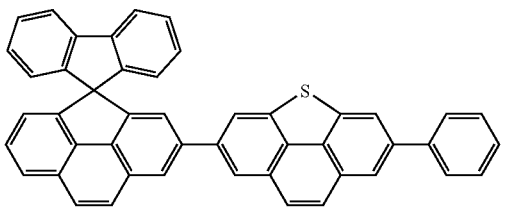

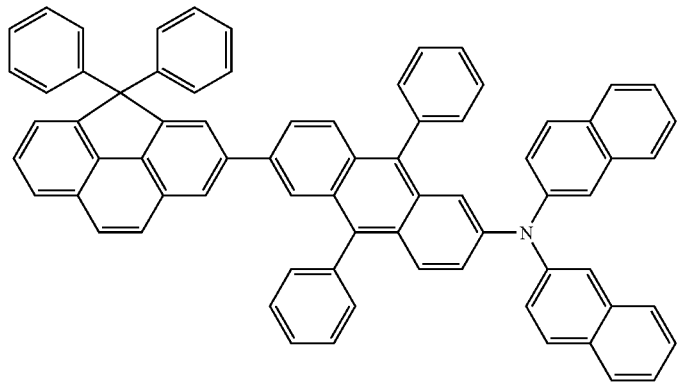
(40)
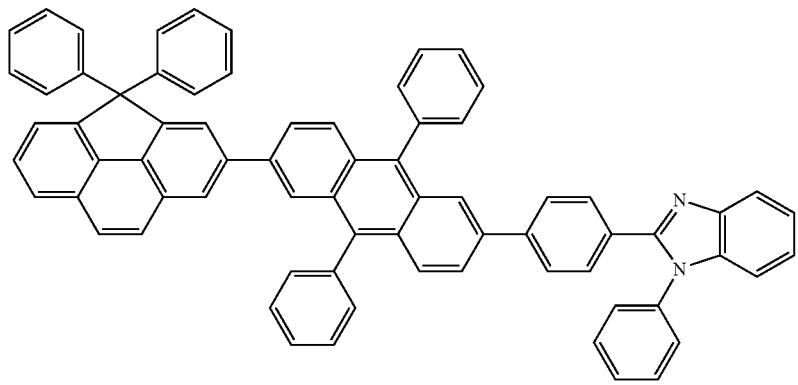
(41)
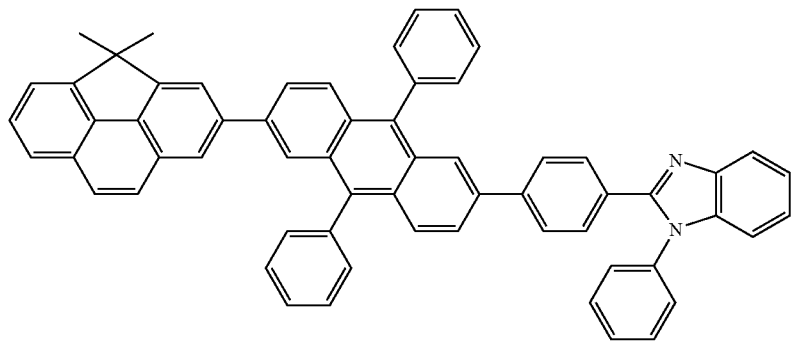
(42)
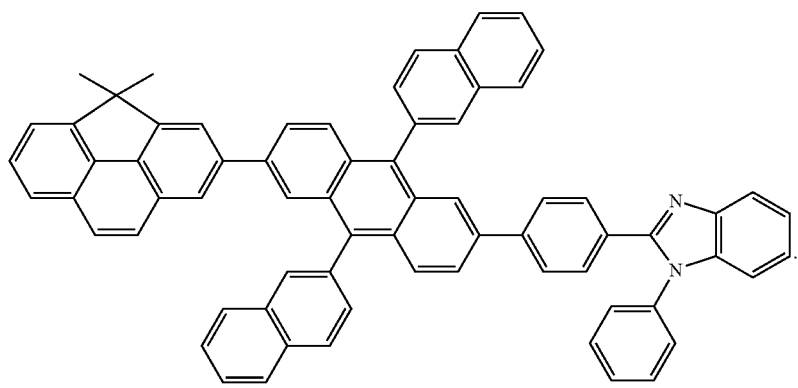
(43)

6. An organoelectroluminescent device comprising a pair of electrodes and at least one organic layer interposed between the pair of electrodes, said at least one organic layer comprising an organic layer formed of the compound of claim 1, said organic layer formed of the compound of claim 1 comprising at least one of an emitting layer, a hole injection layer, and a hole transport layer.

7. An organoelectroluminescent device comprising:

a first electrode;

a second electrode; and at least one organic layer interposed between the first electrode and the second electrode, the organic layer comprising a compound represented by Formula 1:

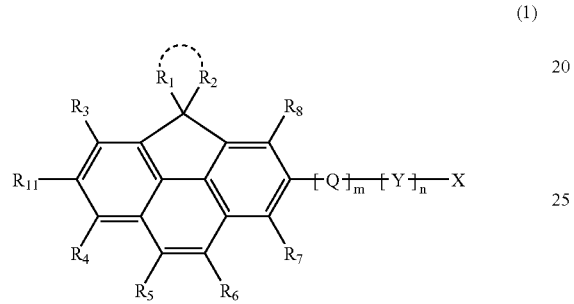

(1)

wherein each Q is independently one of groups represented in Formulas 2A to 2R:

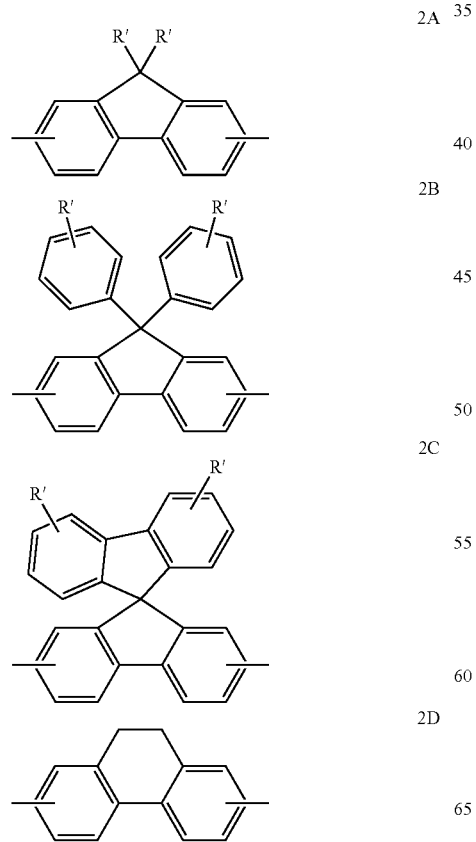

2A

2B

2C

2D

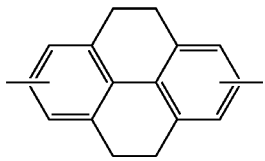

2E

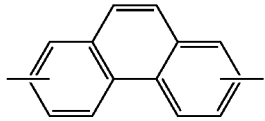

2F

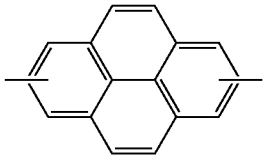

2G

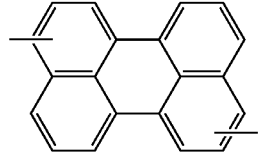

2H

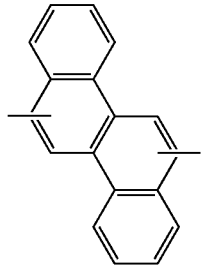

2I

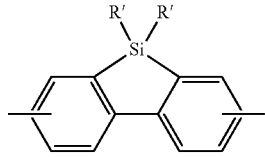

2J

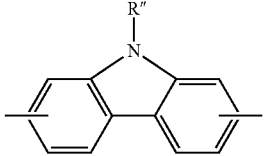

2K

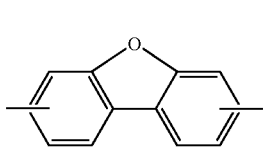

2L

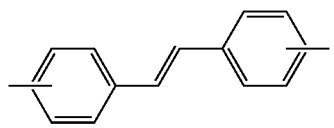

2M

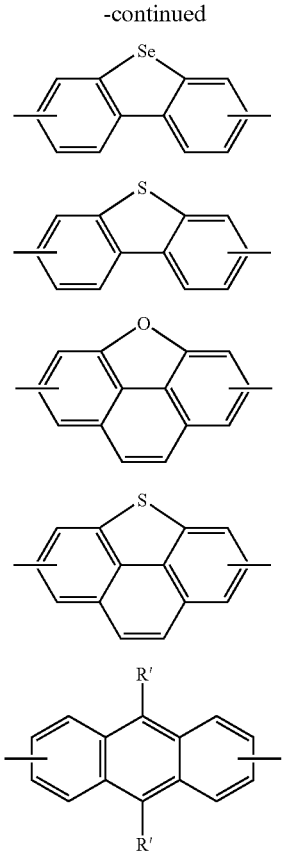

wherein R' and R" are hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_s$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group, with the proviso that, when X is H, m is 1, n is 0, and Q is Formula 2A, R' and R" are —Si($Z_3$)($Z_4$)($Z_5$) where $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

X is hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

m is an integer of 1 to 3, and when m is 2 or 3, Qs may be the same or different;

n is an integer of 0 to 3, and when n is 2 or 3, Ys may be the same or different from each other;

$R_1$ and $R_2$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group, and $R_1$ and $R_2$ can be optionally linked together to form a substituted or unsubstituted C3-C20 aliphatic ring, a substituted or unsubstituted C5-C30 heteroaliphatic ring, a substituted or unsubstituted C6-C30 aromatic ring, a substituted or unsubstituted C2-C30 heteroaromatic ring;

$R_3$ through $R_8$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and $R_{11}$ is hydrogen, halogen, a cyano group, a hydroxyl group, or a substituted or unsubstituted C1-C20 alkyl group.

8. The organoelectroluminescent device of claim 7, wherein the

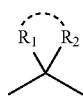

in Formula 1 is represented by one of Formulae 3 through 6:

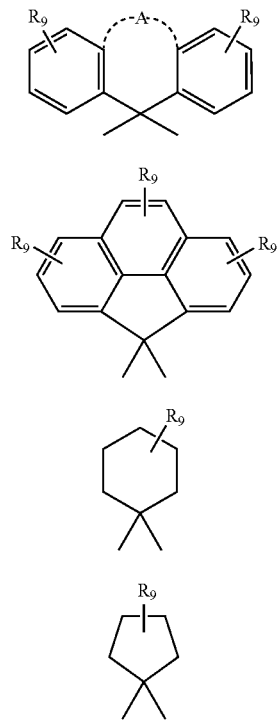

(3)

(4)

(5)

(6)

wherein each $R_9$ is each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and A is a single bond, —O—, —S—, —Se—, or —(CH$_2$)$_p$— where p is an integer of 1 to 5.

9. The organoelectroluminescent device of claim 7, which is a compound selected from the group consisting of compounds represented by Formulae 7 through 9

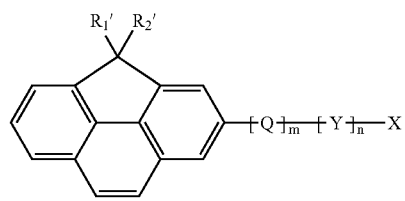

(7)

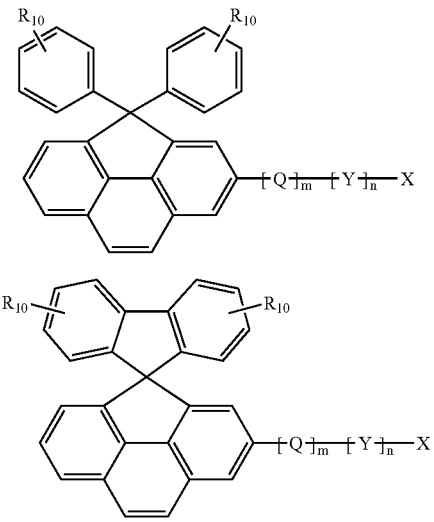

(8)

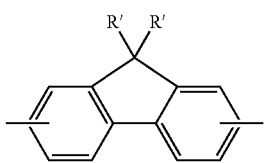

(9)

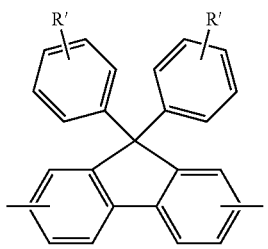

wherein, each Q is independently one of groups represented in Formulas 2A to 2R:

2A

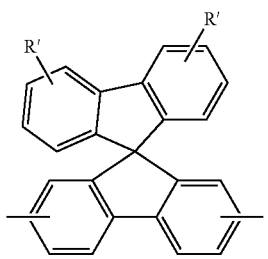

2B

2C

2D

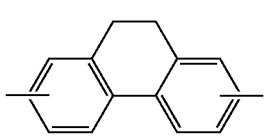

2E

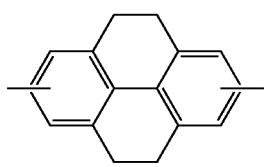

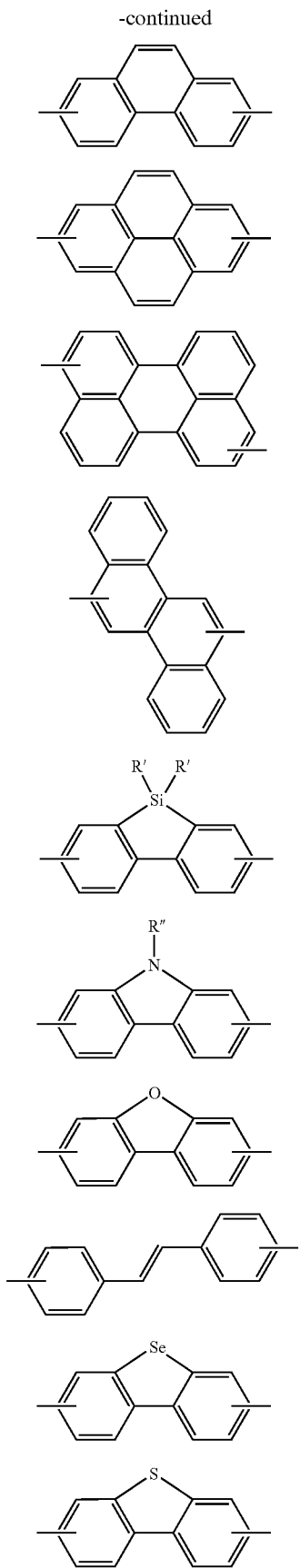

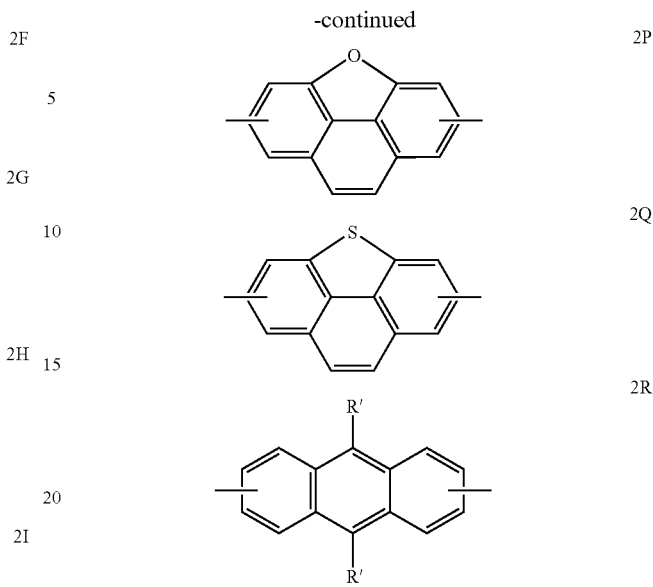

wherein R' and R" are hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group, with the proviso that, when X is H, m is 1, n is 0, and Q is Formula 2A, R' and R" are —Si($Z_3$)($Z_4$)($Z_5$) where $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

each Y is independently a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

X is hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group;

m is an integer of 1 to 3, and when m is 2 or 3, Qs may be the same or different from each other;

n is an integer of 0 to 3, and when n is 2 or 3, Ys may be the same or different from each other;

each $R_{10}$ is each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocycloalkyl group; and $R_1'$ and $R_2'$ are each independently hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group.

10. The organoelectroluminescent device of claim 7, wherein in Formulae 7 through 9, —[Y]$_n$—X is selected from the group consisting of groups represented in Formulae 10-1 to 10-116:

<Formula 10>

10-1

10-2

10-3

10-4

10-5

10-6

10-7

10-8

10-9

10-10

10-11

10-12

10-13

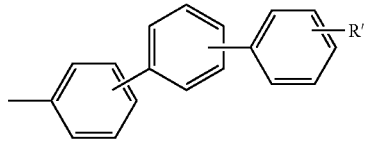
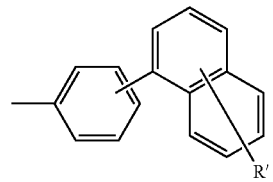
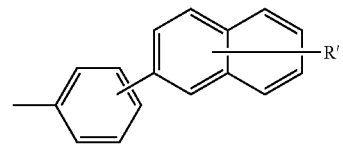
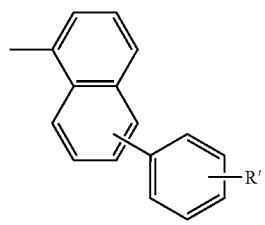
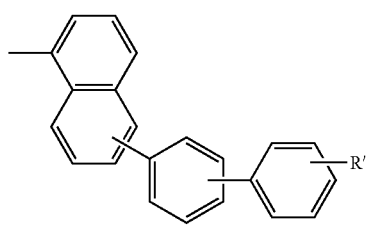
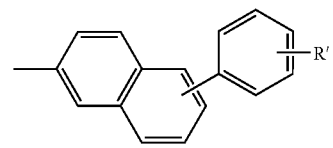
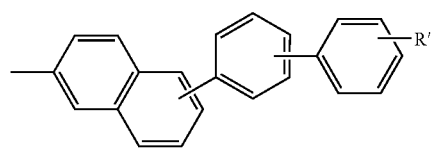
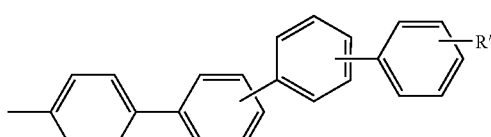
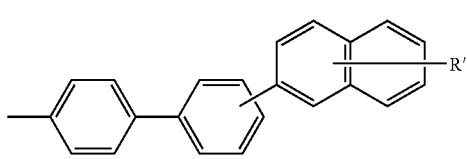
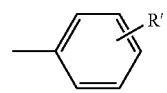
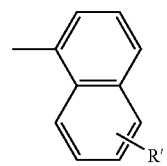
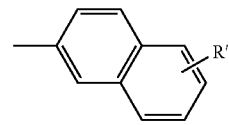
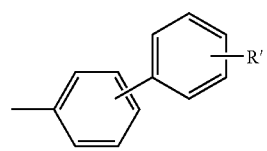

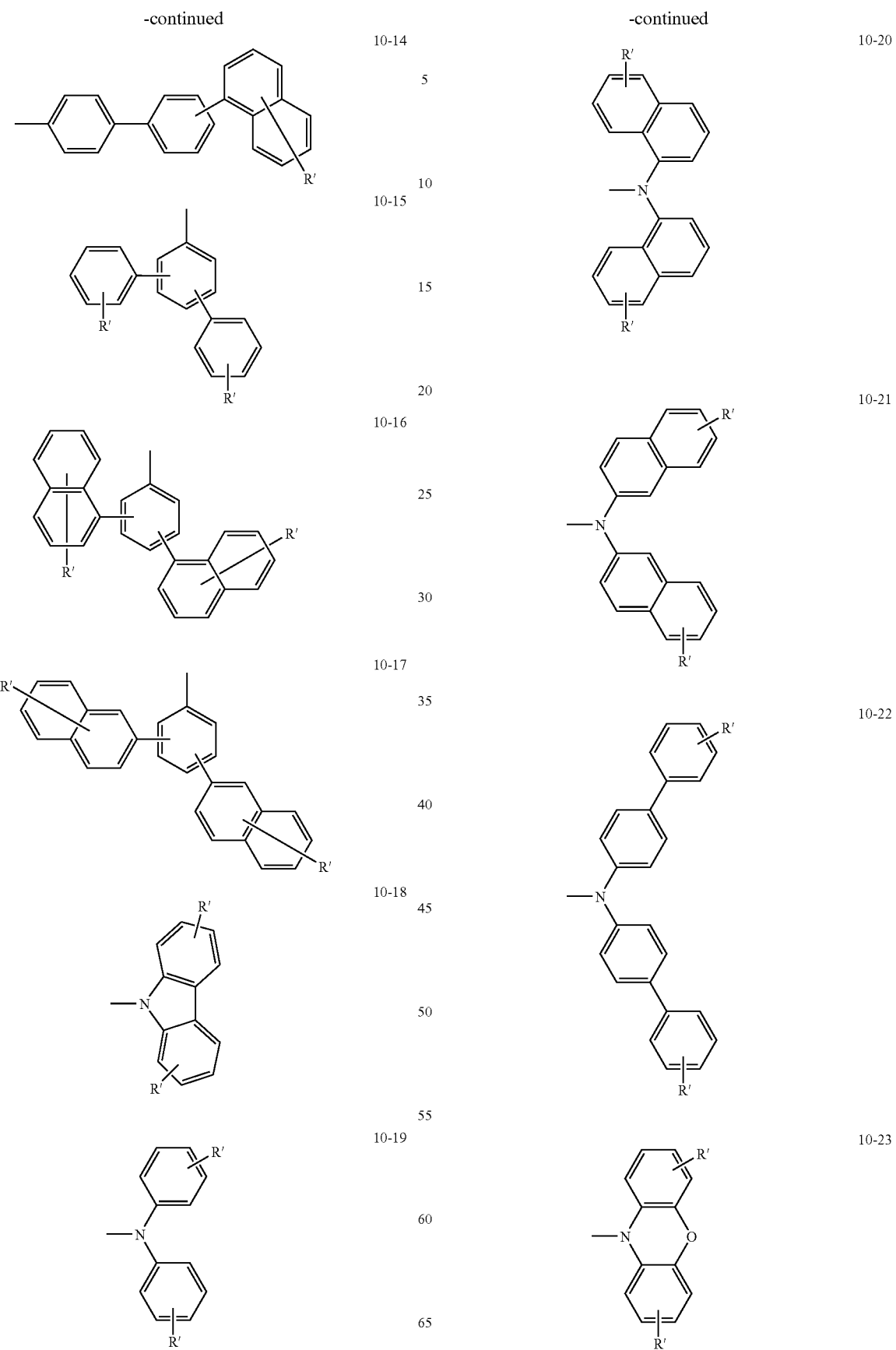

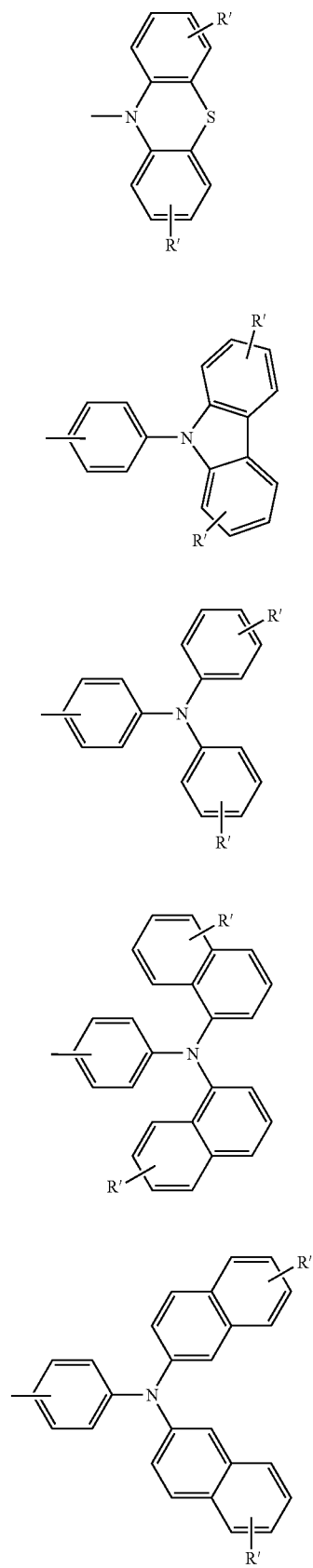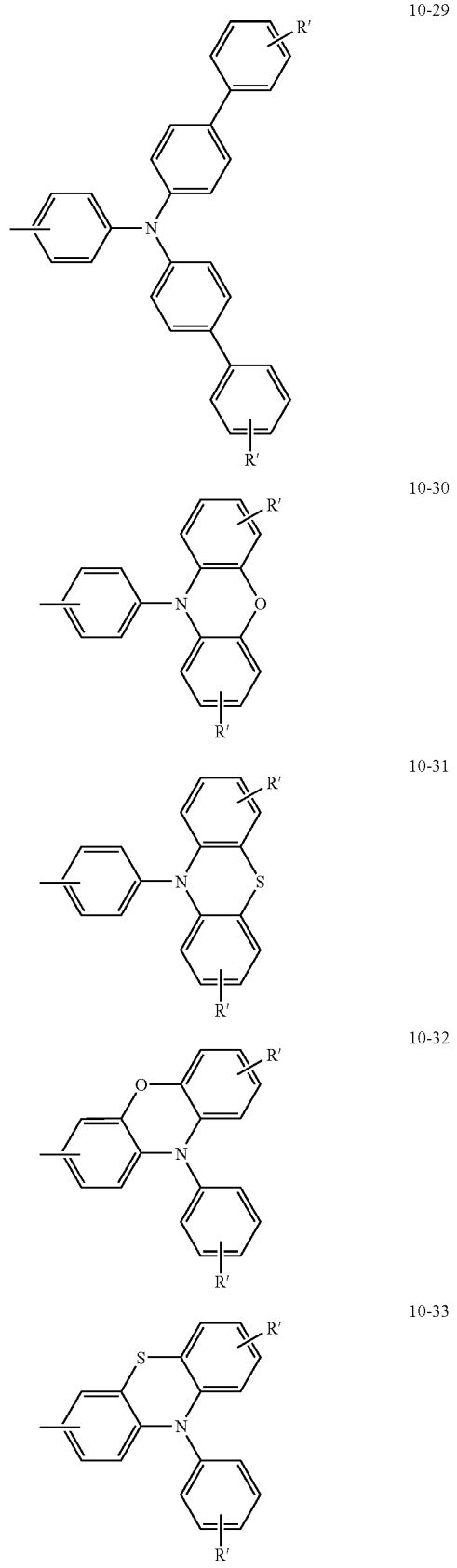

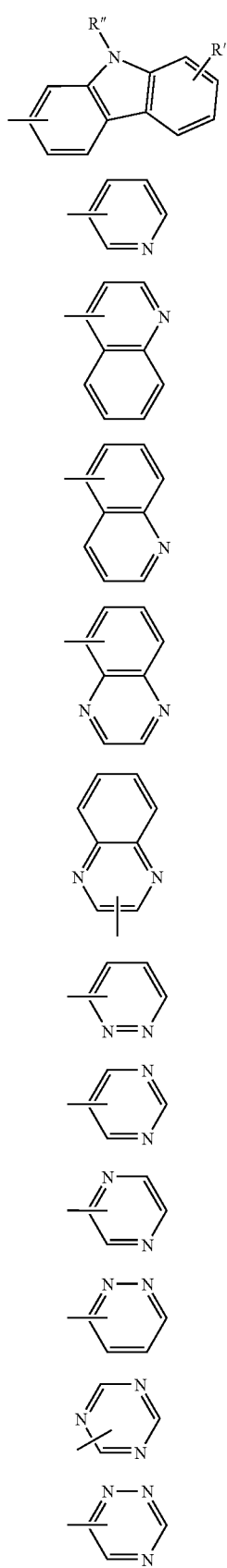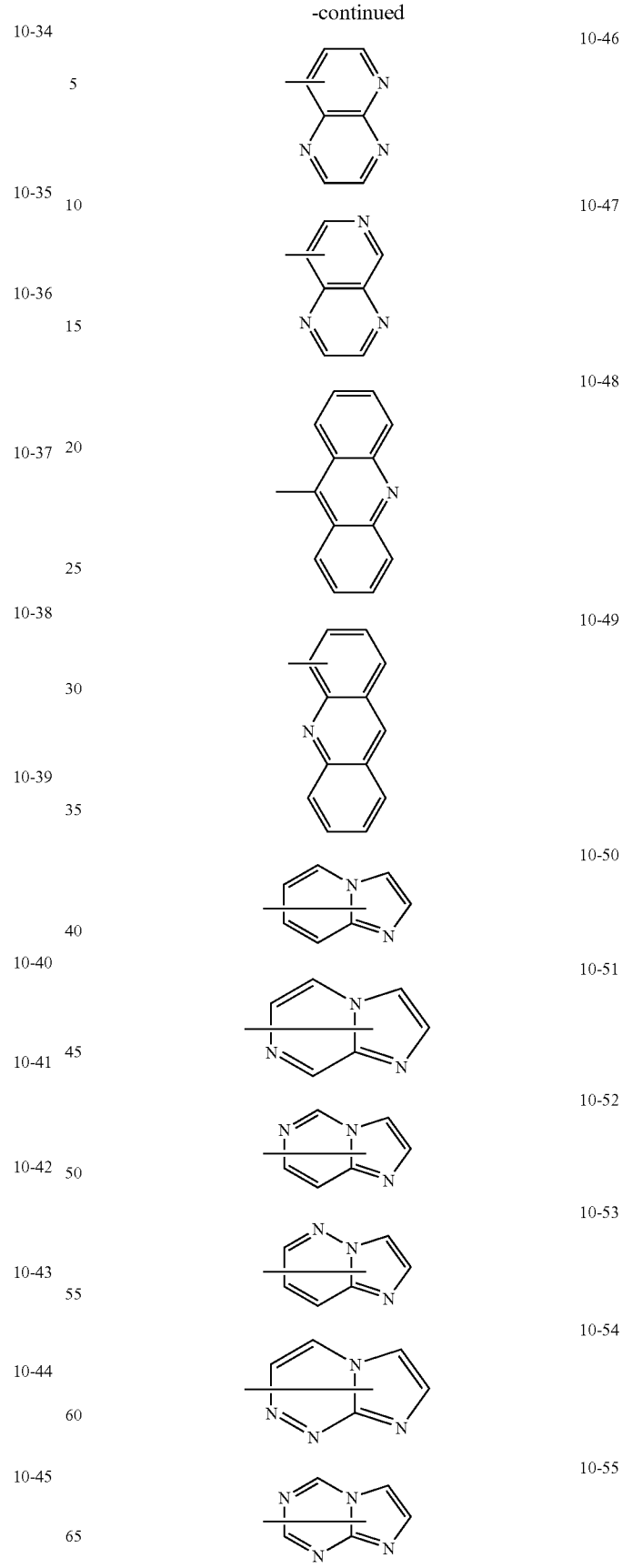

-continued
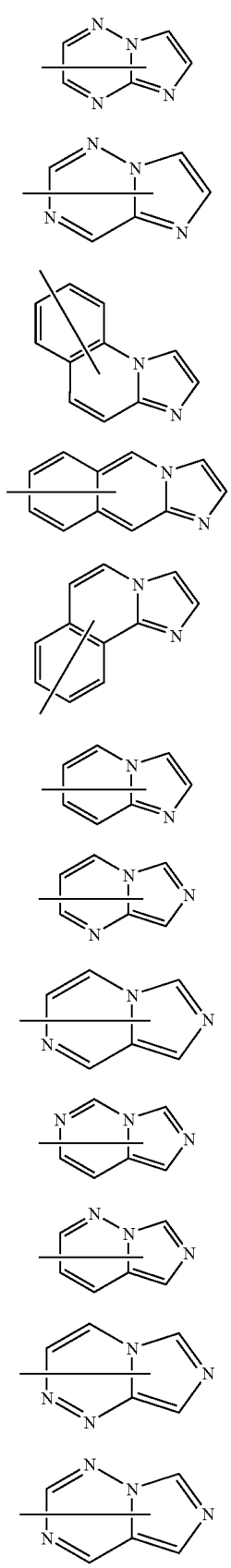
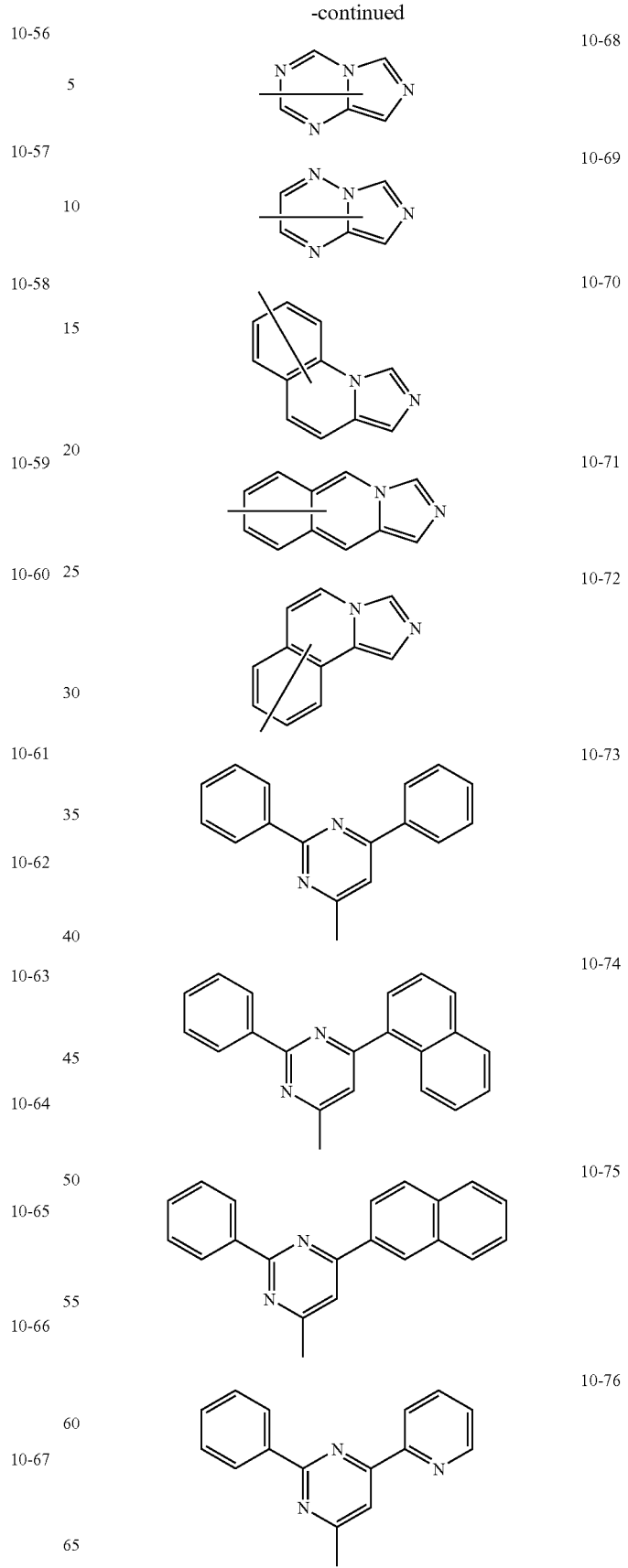

-continued
10-77 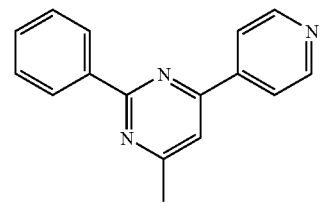
10-78 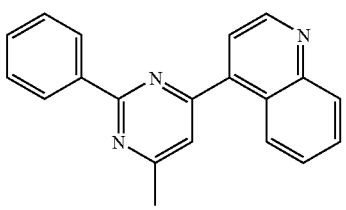
10-79 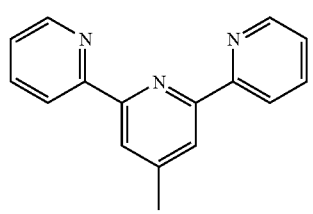
10-80 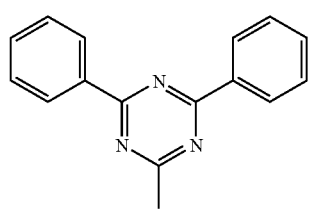
10-81 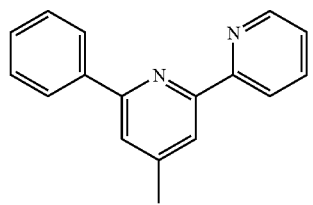
10-82 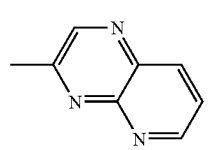
10-83 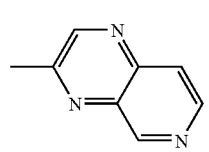
10-84 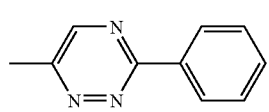
-continued
10-85 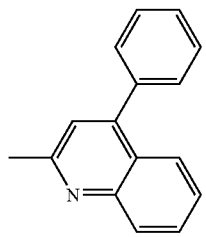
10-86 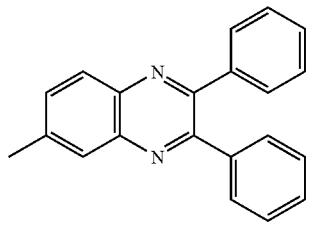
10-87 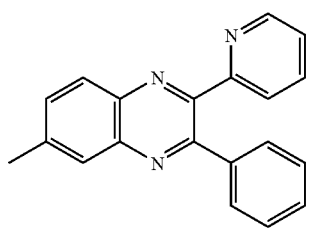
10-88 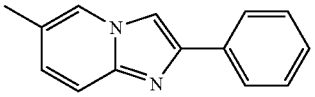
10-89 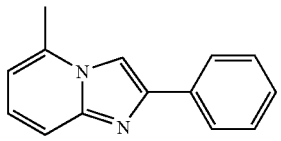
10-90 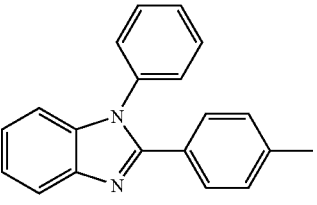
10-91 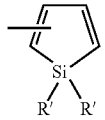
10-92 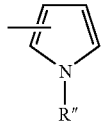
10-93 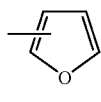
10-94 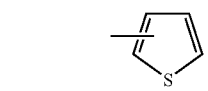

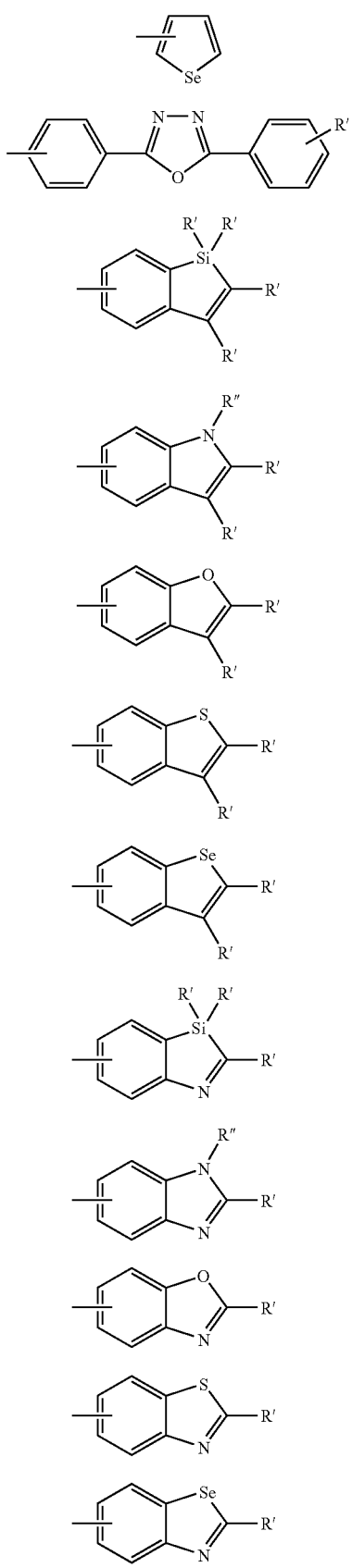
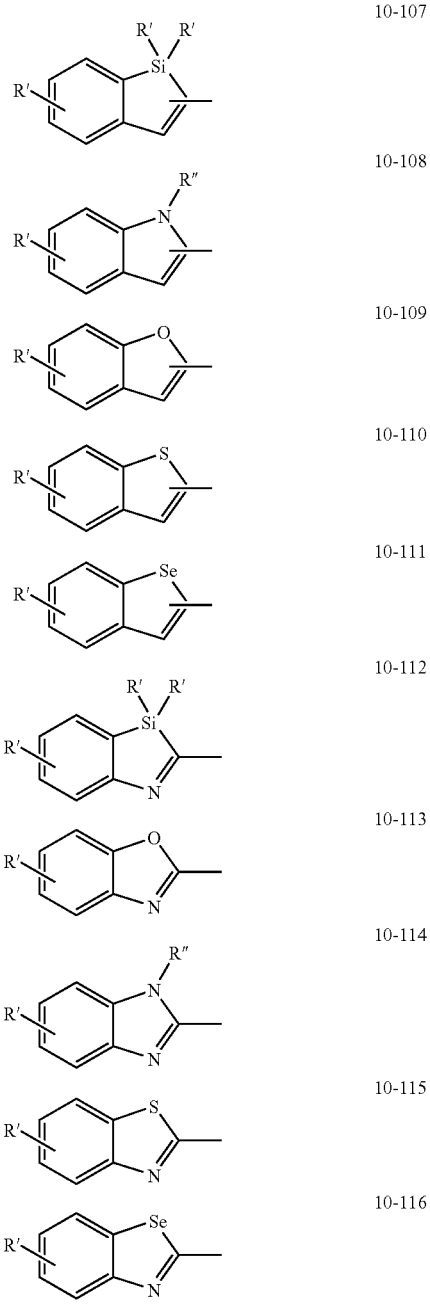

wherein R' and R" are hydrogen, halogen, a cyano group, a hydroxyl group, a substituted or unsubstituted C1-C20 alkyl group, a substituted or unsubstituted C3-C20 cycloalkyl group, a substituted or unsubstituted C5-C30 heterocycloalkyl group, a substituted or unsubstituted C1-C20 alkoxy group, a substituted or unsubstituted C6-C30 aryl group, a substituted or unsubstituted C6-C30 arylalkyl group, a substituted or unsubstituted C2-C30 heteroaryl group, —N($Z_1$)($Z_2$) or —Si($Z_3$)($Z_4$)($Z_5$) where $Z_1$, $Z_2$, $Z_3$, $Z_4$, and $Z_5$ are each independently hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C5-C30 heterocyloalkyl group.
11. The organoelectroluminescent device of claim 7, which is one selected from the group consisting of compounds represented by Formulae 15 through 43:
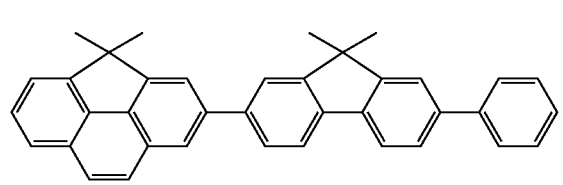
(15)
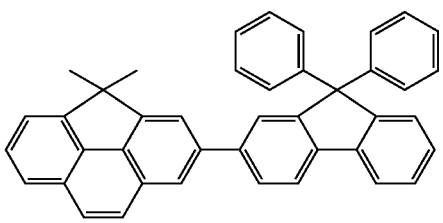
(16)
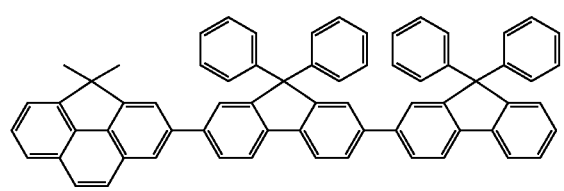
(17)
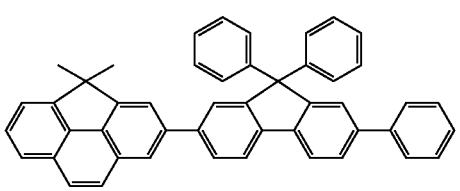
(18)
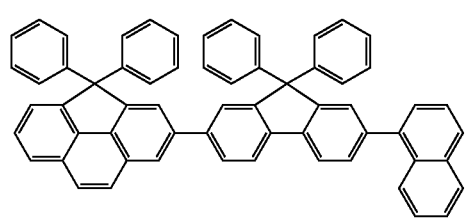
(19)
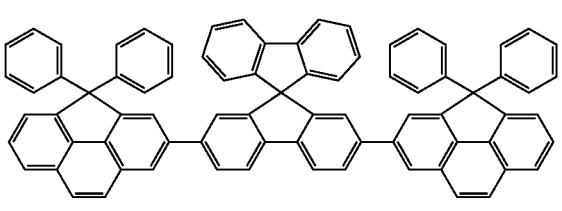
(20)
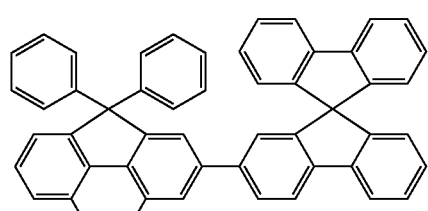
(21)
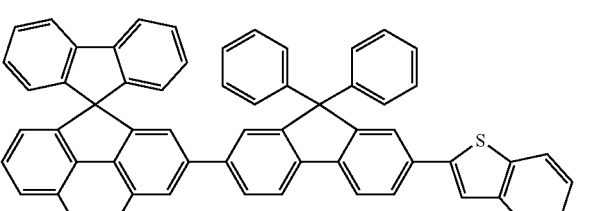
(22)
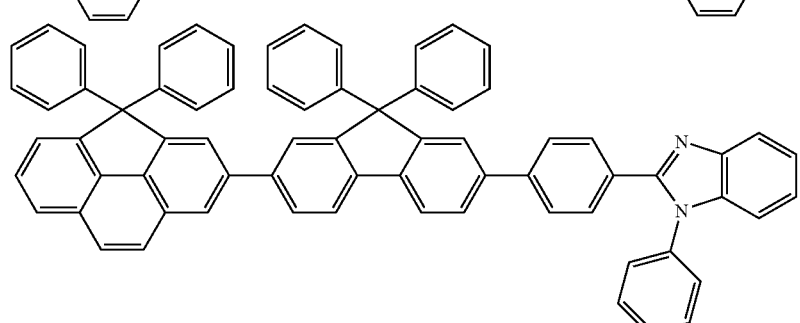
(23)
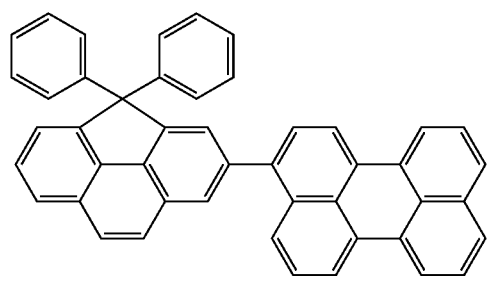
(24)
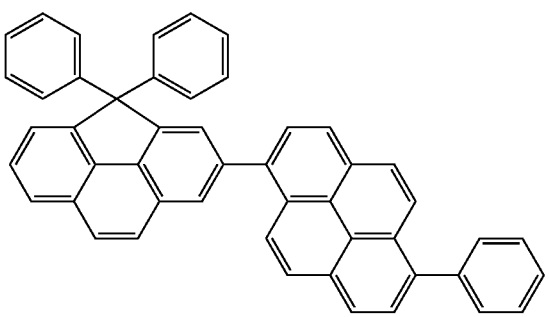
(25)

-continued
(26)
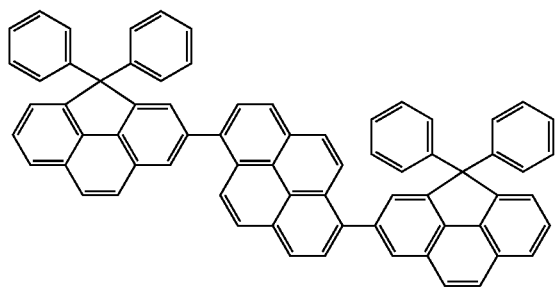
(27)
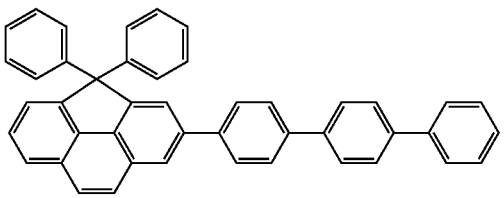
(28)
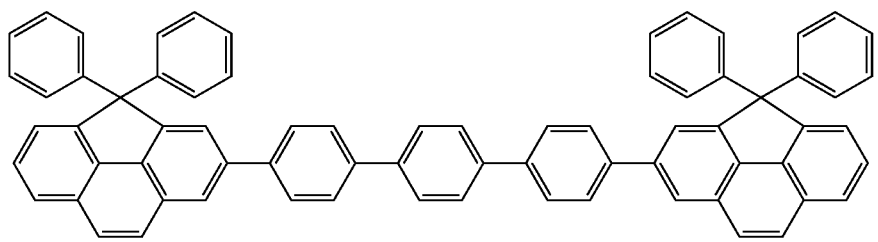
(29)
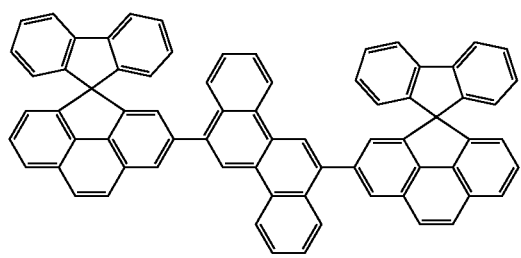
(30)
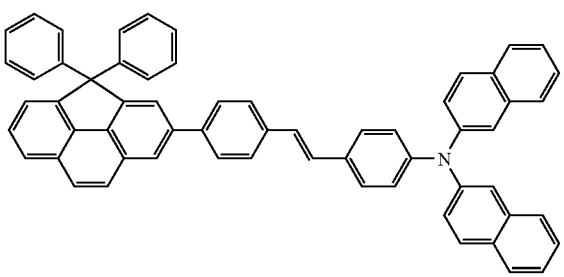
(31)
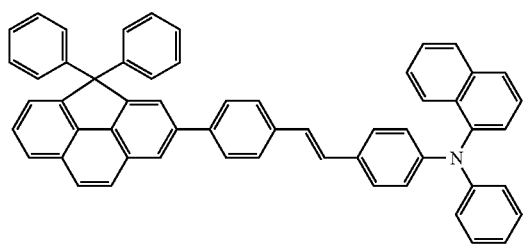
(32)
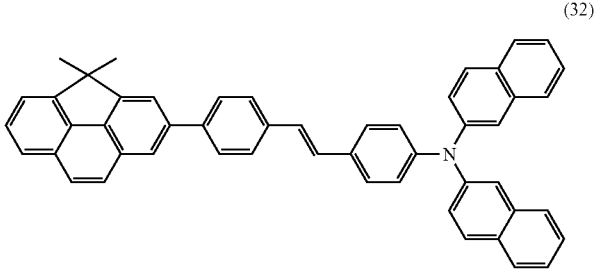
(33)
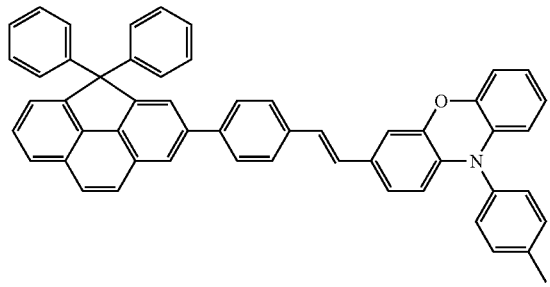

-continued
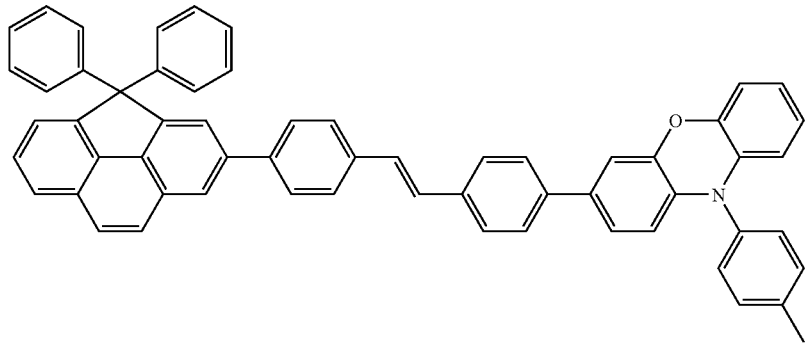
(34)
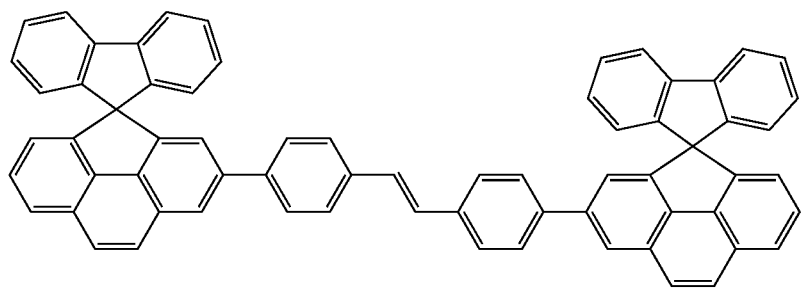
(35)
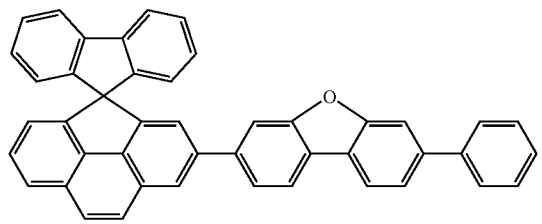
(36)
(37)
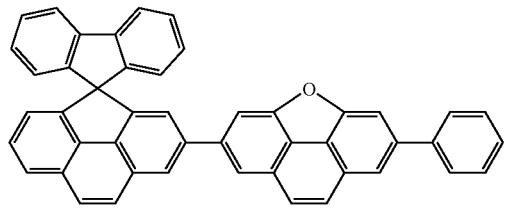
(38)
(39)
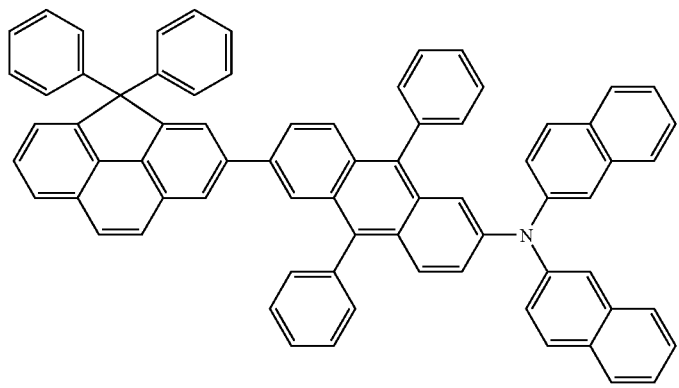
(40)

-continued

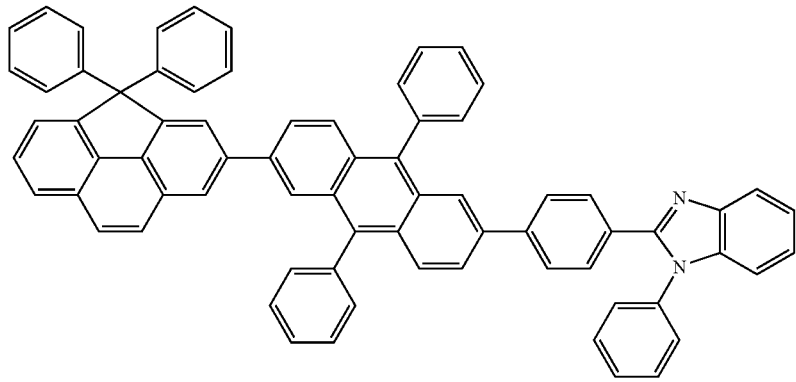
(41)

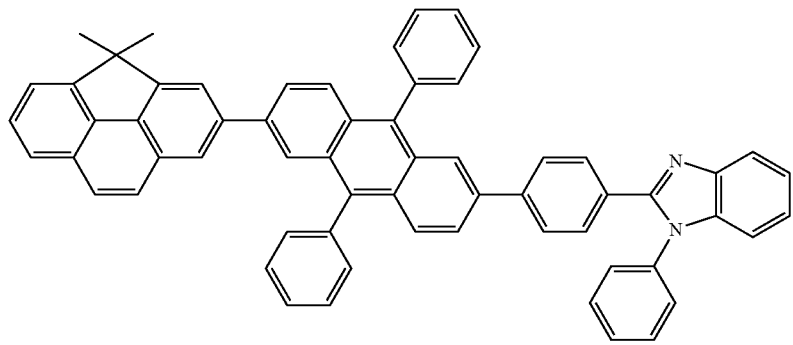
(42)

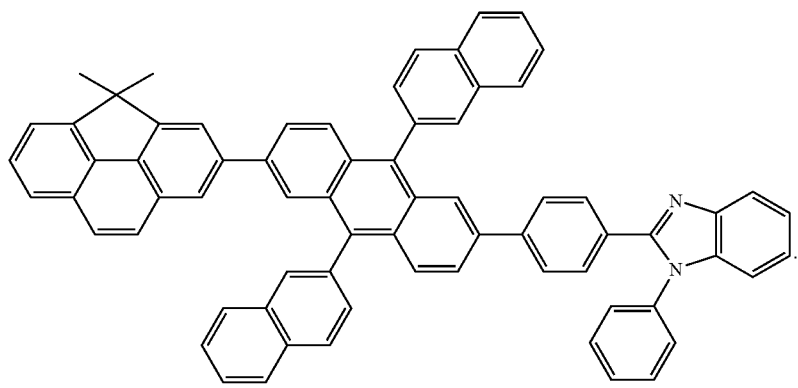
(43)

12. The organoelectroluminescent device of claim 7, wherein the organic layer is an emitting layer, a hole injection layer, or a hole transport layer.

13. The organoelectroluminescent device of claim 7, further comprising at least one selected from the group consisting of a hole injection layer, a hole transport layer, an electron blocking layer, a hole blocking layer, an electron transport layer, and an electron injection layer, between the first electrode and the second electrode.

14. The organoelectroluminescent device of claim 7, wherein the organic layer comprises an emitting layer comprising the compound of Formula 1.

15. The organoelectroluminescent device of claim 7, wherein the organic layer comprises an emitting layer consisting essentially of the compound of Formula 1 as a phosphorescent host.

16. The organoelectroluminescent device of claim 7, wherein the organic layer comprises an emitting layer comprising a host material and the compound of Formula 1 as a dopant.

17. The organoelectroluminescent device of claim 7, wherein the organic layer comprises an emitting layer comprising the compound of Formula 1 and a dopant.

18. The organoelectroluminescent device of claim 16, wherein the host material is a compound represented by Formula 46, and the compound of Formula 1 is a compound represented by Formula 30:

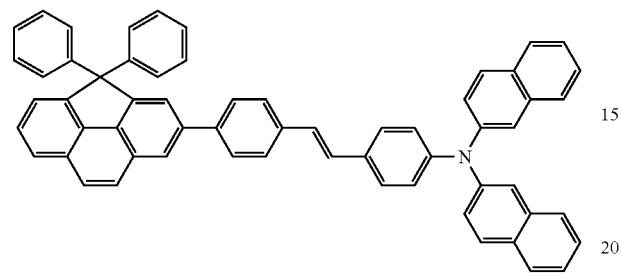
(30)

-continued

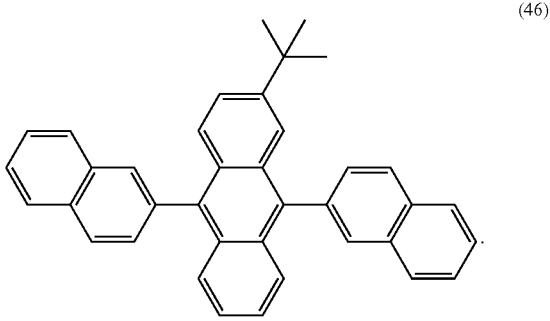
(46)

19. The organoelectroluminescent device of claim 17, wherein the compound of Formula 1 is a compound represented by one of Formula 18 and Formula 29, and the dopant is a compound represented by Formula 44:

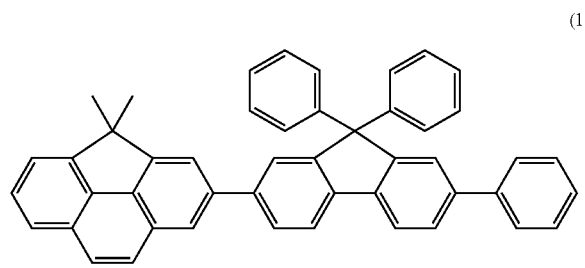
(18)

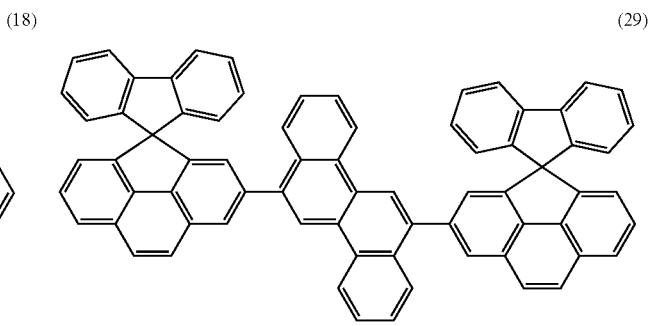
(29)

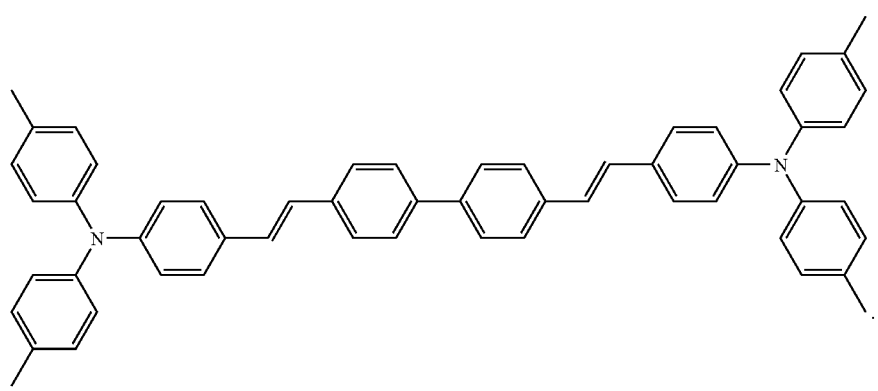
(44)

* * * * *